(12) United States Patent
Wacker et al.

(10) Patent No.: US 8,846,342 B2
(45) Date of Patent: Sep. 30, 2014

(54) BIOSYNTHETIC SYSTEM THAT PRODUCES IMMUNOGENIC POLYSACCHARIDES IN PROKARYOTIC CELLS

(75) Inventors: Michael Wacker, Unterengstringen (CH); Charles Waechter, Lexington, KY (US)

(73) Assignee: GlycoVaxyn AG, Schlieren (CH)

( * ) Notice: Subject to any disclaimer, the term of this patent is extended or adjusted under 35 U.S.C. 154(b) by 0 days.

(21) Appl. No.: 13/510,859

(22) PCT Filed: Nov. 16, 2010

(86) PCT No.: PCT/US2010/002980
§ 371 (c)(1),
(2), (4) Date: Sep. 5, 2012

(87) PCT Pub. No.: WO2011/062615
PCT Pub. Date: May 26, 2011

(65) Prior Publication Data
US 2013/0028926 A1 Jan. 31, 2013

Related U.S. Application Data

(60) Provisional application No. 61/272,931, filed on Nov. 19, 2009.

(51) Int. Cl.
*A61K 39/00* (2006.01)
*C07K 14/21* (2006.01)
*A61K 39/385* (2006.01)
*A61K 39/112* (2006.01)

(52) U.S. Cl.
CPC ........... *A61K 39/0283* (2013.01); *A61K 39/385* (2013.01)
USPC ................... 435/69.1; 435/320.1; 424/190.1; 530/395

(58) Field of Classification Search
CPC ....................................................... A61K 39/00
USPC ........................................................ 435/320.1
See application file for complete search history.

(56) References Cited

U.S. PATENT DOCUMENTS 4,689,221 A * 8/1987 Kiyoshige et al. ............... 424/49
5,242,809 A * 9/1993 Adams et al. ................. 435/69.1
(Continued)

FOREIGN PATENT DOCUMENTS

CA 1340184 12/1998
CA 2360205 8/2000
(Continued)

OTHER PUBLICATIONS

Program abstracts for the 2008 Meeting of the Society for Glycobiology, Friday Nov. 14, 2008, A Novel epimerase that converts GlcNAc-P-P Undecaprenol to GalNAc-P-P-Undecaprenol, coverage and abstract p. 945, abstract No. (22).*

(Continued)

*Primary Examiner* — Albert Navarro
*Assistant Examiner* — Ginny Portner
(74) *Attorney, Agent, or Firm* — Jones Day

(57) ABSTRACT

The invention is directed to bioconjugate vaccines comprising N-glycosylated proteins. Further, the present invention is directed to a recombinant prokaryotic biosynthetic system comprising nucleic acids encoding an epimerase that synthesizes an oligo- or polysaccharide having N-acetylgalactosamine at the reducing terminus. The invention is further directed to N-glycosylated proteins containing an oligo- or polysaccharide having N-acetylgalactosamine at the reducing terminus and an expression system and methods for producing such N-glycosylated proteins.

20 Claims, 14 Drawing Sheets

(56) References Cited

U.S. PATENT DOCUMENTS

| | | | |
|---|---|---|---|
| 5,280,113 A * | 1/1994 | Rademacher et al. | 536/55.2 |
| 5,643,758 A | 7/1997 | Guan et al. | |
| 5,665,559 A * | 9/1997 | Simonson | 435/7.32 |
| 6,365,723 B1 * | 4/2002 | Blattner et al. | 536/23.1 |
| 7,265,085 B2 * | 9/2007 | DeFrees et al. | 435/68.1 |
| 7,541,043 B2 * | 6/2009 | Kopecko et al. | 424/258.1 |
| 2002/0019342 A1 | 2/2002 | Bayer | |
| 2002/0132320 A1 * | 9/2002 | Wang et al. | 435/193 |
| 2002/0150968 A1 * | 10/2002 | Wang et al. | 435/53 |
| 2004/0067557 A1 * | 4/2004 | Endo et al. | 435/89 |
| 2004/0265954 A1 | 12/2004 | Aebi et al. | |
| 2005/0287628 A1 | 12/2005 | Aebi et al. | |
| 2010/0286067 A1 * | 11/2010 | DeFrees | 514/20.9 |
| 2011/0039729 A1 * | 2/2011 | Delisa et al. | 506/10 |
| 2011/0097357 A1 * | 4/2011 | Fernandez et al. | 424/197.11 |
| 2011/0223646 A1 * | 9/2011 | Schwartz et al. | 435/193 |
| 2011/0236934 A1 * | 9/2011 | Samain et al. | 435/97 |
| 2011/0274720 A1 * | 11/2011 | Wacker et al. | 424/203.1 |
| 2012/0100177 A1 * | 4/2012 | Ilg et al. | 424/200.1 |
| 2013/0029413 A1 * | 1/2013 | Geisler et al. | 435/348 |
| 2013/0266604 A1 * | 10/2013 | Szymanski et al. | 424/190.1 |

FOREIGN PATENT DOCUMENTS

| | | | |
|---|---|---|---|
| CA | 2477794 | 3/2003 | |
| EP | 1481057 | 2/2006 | |
| WO | WO 94/26906 | 11/1994 | |
| WO | WO 00/52135 | 9/2000 | |
| WO | WO 01/88117 | 11/2001 | |
| WO | WO 02/00856 | 1/2002 | |
| WO | WO 03/074687 | 9/2003 | |
| WO | WO 2004/013151 A2 | 2/2004 | |
| WO | WO 2005/116063 A1 | 12/2005 | |
| WO | 2006/119987 * | 11/2006 | |
| WO | WO 2006/119987 A2 | 11/2006 | |
| WO | 2009/104074 * | 8/2009 | A61K 39/02 |
| WO | WO 2009/104074 A2 | 8/2009 | |

OTHER PUBLICATIONS

Wacker, Michael et al, Science, vol. 298, Nov. 29, 2002, pp. 1790-1793, N-linked glycosylation in Campylobacter jejuni and its functional transfer into E. coli. 2.*
Abdian et al., 2000, "Identification of essential amino acids in the bacterial α-mannosyltransferase aceA", J Biol Chem; 275(51):40568-40575.
Aebi et al., 1996, "Cloning and characterization of the ALG3 gene of Saccharomyces cerevisiae", Glycobiology; 6:439-444.
Ahmed et al., 2006, "Safety and immunogenicity of Escherichia coli O157 O-specific polysaccharide conjugate vaccine in 2-5 year old children", J Infect Dis; 193(4):515-521.
Alaimo et al., 2006, "Two distinct but interchangeable mechanisms for flipping of lipid-linked oligosaccharides", EMBO J; 25:967-976.
Alexander et al., 1994, "Role of the rfe gene in the biosynthesis of the Escherichia coli O7-specific lipopolysaccharide and other O-specific polysaccharides containing N-acetylglucosamine", J Bacteriol; 176:7079-7084.
Allard et al., 2001, "Epimerases:structure, function and mechanism", Cell Mol Life Sci; 58:1650-1665.
Altmann et al., 1999, "Insect cells as hosts for the expression of recombinant glycoproteins", Glycoconjugate Journal; 16:109-123.
Amor et al., 1997, "Molecular and functional analysis of genes required for expression of group IB K antigens in Escherichia coli: characterization of the his-region containing gene clusters for multiple cell-surface polysaccharides", Mol Microbiol; 26:145-161.
Anderson, 1983, "Antibody responses to Haemophilus influenzae type b and diphtheria toxin induced by conjugates of oligosaccharides of the type b capsule with the nontoxic protein $CRM_{197}$", Infection and Immunity; 39(1):233-238.
Arbeit et al., 1984, "Predominance of two newly described capsular polysaccharide types among clinical isolates of Staphylococcus aureus", Diagn Microbiol Infect Dis; 2:85-91.

Avery et al., 1929, "Chemo-immunological studies on conjugated carbohydrate-proteins. II Immunological specificity of synthetic sugar-protein antigens", J Exp Med; 50(4):533-550.
Baggett et al., 2004, "Community-onset methicillin-resistant Staphylococcus aureus associated with antibiotic use and the cytotoxin Panton-Valentine leukocidin during a furunculosis outbreak in rural Alaska", J Infect Dis; 189:1565-1573.
Baneyx et al., 1999, "Recombinant protein expression in Escherichia coli", Curr Opin Biotechnol; 10:411-421.
Baqar et al., 1995, "Safety and immunogenicity of a prototype oral whole-cell killed Campylobacter vaccine administered with a mucosal adjuvant in non-human primates",Vaccine; 13(1):22-28.
Bematchez et al., 2005, "A single bifunctional UDP-ClcNAc/Glc 4-epimerase supports the synthesis of three cell surface glycoconjugates in Campylobacter jejuni", J Biol Chem; 280:4792-4802.
Berg et al., 1997, "2-oxo acid dehydrogenase multienzyme complexes: the central role of the lipoyl domain", Biological Chemistry; 378:617-634.
Berg et al., 2001, "Sequence properties of the 1,2-diacylglycerol 3-glucosyltransferase from acholeplasma laidlawii membranes", J Biol Chem; 276(25):22056-22063.
Bhasin et al., 1998, "Identification of a gene essential for O-acetylation of the Staphylococcus aureus type 5 capsular polysaccharide", Mol Microbiol; 27:9-21.
Bigge et al., 1995, "Nonselective and efficient fluorescent labeling of glycans using 2-amino benzamide and anthranilic acid", Anal Biochem; 230(2):229-238.
Bill et al., 1995, "Expression and mutagenesis of recombinant human and murine erythropoietins in Escherichia coli", Biochimica et Biophysica Acta; 1261:35-43.
Billman-Jacobe, 1996, "Expression in bacteria other than Escherichia coli", Curr Opin Bioteclmol; 7:500-504.
Bligh et al., 1959, "A rapid method of total lipid extraction and purification", Can J Biochem Physiol; 37(8):911-917.
Bourne et al., 2001, "Glycoside hydrolases and glycosyltransferases: families and functional modules", Current Opinion in Structural Biology; 11:593-600.
Branden et al., 1991, "Introduction to protein structure", Garland Publishing Inc., New York; pp. 247-268.
Breton et al., 1999, "Structure/function studies of glycosyltransferases", Current Opinion in Structural Biology; 9:563-571.
Bubeck Wardenburg et al., 2008, "Panton-Valentine leukocidin is not a virulence determinant in murine models of community-associated methicillin-resistant Staphylococcus aureus disease", J Infect Dis; 198:1166-1170.
Bugg et al., 1994, "From peptidoglycan to glycoproteins: common features of lipid-linked oligosaccharide biosynthesis", FEMS Microbiol Lett; 119:255-262.
Burda et al., 1999, "The dolichol pathway of N-linked glycosylation", Biochimica et Biophysica Acta; 1426:239-257.
Burr et al., 2005, "Prevention of disease in ferrets fed an inactivated whole cell Campylobacter jejuni vaccine", Vaccine; 23:4315-4321.
Butzler, 2004, "Campylobacter, from obscurity to celebrity", Clinical Microbiology and Infection; pp. 868-876.
Campbell et al., 1997, "A classification of nucleotide-diphospho-sugar glycosyltransferases based on amino acid sequence similarities", Biochem J; 326:929-939.
Canals et al., 2006, "The UDP N-acetylgalactosamine 4-epimerase gene is essential for mesophilic Aeromaonas hydrophila serotype O34 virulence", Infect & Immun; 74(1):537-548.
Cardini et al., 1957, "Enzymatic formation of acetylgalactosamine", J Biol Chem; 225:317-327.
Casburn-Jones et al., 2004, "Traveler's diarrhea", Journal of Gastroenterology and Iiepatology, 19:610-618.
CAZy (Carbohydrate-Active enZYmes) Database—GlycosylTransferase family classification (AFMB—CNRS—Universites Aix-Marseille I & II) last update: Oct. 25, 2010 at http://www.cazy.org/GlycosylTransferases.html.
CAZy (Carbohydrate-Active enZYmes) Database—Home (AFMB—CNRS—Universites Aix-Marseille I & II) last update: Oct. 25, 2010 at .cazy.org.

(56) References Cited

OTHER PUBLICATIONS

Chang et al., 2003, "Infection with vancomycin-resistant *Staphylococcus aureus* containing the vanA resistance gene", New Engl J Med; 348:1342-1347.

Chart et al., 1991, "Serological identification of *Escherichia coli* O157:H7 infection in haemolytic uraemic syndrome", The Lancet; 337:138-140.

Choi et al., 2004, "Secretory and extracellular production of recombinant proteins using *Escherichia coli*", Appl Microbiol Biotechnol; 64:625-635.

Consortium for Functional Glycomics (CFG) Nature, Functional glycomics gateway—Nomenclature, last update: Apr. 28, 2010 at functionalglycomics.org/static/consortium/Nomenclature.shtml.

Coutinho et al., 1999, "Life with no sugars?", J Mol Microbiol Biotech; 1(2):307-308.

Crooks et al., 2004, "WebLogo: A sequence logo generator", Genome Research; 14(6):1188-1190.

Cruezenet et al., 2000, "Expression, purification, and biochemical characterization of WbpP, a new UDP-GlcNAc C4 epimerase from *Pseudomonas aeruginosa* sertype O6", J Biol Chem; 275(25):19060-19067.

Crushell et al., 2004, "Enteric *Campylobacter*: purging its secrets?" Pediatric Research; 55(1):3-12.

Cunnion et al., 2001, "Capsule production and growth phase influence binding of complement to *Staphylococcus aureus*", Infect Immun; 69:6796-6803.

Datsenko et al., 2000, "One-step inactivation of chromosomal genes in *Escherichia coli* K-12 using PCR products", Proc Natl Acad Sci USA; 97:6640-6645.

Dean et al., 1999, "Characterization of the serogroup O11 O-antigen locus of *Pseudomonas aeruginosa* PA103", J Bacteriol; 181:4275-4284.

Dejonge et al., 2007, "Clinical trial of safety and efficacy of INH-A21 for the prevention of nosocomial staphylococcal bloodstream infection in premature infants", J Pediatr; 151:260-265.

Doig et al., 1996, "Characterization of a post-translational modification of *Campylobacter* flagellin: identification of a sero-specific glycosyl moiety", Molecular Microbiology; 19(2):379-387.

Dunphy et al., 1967, "The plurality of long chain isoprenoid alcohols (polyprenols) from natural sources", Biochim Biophys Acta; 136:136-147.

Expression Library Screening (Procaryotic) Using AP-fusion proteins (last visited Nov. 1, 2010) at .protocol-online.org/cgi-bin/prt/view_cache.cgi?ID=2752.

Fairweather et al, 1986, "Cloning, nucleotide sequencing, and expression of tetanus toxin fragment C in *Escherichia coli*", Journal of Bacteriology; 165(1):21-27.

Falt et al., 1996, "Construction of recombinant aroA salmonellae stably producing the *Shigella* Sysenteriae sertype 1 O-antigen and structural characterization of the *Salmonella/Shigella* hybrid LPS", Microb Pathog; 20(1).11-30.

Faridmoayer et al., 2007, "Functional characterization of bacterial oligosaccharyltransferases involved in O-linked protein glycosylation", J Bacteriol; 189(22):8088-8098.

Fass et al., 1991, "Use of high densitycultures of *Escherichia coli* for high level production of recombinant *Pseudomonas aeruginosa* exotoxin A", Applied Microbiology and Biotechnolgy, 36(1):65-69.

Fattom et al., 1990, "Synthesis and immunologic properties in mice of vaccines composed of *Staphylococcus aureus* type 5 and type 8 capsular polusaccharides conjugated to *Pseudomonas aeruginosa* exotoxin A", Infect Immun; 58:2367-2374.

Fattom et al., 1993, "Laboratory and clinical evaluation of conjugate vaccines composed of *Staphylococcus aureus* type 5 and type 8 capsular polysaccharides bound to *Pseudomonas aeruginosa* recombinant exoprotein A", Infection and Immunity; 61(3):1023-1032.

Fattom et al., 1996, "A *Staphylococcus aureus* capsular polysaccharide (CP) vaccine and CP-specific antibodies protect mice against bacterial challenge", Infect Immun; 64:1659-1665.

Fattom et al., 1998, "Antigenic determinants of *S. aureus* type 5 and type 8 capsular polysaccharide vaccines", Infect Immun; 66:4588-4592.

Feldman et al., 2005, "Engineering N-liked protein glycosylation with diverse O antigen lipopolysaccharide structures in *Escherichia coli*", Proc Natl Acad Sci USA; 102:3016-3021.

Feng et al., 2005, "Structural and genetic characterization of the *Shigella boydii* type 18 O antigen", Gene; 355:79-86.

Field et al., 2003, "Structural and mechanistic basis of bacterial sugar nucleotide-modifying enzymes", Biochemistry; 42:7637-7647.

Foster et al., 1998, "Surface protein adhesins of *Staphylococcus aureus*", Trends Microbiol; 6:484-488.

Foster, 2005, "Immune evasion by staphylococci", Nature Reviews Microbiology; 3:948-958.

Francisco et al., 1992, "Transport and anchoring of β-lactamase to the external surface of *Escherichia coli*", Proc Natl Acad Sci USA: 89:2713-2717.

Fridkin et al., 2005, "Methicillin-resistant *Staphylococcus aureus* disease in three communities", N. Engl J Med; 352:1436-1411.

Fry et al., 1998, "The lipopolysaccharide biosynthesis locus of *Campylobacter jejuni* 81116", Microbiology; 144:2049-2061.

Fujita et al., 2000, "Synthesis of neoglycoenzymes with homogenous N-linked oligosaccharides using immobilized endo-S—N-acetylglucosaminidase A", Biochmeical and Biophysical Research Communications, 267:134-138.

Gavel et al., 1990, "Sequence differences between glycosylated and non-glycosylated Asn-X-Thr/Ser acceptor sites: implications for protein engineering", Protein Eng; 3:433-442.

Gilbert et al., 2006, "Outbreak in Alberta of community-acquired (USA300) methicillin-resistant *Staphylococcus aureus* in people with a history of drug use, homelessness or incarceration", Canad Med Assoc J; 175:149-154.

Global Alliance for Vaccines and Immunization—Press releases (Mar. 11, 2006) at .gavialliance.org/media_centre/press_releases/2006_03_09_en_pr_queenrania_delhi.php.

Glover et al., 2005, "Chemoenzymatic synthesis of glycopeptides with PgIB, a bacterial oligosaccharyl transferase from *Campylobacter jejuni*", Chemistry & Biology; 12:1311-1316.

Glover et al., 2005, "In vitro assembly of the undecaprenylpyrophosphate-linked heptasaccharide for prokaryotic N-linked glycosylation", Proc Natl Acad Sci USA; 102(40):14255-14259.

"GlycoVaxyn AG appoints renowned vaccinologist Dr. Stanley Plotkin to supervisory board", Press Release (Oct. 6, 2009) available at .glycovaxyn.com/content/news/releases/09%2010%2006.pdf.

"GlycoVaxyn AG completes CHF 11.5 million series A financing to advance novel conjugated vaccine pipeline towards clinic", Press Release (Jul. 16, 2007) available at .glycovaxyn.com/content/news/releases/06%2010%2019.pdf.

"GlycoVaxyn AG raises CHF 25 million in financing led by Edmond de Rothschild Investment Partners", Press Release (Mar. 5, 2009) available at .glycovaxyn.com/downloads/GlycoVaxyn%20Financing%20Release%2005-03-09.pdf.

"GlycoVaxyn and a Harvard University affiliated hospital receive USD 3.4 million NIH grant for *Staphylococcus aureus* vaccine development", Press Release (May 4, 2010) available at .glycovaxyn.com/content/news/releases/10%2005%2004.pdf.

"GlycoVaxyn appoints Philippe Dro as CEO", Press Release (May 20, 2008) available at .sofinnova.fr/glycovaxyn-appoints-phillippe-dro-as-ceo-actu-736.php.

"GlycoVaxyn opens to partnerships; series C financing round planned for 2011, CEO says mergermarket", pp. 1-2 (Nov. 25, 2009) at .mergermarket.com/home/.

"GlycoVaxyn phase I clinical study shows positive data with *Shigella dysenteriae* vaccine candidate", (Oct. 8, 2010) available at .glycovaxyn.com/content/news/releases/10%2010%2008.pdf.

"GlycoVaxyn winner of the life sciences prize 2006", Press Release (Oct. 19, 2006) available at glycovaxyn.com/content/news/releases/06%2010%2019.pdf.

"GlycoVaxyn's first clinical study with bioconjugate vaccine initiated", Press Release (Feb. 23, 2010) available at .glycovaxyn.com/content/news/releases/10%2002%2023.pdf.

(56) References Cited

OTHER PUBLICATIONS

Goebel et al., 1929, "Chemo-immunological studies on conjugated carbohydrate-proteins" Journal of Experimental Medicine; 50(4):521-531.

Goldberg et al., 1992, "Cloning and surface expression of *Pseudomonas aeruginosa* O antigen in *Escherichia coli*", Proc Natl Acad Sci USA; 89(22):10716-10720.

Gordon et al., 1956, "Rapid paper chromatography of carbohydrates and related compounds", Anal Chem; 28:849-855.

Grabenhorst et al., 1999, "Genetic engineering of recombinant glycoproteins and the glycosylation pathway in mammalian host cells", Glycoconjugate Journal; 16:81-97.

Gray, 1979, "ELISA methodology for polysaccharide antigens: protein coupling of polysaccharides for adsorption to plastic tubes", J Immunol; 28:187-192.

Guan et al., 2005, "Extraction and identification by mass spectrometry of undecaprenyl diphosphate-MurNAc-pentapeptide-GlcNAc from *Escherichia coli*", Anal Biochem; 345:336-339.

Guerry et al., 1996, "Identification and characterization of genes required for post-translational modification of *Campylobacter coli* VC167 flagellin", Molecular Microbiology; 19(2):369-378.

Guo et al., 2007, "Three UDP-hexose 4-epimerases with overlapping substrate specificity coexist in *E. coli* O86:B7", Biochem Biophys Res Commun; 356:604-609.

Haberberger et al., 1994, "Prospects and problems for development of a vaccine against diarrhea caused by *Campylobacter*", Vaccine Research; 3:15-22.

Helenius et al., 2004, "Roles of N-linked glycans in the endopasmic reticulum", Annu Rev Biochem; 73:1019-1049.

Higgins et al., 2004, "Structure of the periplasmic component of a bacterial drug efflux pump", Proc Natl Acad Sci USA; 101:9994-9999.

Ho et al., 2006, "Preclinical laboratory evaluation of a bivalent *Staphylococcus aureus* saccharide-exotoxin A protein conjugate vaccine", Hum Vaccin; 2:89-98.

Hoffmeister et al., 2001, "Two sequence elements of glycosyltransferases involved in urdamycin biosynthesis are responsible for substrate specificity and enzymatic activity", Chem & Bio; 8:557-567.

Hofmann et al., 1993, "A database of membrane spanning protein segments", Biol Chem; 374:166 (abstract).

Hoiseth et al., 1981, "Aromatic-dependent *Salmonella typhimurium* are non-virulent and effective as live vaccines", Nature; 291:238-239.

Ihssen et al., 2010, "Production of glycoprotein vaccines in *Escherichia coli*", Microbial Cell Factories; 9(1):61.

Imperiali et al., 1991, "Differences between Asn-Xaa-Thr-containing peptides; a comparison of solution conformation and substrate behavior with oligosaccharyl-transferase", Biochemistry; 30:4374-4380.

International Search Report of International application No. PCT/CH03/00153, dated May 19, 2003, pp. 1-6.

International Search Report of International application No. PCT/EP2006/004397, dated Dec. 13, 2006, pp. 1-5.

International Search Report of International application No. PCT/EP2011/057111, dated Jul. 28, 2011, pp. 1-5.

Jeong et al., 2001, "Secretory production of human granulocyte colony-stimulating factor in *Escherichia coli*", Protein Expression and Purification; 23:211-318.

Johnson et al., 1999, "Alignment and structure prediction of divergent protein families: periplasmic and outer membrane proteins of bacterial efflux pumps", J Mol Biol; 287:695-715.

Johnson et al., 1999, "Synthesis of oligosaccharides by bacterial enzymes", Glycoconjugate Journal; 16:141-146.

Jones et al., 2005, "Revised structures for the capsular polysaccharides from *Staphylococcus aureus* types 5 and 8, components of novel glycoconjugate vaccines", Carbohydr Res; 340:1097-1106.

Josefsson et al., 2001, "Protection against experimental *Staphylococcus aureus* arthritis by vaccination with clumping factor A, a novel virulence determinant", Journal of Infectious Diseases; 184:1572-1580.

Jursch et al., 1994, "Histidine residues near the N terminus of staphylococcal alpha-toxin as reporters of regions that are critical for oligomerization and pore formation", Infect Immun; 62(6):2249-2256.

Kaniuk et al., 2004, "Investigation of the structural requirements in the lipopolysaccharide core acceptor for ligation of O antigens in the genus *Salmonella*: WaaL 'ligase' is not the sole determinant of acceptor specificity", J Biol Chem; 279:36470-36480.

Kapitonov et al., 1999, "Conserved domains of glycosyltransferases", Glycobiol; 9(10):961-978.

Karlyshev et al., 2004, "The *Campylobacter jejuni* general glycosylation system is important for attachment to human epithelial cells and in the colonization of chicks", Microbiology; 150; 1957-1964.

Kazakova et al., 2005, "A clone of methicillin-resistant *Staphylococcus aureus* among professional football players", N Engl J Mcd; 352:468-475.

Kean, 1966, "Separation of gluco- and galactocerebrosides by means of borate thin-layer chromatography", J Lipid Res; 7:449-452.

King et al., 2006, "Emergence of community-acquired methicillin-resistant *Staphylococcus aureus* USA 300 clone as the predominant cause of skin and soft-tissue infections", Ann Intern Med; 144:309-317.

Kiser et al., 1999, "*Staphylococcus aureus* cap5P encodes a UDP-N-acetylglucosamine 2-epimerase with functional redundancy", J Bacteriol; 181(16):4818-4824.

Klevens et al., 2007, "Invasive methicillin-resistant *Staphylococcus aureus* infections in the United States," Jama 298: 1763-71.

Knirel et al., 1988, "Somatic antigens of *Shigella*: structure of the O-specific polysaccharide chain of the *Shigella dysenteriae* type 7 lipoplysacharide."

Kollef et al., 2005, "Epidemiology and outcomes of health-care associated pneumonia: results from a large US database of culture-positive pneumonia." Chest 128:3854-3862.

Konadu et al. 1998, "Investigational vaccine for *Escherichia coli* O157: phase 1 study of O157 O-specific polysaccharide—*Pseudomonas aeruginosa* recombinant exoprotein A conjugates in adults", Journal of Infectious Diseases; 177(2):383-387.

Konadu et al., 1994, "Preparation, characterization, and immunological properties in mice of *Escherichia coli* O157 O-specific polysaccharide—protien conjugate vaccines", Infection and Immunity; 62(11):5048-5054.

Konadu et al., 1999, "Syntheses and immunologic properties of *Escherichia coli* O157 O-specific polysaccharide and shiga Toxin 1 B subunit conjugates in mice," Infection and Immunity; 67(11):6191-6193.

Kowarik et al., 2006, "N-Linked glycosylation of folded proteins by the bacterial oligosaccharvltransferase", Science; 314:1148-1150.

Kowarik et al., 2006, "Definition of the bacterial N-glycosylation site consensus sequence", EMBO J; 25(9):1957-1966.

Kuwahma et al., 1986, "Nucleotide sequence of the hag gene encoding flagellin of *Escherichia coli*", J Bacteriol; 168(3):1479-1483.

Laemmill, 1970, "Cleavage of Structural Proteins during the Assembly of the Head of bacteriophage T4." Nature 227:680-685.

Law, 2000, "Virulence factors of *Escherichia coli* 0157 and other Shiga Toxin-producing *E-coli*." J. App. Microbiol. 88:729-745.

Lee et al., 1997, "Protective efficacy of antibodies to the *Staphylococcus aureus* type 5 capsular polysaccharide in a modified model of endocarditis in rats." Infect Immun. 65:4146-51.

Lee et al., 1999, "Evaluation of a truncated recombinant flagellin subunit vaccine against Campy/obaeter jejuni", Infection and Immunity; 67(11):5799-5805.

Lefebre, 2002, "Construction and Evaluation of Plasmind vectors Optimized for Consitutive and Regulated Gene Expression in *Burkholderia cepacia complex* Isolates," Appl. Environ Microbiol. 68:5956-5964.

Linton et al., 2002, "Identification of N-acetylgalactosamine-containing glycoproteins PEB3 and CgpA in *Campylobacter jejuni*", Molecular Microbiology; 43(2):497-508.

(56) References Cited

OTHER PUBLICATIONS

Linton et al., 2005, "Functional analysis of the *Campylobacter jejuni* N-linked protein glycoylation pathway", Molecular Microbiology; 55(6):1695-1703.

Ltu et al., 2008, "Structure and genetics of *Shigella* O antigens." FEMS Microbiol. 32:627-653.

Lodish et al., 2000 "DNA Cloning with Plasmid vectors." Molec. Cell. Biology; 7.1 at /ncbi.nlm.nih.gov/bookshelf/br.fcgi?book=mcb&part=A1582.

Lodish et al., 2000 "Protein Glycosylation in the ER and Golgi Complex"; 17.7 at ncbi.nlm.nih.gov/bookshelf/br.fcgi?book=mcb&part=A4816.

Lowy, 1998, "*Staphylococcus aureus* infections." New Eng. J Med. 339:520-32.

Lukac et al., 1988, "Toxoid of *Pseudomonas aeruginosa* exotoxin A generated by deletion of an active-site residue", Infection and Immunity; 56(12):3095-3098.

Malissard et al., 1999, "The yeast expression system for recombinant glycosyltransferases", Glycoconjugate Journal; 16:125-139.

Maras et al., 1999, "Filamentous fungi as production organisms for glycoproteins of bio-medical interest", Glycoconjugate Journal; 16:99-107.

Marolda et al., 2006, "Interplay of the wzx translocase and the corresponding polymerase and chain length regulator proteins in the translocation and periplasmic assembly of lipopolysaccharide O antigen", Journal of Bacteriology; 188(14):5124-5135.

Marth et al., 1999, "Essentials of Glycobiology" Chapter 7 (Varki et al. eds.) available at ncbi.nlm.nih.gov/bookshelf/br.fcgi?book=glyco&part=A465.

McDevitt et al., 1995, "Indentification of the ligand-binding domain of the surface-located fibrinogen receptor (clumping factor) of *Staphylococcus aureus*." Molecular Microbiology 16:895-907.

McDougal et al., 2003, "Pulsed-field gel electrophoresis typing of oxacillin-resistant *Staphylococcus aureus* isolates from the United States; establishing a national database." J. Clin. Microbiol. 41:5113-20.

Meier-Dieter, 1990, "Biosyntehsis of enterobacterial common antigen in *Escherichia coli*." J. Biol. Chem.; 265:13490-13497.

Menzies ct al., 1996, "Passive immunization with antiserum to a nontoxic alpha-toxin mutant from *Staphylococcus aureus* is protective in a murine model." Infect Immun. 64:1839-41.

Merry et al., 2002, "Recovery of intact 2-aminobenzamide-labeled O-glycans released from glycoproteins by Hhydrazinolysis." Anal Biochem; 304(1):91-99.

Messner, 1997, "Bacterial glycoproteins," Glycoconjugate Journal 14:3-11.

Middlebrook et al., 1984, "Bacterial toxins: cellular mechanisms of action", Microbiological Reviews; 48(3): 199-221.

Mikusova et al., 2005, "Decaprenylphosphoryl Arabinofuranose, the Donor of the D-Arabinofuranosyl Residues of Mycobacterial Arabinan, is formed via a Two-Step Epimerization of Decaprenylphosphoryl Ribose." J. Bacteriol. 187:8020-8025.

Moreillon et al., 1995, "Role of *Staphylococcus aureus* coagulase and clumping factor in pathogenesis of experimental endocarditis." Infection & Immunity; 63:4738-43.

Muller et al., 2005, "An ATP-binding cassette-type cysteine transporter in *Campylobacter jejuni* inferred from the structure of an extracytoplasmic solute receptor protein", Mol Microbiol; 57:143-155.

Nairn ct al., 1990, "Solutions, emulsions, suspensions and extracts", Remington's Pharmaceutical Sciences, 18th ed., Mack Publishing Co., Chapter 83, pp. 1519-1544.

Nanra et al, 2009, "Heterogenous in vivo expression of clumping factor A and capsular polysacchardie *Staphylococcus aureus*: Implications for vaccine design." Vaccine; 27:3276-80.

Nilsson et al.m, 1997, "The role of staphylococcal polysaccharide microcapsule expression in septicemia and septic arthritis." Infect Immun 65:4216-4221.

Nita-Lazar et al., 2005, "The N-X-S/T consensus sequence is required but not sufficient for bacterial N-linked protein glycosylation", Glycobiology; 15(4):361-367.

O'Riordan et al., 2004, "*Staphylococcus aureus* capsular polysaccharides." Clin Microbiol Rev. 17(1):218-34.

Paetzel et al., 2002, "Signal peptidases", Chem Rev; 102:4549-4580.

Panina-Bordignon et al., 1989, "Universally immunogenic T cell epitopes: promiscuous binding to human MHC class II and promiscuous recognition by T cells" European Journal of Immunolgy; 19:2237-2242.

Parkhill et al., 2000, "The genome sequence of the food-borne pathogen *Campylobacter jejuni* reveals hypervariable sequences", Nature; 403:665-668.

Passwell et al., 2001, "Safety and immunogenicity of improved *Shegella* O-specific polysaccharide-protein conjugate vaccines in adults in Israel", Infection and Immunity, 69(3):1351-1357.

Paton & Paton, 1999, "Molecular Characterization of the Locus Encoding Biosynthesis of the Lipopolysaccharide O Antigen of *Escherichia coli* Serotype O113," Infect & Immun 67(11): 5930-5937.

Pawlowski, 2000, "Preparation of pneumococcal capsular polysaccharide-protein conjugate vaccines utilizing new fragmentation and conjugation technologies." Vaccine 18:1873-1885.

Pearson et al., 2003, "Comparative genome analysis of *Campylobacter jejuni* using whole genome DNA microarrays", FEBS Letter; 554: 224-230, FEBS 27782.

Perry, 1986, "Structure of the O-chain polysaccharide of the phenol-phase soluble lipopolysaccharide of *Escherichia coli* O:157:h7." Biochem. Cell Biol.; 64:21-28.

Petrescu et al., 2004, "Statistical analysis of the protein environment of N-glycosylation sites: implications for occupancy, structure, and folding", Glycobiology; 14(2):103-114.

Pozscay et al., 1999, "Protein conjugates of synthetic saccharides elicit higher levels of serum IgG lipopolysaccharide antibodies in mice than do those of the O-specific polysaccharide from *Shigella dysenteriae* type 1", Proc Natl Acad Sci USA; 96:5194-5197.

Pozsgay, 1998, "Synthesis of glycoconjugate vaccines again *Shigella dysenteriae* type 1", Journal of Organic Chemistry; 63:5983-5999.

Qian et al., 2007, "Conjugating recombinant proteins to *Psudomonas aeruglnosa* Exoprotein A: A strategy for enhancing immunogenicity to malaria vaccine candidates." Vaccine 25:3923-3933.

Raetz et al., 2002, "Lipopolysaccharide endotoxins", NIH-PA author manuscript, pp. 1-57, 19-25 (published in final edited form as: Annual Rev Biochem; 71:635-700, 2002.

Reeves et al., 1996, "Bacterial polysaccharide synthesis and gene nomenclature", Reviews, Elseview Science Ltd., pp. 495-503.

Robbins et al, 2009, "Synthesis, characterization, and immunogenicity in mice on *Shigella sonnei* O-specific oligosacchardie-core-protein conjugates." Proc. Natl. Acad Sci USA 106:7974-7978.

Royle et al., 2002, "An analytical and structural database provides a strategy for sequencing O-glycans from microgram quantities of glycoproteins." Anal Biochem; 304(1): 70-90.

Rubires, 1997, "A gene (wbbL) from *Serratia marcesens* N28b (O4) complements the rfb-50 mutation of *Escherichia coli* K-12 derivatives" J Bacteriol 179(23):7581-7586.

Rudd et al., 1997, "Glycosylation: heterogeneity and the 3D structure of proteins", Crit Rev Biochem Mol Biol; 32:1-100.

Rush, 1997, "Polyisoprenyl phosphate specificity of UDP-GlcNAc: undecaprenyl phosphate N-acetylgluosaminyl 1-P transferase from *E. coli*" Glycobiology; 7:315-322.

Sambrook & Russell, 2006, "Screening Bacterial Colonies by Hybridization: Small Numbers." Cold Spring Harb. Protoc; doi:10.1101/pdb.prot3925 at shprotocols.cshlp.org/cgi/content/full/2006/2/pdb.prot3925.

Samuel, 2003, "Biosynthesis of O-antigens: genes and pathways involved in nucleotide sugar precursor synthesis and O-antigen assembly." Carbohydrate Res. 338: 2503-2519.

Sau et al., 1997, "The *Staphylococcus aureus* allelic genetic loci for serotype 5 and 8 capsule expression contain the type-specific genes flanked by common genes." Microbiology 143: 2395-405.

Schaad et al., 1991, "Safety and immunogenicity of *Pseudomonas aernginosa* conjugate A vaccine in cystic fibrosis", The Lancet; 338:1236-1237.

(56) References Cited

OTHER PUBLICATIONS

Schaffer et al, 2008, "Vaccination and passive immunisation against *Staphylococcus aureus*" Ing J Antimicrob Agents 32 Suppl. 1:S71-78.

Schneerson et al., 1991, "Preparation, characterization, and immunogenicity of *Haemophilus influenzae* type B polysaccharide-proteins conjugates", Journal of Experimental Medicine; 152:361-376.

Schultz et al., 1998, "Prototype of a heme chaperone essential for cytochrome c maturation", Science; 281:1197-1200.

Schwimmer et al., 1956, "Reagent for Differentiation on 1,4- and 1,6-Linked Glucosaccharides." Science; 123:543-544.

Scott, 1997, "Vaccines against *Campylobacter jejuni*", Journal of Infectious Diseases; 176(Suppl. 2):S183-S188.

Seffernick et al., 2001, "Melamine deaminase and atrazine chlorohydrolase: 98 percent identical but functionally different", J Bacteriol; 183(8):2405-2410.

Shorr, 2007, "Epidemiology and economic impact of meticillin-resistant *Staphylococcus aureus*: review and analysis of the literature." Phamacoeconomis 25: 751-68.

Simons et al., 1984, "High-level expression of human interferon gamma in *Escherichia coli* under control of the $p_L$ promoter of bacteriophage lambda", Gene; 28:55-64.

Spears et al., 2006, "A comparison of enterphathogenic *Escherichia coli* pathogenesis," FEMS Microbiol. Lett 255:187-202.

Spirig et al., 1997, "The STT3 protein is a component of the yast oligosaccharyltransferase complex." Mol. Gen Genet 356:628-637.

Stenutz, 2006, "The structures of *Escherichia coli* O-polysaccharide antigens." FEMS Microbiol. Rev. 30:382-403.

Stephan et al., 2004, "First isolation and further characterization of enteropathogenic *Escherichia coli* (EPC) O 157:H45 strains from cattle" BMC Microbiol. 4:10.

Stevenson, 1994, "Structure of the O Antigen of *Escherichia coli* K-12 and the Sequence of rfb Gene Cluster." J Bacteriol.; 176:4144-4156.

Sullam, 1996, "Diminished platelet binding in vitro by *Staphylococcus areus* is associated reduced virulence in a rabbit model of infective endocarditis." Infection & Immun. 66:5183-5189.

Szu et al., 1994, "Laboratory and preliminary clinical characterization of Vi capsular polysaccharide-protein conjugate vaccines", Infection and Immunity; 62(10):4440-4444.

Szymanski et al., 1999, "Evidence for a system of general protein glycosylation in *Campylobacter jejuni*", Molecular Microbiology; 32(5):1022-1030.

Szymanski et al., 2002, "*Campylobacter* protein glycosyation affects host cell interactions", Infection and Immunity; 70(4):2242-2244.

Szymanski et al., 2005, "Protein glycosylation in bacterial mucosal pathogens", Nature Reviews, Microbiology; 3:225-237.

Taylor et al., 1993, "Synthesis, characterization and clinical evaluation of conjugate vaccines composed of the O-specific polysaccharides of *Shigella dysenteriae* type 1, *Shigella flexneri* type 2a, and *Shigella sonnei* (*Plesiomonas shigelloides*) bound to bacterial toxoids", Infection and Immunity; 61(9):3678-3687.

Thakker et al., 1998, "*Staphylococcus aureus* serotype 5 capsular polysaccharide is antiphagocytic and enhances bacterial virulence in a murine bactermia model." Infect Immun. 66:5183-5189.

Thibault et al., 2001, "Identification of the carbohydrate moieties and glycosylation motifs in *Campylobactor jejuni* flagellin", J Biol Chem; 276(37):34862-34870.

Tsai et al., 1982, "A sensitive silver stain for detecting lipopolysaccharides in polyacrylamide gels." Anal Biochem. 119:115-119.

Tuchscherr, 2008, "Antibodies to capsular polysaccharide and clumping factor A prevent mastitis and the emergence of uncapsulated and small-colony variants of *Staphylococcus aureus* in mice." Infect Immun 76:5738-44.

Unligil et al., 2000, "Glycosyltransferase structre and mechanism." Curr. Op. Struct. Bio. 10:510-517.

Valvano, 2003, "Export of O-specific lipopolysaccharide", Front Biosci; 8:s452-471.

Vanbleu et al., 2004, "Genetic and physical map of the pLAFR1 vector DNA seq." 15(3): 225-227.

Vandaux et al, 1995, "Use of adhesion-defective mutants of *Staphylococcus aureus* to define the role of specific plasma proteins in promoting bacterial adhesion to canine arteriovenous shuts." Infect & Immunity 63:585-90.

Varki et al., 1999, "Essentials of Glycobiology", Cold Spring Harbor Laboratory Press; Cold Spring Harbor, New York pp. 85-100.

Vernachio et al., 2003, "Anti-clumping factor A immunoglobulin reduces the duration of methicillin-resistant *Staphylococcus aureus* bacteremia in an experimental model of infective endocarditis," Antimicrobial Agents & Chemotherapy, 47:3400-3406.

Wacheter et al., 1976, "Lipid Intermediates Involved in the Assembly of Membrane-Associated Glycoproteins in Calf Brain White Matter." Arch Biochem Biophys.; 174:726-737.

Wacker et al., 2001, "PgIB, an oligosaccharyltransferase in the eubacterium *Campylobacter jejuni*?", Glycobiology; 11:871.

Wacker et al., 2002, "N-linked glycosylation in *Campylobacter jejuni* and its functional transfer into *E. coli*", Science; 298:1790-1793.

Wacker et al., 2006, "Substrate specificity of bacterial oligosaccharyltransferase suggests a common transfer mechanism for the bacterial and eukaryotic systems", Proc Natl Acad Sci; 103:7088-7093.

Waechter et al., 1977, "Evidence for the Enzymatic Transfer of N-Acetylglucosamine form UDP-N-Acetylglucosamine into Dolichol Derivates and glycoproteins by Calf Brain Membrane." Arch. Biochem. Biophys. 181:185-198.

Wang et al., 2002, "The O-Antigen gene Cluster of *Escherichia coli* O55:H7 and Identification of a New UDP-GlcNAc C4 Epimerase Gene." J Bacteriol 184:2620-2625.

Wang et al.,1998, "Organization of *Escherichia coli* 0157 O Antigen Gene cluster and Identification of its specific genes." Infect. Immune 66:3545-3551.

Watts et al., 2005, "*Staphylococcus aureus* strains that express serotype 5 of srotype 8 capsular polysaccharides differ in virulence," Infect Immun. 73:3502-11.

Wernerus et al., 2004, "Biotechnological applications for surface-engineered bacteria", Biotechnol Appl Biochem; 40:209-228.

Whisstock et al., 2003, "Prediction of protein function from protein sequence and structure", Q Rev Biophys; 36(3):307-340.

Whitfield et al., 1999, "Structure, assembly and regulation of express of capsules in *Escherichia coli*", Molecular Microbiology; 31(5):1307-1319.

Whitfield et al., 2006, "Biosynthesis and Assembly of Capsular Polysaccharides in *Escherichia coli*." Annu Rev. Biochem. 75:39-68.

Witkowski et al., 1999, "Conversion of a beta-ketoacyl synthase to a malonyl decarboxylase by replacement of the active-site cysteine with glutamine", Biochemistry; 38(36):11643-11650.

Wolfe et al., 1993, "Reactions adding Sugar Units to Proteins in the ER and Golgi Complex, Molecular and Cellular Biology." Wadsworth Publishing Co., CA 873-75.

Wyszynska et al., 2004, "Oral immunization of chickens with avirlent salmonella vaccine strain carrying *C. jejuni* 72Dz/92 cjaA gene elicits specific humoral immune response associated with protection against challenge with wild-type *Campylobacter*", Vaccine; 22:1379-1389.

Yao et al., 1994, "Isolation of motile and non-motile insertional mutants of *Campylobacter jejuni*: the role of motility in adherance and invasion of eukaryotic cells", Molecular Microbiology; 14(5):883-893.

Young et al., 2002,"Structure of the N-linked glycan present on multiple glycoproteins in the gramnegative bacterium, *Campylobacter jejuni*", J Biol Chem; 277(45):42530-42539.

Zhang et al., 1997, "Molecular and chemical characterization of the lipopolysaccharide O-antigen and its role in the virulence of *Yersinia enterocolitica* serotype O:8." Mol. Microbiol. 23:63-76.

Zufferey eta l., 1995, "STT3, a highly conserved protein required for yeast oligosaccharyl transferase activity in vivo." The EMBO Journal 14(20):4949-4960.

\* cited by examiner

BIOSYNTHETIC SYSTEM THAT PRODUCES IMMUNOGENIC POLYSACCHARIDES IN PROKARYOTIC CELLS

CROSS-REFERENCE TO RELATED APPLICATION

This application is a U.S. national stage patent application of International Patent Application No. PCT/US2010/002980, filed Nov. 16, 2010, which claims the benefit under 35 U.S.C. §119(e) of U.S. Provisional Patent Application No. 61/272,931, filed Nov. 19, 2009, each of which is herein incorporated by reference in its entirety.

FIELD OF THE INVENTION

The present invention relates to the use of a biosynthetic system and proteins for preparing a vaccine. In addition, the invention relates to a recombinant prokaryotic biosynthetic system having an epimerase that initiates the synthesis of an oligo- or polysaccharide with a specified monosaccharide at the reducing terminus. The invention further relates to N-glycosylated proteins produced with glycans in an expression system and bioconjugate vaccines made from said N-glycosylated proteins comprising immunogenic glycans, and provides methods for producing N-glycosylated proteins.

BACKGROUND OF THE INVENTION

Glycoproteins are proteins that have one or more covalently attached sugar polymers. N-linked protein glycosylation is an essential and conserved process occurring in the endoplasmic reticulum of eukaryotic organisms. It is important for protein folding, oligomerization, stability, quality control, sorting and transport of secretory and membrane proteins (Helenius, A., and Aebi, M. (2004). Roles of N-linked glycans in the endoplasmic reticulum. Annu. Rev. Biochem. 73, 1019-1049).

Protein glycosylation has a profound influence on the immunogenicity, the stability and the half-life of a protein. In addition, glycosylation can assist the purification of proteins by chromatography, e.g. affinity chromatography with lectin ligands bound to a solid phase interacting with glycosylated moieties of the protein. It is therefore established practice to produce many glycosylated proteins recombinantly in eukaryotic cells to provide biologically and pharmaceutically useful glycosylation patterns.

WO 2003/07467 (Aebi et al.) demonstrated that the food-borne pathogen *Campylobacter jejuni*, which is a bacterium, could N-glycosylate its proteins, which was a unique feature among known prokaryotic organisms except for certain species of archaea. The machinery required for glycosylation is encoded by 12 genes that are clustered in the so-called pgl locus. Disruption of N-glycosylation affects invasion and pathogenesis of *C. jejuni* but is not lethal as in most eukaryotic organisms (Burda P. and M. Aebi, (1999). The dolichol pathway of N-linked glycosylation. Biochem Biophys Acta 1426(2):239-57). It is possible to reconstitute the N-glycosylation of *C. jejuni* proteins by recombinantly expressing the pgl locus and acceptor glycoprotein in *E. coli* at the same time (Wacker et al. (2002). N-linked glycosylation in *Campylobacter jejuni* and its functional transfer into *E. coli*. Science 298, 1790-1793).

N-glycans have a glycan attached to a consensus sequence in a protein. The known N-glycosylation consensus sequence in a protein allows for the N-glycosylation of recombinant target proteins in prokaryotic organisms. Such organisms comprise an oligosaccharyl transferase ("OT"; "OTase"), such as, for example, an oligosaccharyl transferase of *C. jejuni*, which is an enzyme that transfers the glycan to the consensus sequence of the protein.

WO 2003/07467 (Aebi et al.) teaches a prokaryotic organism into which is introduced a nucleic acid encoding for (i) specific glycosyltransferases for the assembly of an oligosaccharide on a lipid carrier, (ii) a recombinant target protein comprising a consensus sequence "N-X-S/T", wherein X can be any amino acid except proline, and (iii) an oligosaccharyl transferase, such as, for example, an oligosaccharyl transferase of *C. jejuni* that covalently links said oligosaccharide to the consensus sequence of the target protein. Said prokaryotic organism produces N-glycans with a specific structure which is defined by the type of the specific glycosyltransferases.

WO 2006/119987 (Aebi et al.) describes proteins, as well as means and methods for producing proteins, with efficiency for N-glycosylation in prokaryotic organisms in vivo. It further describes an efficient introduction of N-glycans into recombinant proteins for modifying immunogenicity, stability, biological, prophylactic and/or therapeutic activity of said proteins, and the provision of a host cell that efficiently displays recombinant N-glycosylated proteins of the present invention on its surface. In addition, it describes a recombinant N-glycosylated protein comprising one or more of the following N-glycosylated optimized amino acid sequence(s):

D/E-X-N-Z-S/T (SEQ ID:31; optimized consensus sequence), wherein X and Z may be any natural amino acid except Pro, and wherein at least one of said N-glycosylated partial amino acid sequence(s) is introduced. The introduction of specific partial amino acid sequence(s) (optimized consensus sequence(s)) into proteins leads to proteins that are efficiently N-glycosylated by an oligosaccharyl transferase in these introduced positions.

The biosynthesis of different polysaccharides is conserved in bacterial cells. The polysaccharides are assembled on carrier lipids from common precursors (activated sugar nucleotides) at the cytoplasmic membrane by different glycosyltransferases with defined specificity. Lipopolysaccharides ("LPS") are provided in gram-negative bacteria only, e.g. *Shigella* spp., *Pseudomonas* spp. and *E. coli* (ExPEC, EHEC).

The synthesis of LPS starts with the addition of a monosaccharide to the carrier lipid undecaprenyl phosphate ("Und-P-P") at the cytoplasmic side of the membrane. The antigen is built up by sequential addition of monosaccharides from activated sugar nucleotides by different glycosyltransferases, and the lipid-linked polysaccharide is flipped through the membrane by a flippase. The antigen-repeating unit is polymerized by an enzymatic reaction. The polysaccharide is then transferred to the Lipid A by the Ligase WaaL forming the LPS that is exported to the surface, whereas the capsular polysaccharide is released from the carrier lipid after polymerization and exported to the surface. The biosynthetic pathway of these polysaccharides enables the production of LPS bioconjugates in vivo, capturing the polysaccharides in the periplasm to a protein carrier.

Such synthesized complexes of oligo- or polysaccharides (i.e., sugar residues) and proteins (i.e., protein carriers) can be used as conjugate vaccines to protect against a number of bacterial infections. Conjugate vaccines have been successfully used to protect against bacterial infections. The conjugation of an antigenic polysaccharide to a protein carrier is required for protective memory response, as polysaccharides are T-cell independent immunogens. Polysaccharides have been conjugated to protein carriers by different chemical methods, using activation reactive groups in the polysaccharide as well as the protein carrier.

Conjugate vaccines can be administered to children to protect against bacterial infections and also can provide a long lasting immune response to adults. Constructs of WO 2009/104074 (Fernandez, et al.) have been found to generate an IgG response in animals. It has been found that an IgG response to a *Shigella* O-specific polysaccharide-protein conjugate vaccine in humans correlates with immune protection in humans. (Passwell, J. H. et al., "Safety and Immunogenicity of Improved *Shigella* O-Specific Polysaccharide-Protein Conjugate Vaccines in Adults in Israel" Infection and Immunity, 69(3):1351-1357 (March 2001).) It is believed that the polysaccharide (i.e. sugar residues) triggers a short-term immune response that is sugar-specific. Indeed, the human immune system generates a strong response to specific polysaccharide surface structures of bacteria, such as O-antigens and capsular polysaccharides. However, since the immune response to polysaccharides is IgM dependent, the immune system develops no memory. The protein carrier that carries the polysaccharide triggers an IgG response that is T-cell dependent and that provides long lasting protection since the immune system develops memory.

*E. coli* O157 is an enterohemorrhagic strain responsible for approximately two-thirds of all recent cases of hemolytic-uremic syndrome and poses serious human health concerns (Law, D. (2000) *J. App. Microbiol.*, 88, 729-745; Wang, L., and Reeves, P. R. (1998) Infect. Immun. 66, 3545-3551).

*Escherichia coli* strain O157 produces an O-antigen containing the repeating tetrasaccharide unit (4-N-acetyl perosamine→fucose→glucose→GalNAc) (α-D-PerNAc-α-L-Fuc-β-D-Glc-α-D-GalNAc) (Perry, M. B., MacLean, L. and Griffith, D. W. (1986) *Biochem. Cell. Biol.*, 64, 21-28). The tetrasaccharide is preassembled on undecaprenyl pyrophosphate. The *E. coli* cell envelope contains an inner plasma membrane, a stress-bearing peptidoglycan layer and an asymmetric outer membrane consisting of a phospholipid inner monolayer and an outer monolayer composed of bacterial LPS. LPS contains three components, the lipid A anchor, the 3-deoxy-D-manno-oct-2-ulosonic acid-containing core, and the O-antigen region (see: Raetz, C. R. H. and Whitfield, C. (2002) *Annu. Rev. Biochem.*, 71, 635-700; Whitfield, C. (2006) *Ann. Rev. Biochem.* 75, 39-68; Samuel, G. and Reeves, P. R. (2003) *Carbohydrate Research*, 338, 2503-2519; and refs. therein for reviews on the assembly of O-antigens of bacterial LPS).

The O-antigen components of bacterial LPS are large, extremely diverse polysaccharides that can be either homopolymeric, composed of a single repeating monosaccharide, or heteropolymeric, containing 10-30 repeats of 3-6 sugar units (Reeves, P. R., Hobbs, M., Valvano, M. A., Skurnik, M., Whitfield, C., Coplin, D., Kido, N., Klena, J., Maskell, D., Raetz, C. R. H., and Rick, P. D. (1996) *Trends Microbiol.*, 4, 495-503). O-antigens are, thus, the dominant feature of the bacterial cell surface and constitute important determinants of virulence and pathogenicity (Law, D. (2000) *J. App. Microbiol.*, 88, 729-745; Spears, K. J., Roe, A. J. and Gally, D. L. (2006) *FEMS Microbiol. Lett.*, 255, 187-202; Liu, B., Knirel, Y. A., Feng, L., Perepelov, A. V., Senchenkova, S. N., Wang, Q., Reeves, P. R. and Wang, L (2008) *FEMS Microbiol. Rev.* 32, 627-653; Stenutz, R., Weintraub, A. and Widmalm, G. (2006) *FEMS Microbiol. Rev.* 30, 382-403). *E. coli* strains with more than 180 individual O-serotypes, attributed to unique O-antigen structures, have been identified (Stenutz, R., Weintraub, A. and Widmalm, G. (2006) *FEMS Microbiol. Rev.* 30, 382-403).

O-antigen repeat units are pre-assembled on the cytosolic face of the inner membrane attached to undecaprenyl pyrophosphate. The lipid-linked repeat units diffuse transversely (flip-flop) to the periplasmic surface of the inner membrane and are polymerized before transport to the outer membrane and ligation to LPS. Most heteropolymeric O-antigen repeat units have either N-acetylglucosamine ("GlcNAc") or N-acetylgalactosamine ("GalNAc") at the reducing terminus.

It had been assumed that the biosynthesis of the lipid intermediates is initiated by the transfer of GlcNAc-P or GalNAc-P from their respective sugar nucleotide derivatives to undecaprenyl monophosphate ("Und-P") catalyzed by WecA (Samuel, G. and Reeves, P. R. (2003) *Carbohydrate Research*, 338, 2503-2519; Alexander, D. C. and Valvano, M. A. (1994) *J. Bacteriol.*, 176, 7079-7084; Zhang, L., Radziejewska-Lebrecht, J., Krajewska-Pietrasik, D., Tolvanen, P. and Skurkik, M. (1997) *Mol. Microbiol.* 23, 63-76; Amor, P. A. and Whitfield, C. (1997) *Mol. Microbiol.* 26 (145-161); Wang, L. and Reeves, P. R. (1998) *Infect. Immun.* 66, 3545-3551). Although the properties and specificity of the GlcNAc-phosphotransferase activity of WecA have been characterized (Rush, J. S., Rick, P. D. and Waechter, C. J. (1997) Glycobiology, 7, 315-322), the conclusion that WecA catalyzes the synthesis of GalNAc-P-P-Und was based on genetic studies (Wang, L. and Reeves, P. R. (1998) *Infect. Immun.* 66, 3545-3551). Such earlier genetic studies indicated that the biosynthesis of the lipid-linked tetrasaccharide intermediate was initiated by the enzymatic transfer of GalNAc-P from UDP-GalNAc to Und-P catalyzed by WecA (Wang, L. and Reeves, P. R. (1998) *Infect. Immun.* 66, 3545-3551). However, there was no direct enzymological evidence demonstrating that WecA utilizes UDP-GalNAc as a GalNAc-P donor.

Furthermore, the *E. coli* O55 gne and gne1 genes were previously proposed to encode a UDP-GlcNAc 4-epimerase (Wang, L., Huskic, S., Cisterne, A., Rothemund, D. and Reeves, P. R. (2002) *J. Bacteriol.* 184, 2620-2625; Guo, H., Yi, W., Li, L. and Wang, P. G. (2007) *Biochem. Biophys. Res. Commun.*, 356, 604-609). Previous reports identified two genes from *E. coli* O55 (Wang, L., Huskic, S., Cisterne, A., Rothemund, D. and Reeves, P. R. (2002) *J. Bacteriol.* 184, 2620-2625) and *E. coli* O86 (Guo, H., Yi, W., Li, L. and Wang, P. G. (2007) *Biochem. Biophys. Res. Commun.*, 356, 604-609), *E. coli* O55 gne and *E. coli* O86 gne1, respectively, that are 100% identical to a Z3206 gene within the same gene family.

Accordingly, one of skill would have been led to believe that the Z3206 gene also encodes a UDP-GlcNAc/UDP-GalNAc epimerase.

BRIEF SUMMARY OF THE INVENTION

It has now been surprisingly discovered that an epimerase encoded by the Z3206 gene in *E. coli* O157 catalyzes a reaction that synthesizes N-acetylgalactosamine ("GalNAc") on undecaprenyl pyrophosphate, which initiates the formation of an oligo- or polysaccharide.

In one aspect, the present invention relates to a recombinant prokaryotic biosynthetic system that produces all or a portion of a polysaccharide comprising an epimerase that synthesizes GalNAc on undecaprenyl pyrophosphate. The invention further includes glycosyltransferases that synthesize all or a portion of a polysaccharide having GalNAc at the reducing terminus, and still further includes glycosyltransferases that synthesize all or a portion of an antigenic polysaccharide having GalNAc at the reducing terminus.

In another aspect, the invention is directed to an epimerase to produce GalNAc on undecaprenyl pyrophosphate, and, in a further aspect, the epimerase is encoded by the Z3206 gene.

In an additional aspect, the present invention is directed to an expression system for producing an N-glycosylated protein comprising: a nucleotide sequence encoding an oligosaccharyl transferase; a nucleotide sequence encoding a protein carrier; at least one oligo- or polysaccharide gene cluster from at least one bacterium, wherein the polysaccharide contains GalNAc at the reducing terminus; and a nucleic acid sequence encoding an epimerase.

In a still further aspect, the instant invention is directed to a recombinant prokaryotic biosynthetic system comprising Z3206 gene which encodes an epimerase that converts GlcNAc-P-P-Und to GalNAc-P-P-Und.

In yet an additional aspect, the present invention is directed to a recombinant prokaryotic biosynthetic system comprising E. coli O55 gne gene or E. coli O86 gne1 gene which encodes an epimerase that converts GlcNAc-P-P-Und to GalNAc-P-P-Und.

In yet another aspect, the present invention relates to an N-glycosylated protein comprising at least one introduced consensus sequence, D/E-X-N-Z-S/T(SEQ ID NO:31), wherein X and Z can be any natural amino acid except proline, and a glycan having N-acetylgalactosamine at the reducing terminus.

In still another aspect, the present invention is directed to a bioconjugate vaccine comprising an N-glycosylated protein having at least one introduced consensus sequence, D/E-X-N-Z-S/T (SEQ ID NO:31), wherein X and Z can be any natural amino acid except proline; an immunogenic glycan having N-acetylgalactosamine at the reducing terminus; and an adjuvant.

In an addition aspect, the invention relates to method for producing an N-linked glycosylated protein in a host cell comprising nucleic acids encoding: glycosyltransferases that assemble at least one oligo- or polysaccharide from at least one bacterium containing GalNAc at the reducing terminus; a protein carrier; an oligosaccharyl transferase; and an epimerase.

In a further aspect, the present invention relates to the use of a biosynthetic system and proteins for preparing a bioconjugate vaccine.

In an additional aspect, the present invention is directed to methods for producing mono-, oligo- and polysaccharides, and in a still further aspect the invention directed to methods for producing antigenic glycans and N-glycosylated proteins.

BRIEF DESCRIPTION OF THE DRAWINGS

FIG. 3 shows purification and characterization of [$^3$H] GalNAc-P-P-Und synthesized by membrane fractions from E. coli strain O157. Membrane fractions from E. coli O157 were incubated with UDP-[$^3$H]GlcNAc, and the [$^3$H]GalNAc lipids were purified as described in Example 3.

DETAILED DESCRIPTION OF THE INVENTION

Figure 1:
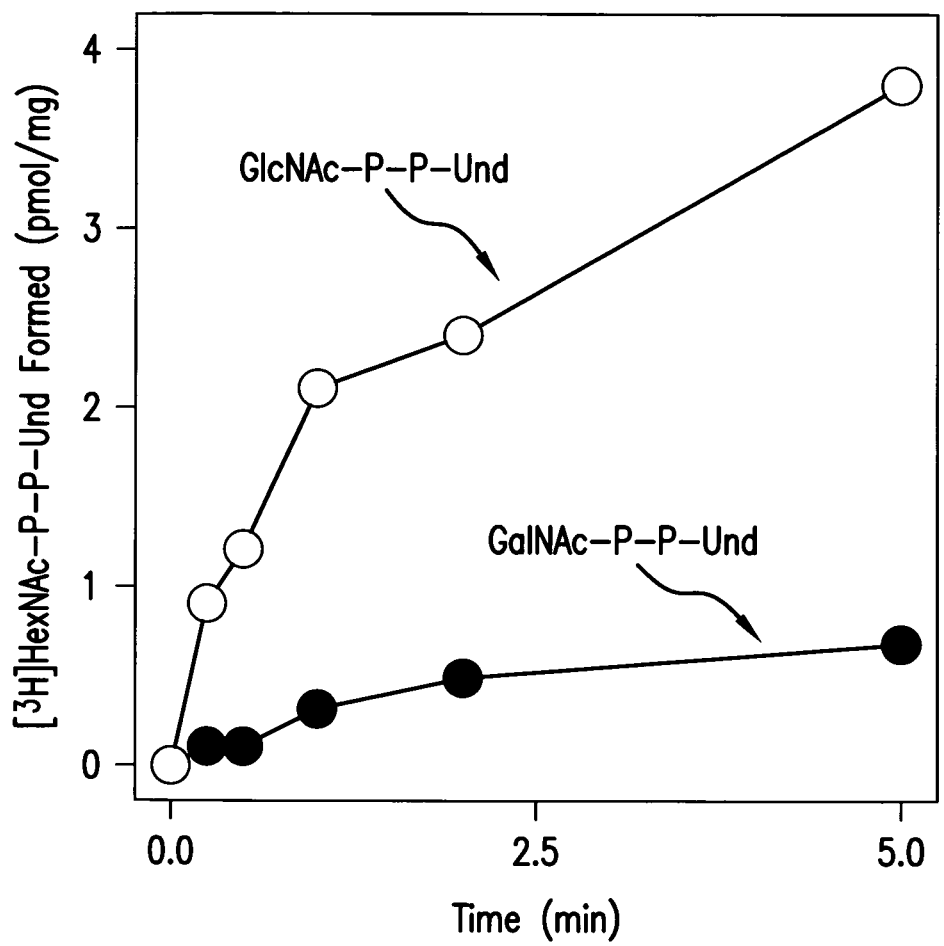
FIG. 1 shows the time course of [$^3$H]GlcNAc/GalNAc-P-P-Und synthesis by membrane fractions from E. coli O157. The membrane fraction from E. coli strain O157 was incubated with UDP-[$^3$H]GlcNAc for the indicated times at 37° C. The [$^3$H]lipid products were extracted and the incorporation of [$^3$H]GlcNAc into [$^3$H]GlcNAc-P-P-Und (O) and [$^3$H]GalNAc-P-P-Und (●) was assayed as described in Example 2.

The present invention encompasses a recombinant prokaryotic biosynthetic system comprising nucleic acids encoding an epimerase that synthesizes an oligo- or polysaccharide having N-acetylgalactosamine at the reducing terminus, and N-glycosylated proteins having N-acetylgalactosamine at the reducing terminus of the glycan.

The term "partial amino acid sequence(s)" is also referred to as "optimized consensus sequence(s)" or "consensus sequence(s)." The optimized consensus sequence is N-glycosylated by an oligosaccharyl transferase ("OST," "OTase"), much more efficiently than the regular consensus sequence "N-X-S/T."

In general, the term "recombinant N-glycosylated protein" refers to any poly- or oligopeptide produced in a host cell that does not naturally comprise the nucleic acid encoding said protein. In the context of the present invention, this term refers to a protein produced recombinantly in a prokaryotic host cell, for example, *Escherichia* spp., *Campylobacter* spp., *Salmonella* spp., *Shigella* spp., *Helicobacter* spp., *Pseudomonas* spp., *Bacillus* spp., and in further embodiments *Escherichia coli*, *Campylobacter jejuni*, *Salmonella typhimurium* etc., wherein the nucleic acid encoding said protein has been introduced into said host cell and wherein the encoded protein is N-glycosylated by the OTase, said transferase enzyme naturally occurring in or being introduced recombinantly into said host cell.

In accordance with the internationally accepted one letter code for amino acids the abbreviations D, E, N, S and T denote aspartic acid, glutamic acid, asparagine, serine, and threonine, respectively.

Proteins according to the invention comprise one or more of an optimized consensus sequence(s) D/E-X-N-Z-S/T (SEQ ID NO:31) that is/are introduced into the protein and N-glycosylated. Hence, the proteins of the present invention differ from the naturally occurring *C. jejuni* N-glycoproteins which also contain the optimized consensus sequence but do not comprise any additional (introduced) optimized consensus sequences.

The introduction of the optimized consensus sequence can be accomplished by the addition, deletion and/or substitution of one or more amino acids. The addition, deletion and/or substitution of one or more amino acids for the purpose of introducing the optimized consensus sequence can be accomplished by chemical synthetic strategies, which, in view of the instant invention, would be well known to those skilled in the art such as solid phase-assisted chemical peptide synthesis.

Alternatively, and preferred for larger polypeptides, the proteins of the present invention can be prepared by recombinant techniques that would be art-standard techniques in light of the invention.

The proteins of the present invention have the advantage that they may be produced with high efficiency and in any host. In one embodiment of the invention, the host comprises a functional pgl operon from *Campylobacter* spp., for example, from *C. jejuni*. In further embodiments, oligosaccharyl transferases from *Campylobacter* spp. for practicing the invention are from *Campylobacter coli* or *Campylobacter lari*. In view of the invention, oligosaccharyl transferases would be apparent to one of skill in the art. For example, oligosaccharyl transferases are disclosed in references such as Szymanski, C. M. and Wren, B. W. (2005) Protein glycosylation in bacterial mucosal pathogens, Nat. Rev. Microbiol. 3:225-237. The functional pgl operon may be present naturally when said prokaryotic host is *Campylobacter* spp., or, for example, *C. jejuni*. However, as demonstrated before in the art and mentioned above, the pgl operon can be transferred into cells and remain functional in said new cellular environment.

The term "functional pgl operon from *Campylobacter* spp., preferably *C. jejuni*" is meant to refer to the cluster of nucleic acids encoding the functional oligosaccharyl transferase (OTase) of *Campylobacter* spp., for example, *C. jejuni*, and one or more specific glycosyltransferases capable of assembling an oligosaccharide on a lipid carrier, and wherein said oligosaccharide can be transferred from the lipid carrier to the target protein having one or more optimized amino acid sequence(s): D/E-X N-Z-S/T (SEQ ID NO:31)by the OTase. It to be understood that the term "functional pgl operon from *Campylobacter* spp., preferably *C. jejuni*" in the context of this invention does not necessarily refer to an operon as a singular transcriptional unit. The term merely requires the presence of the functional components for N-glycosylation of the recombinant protein in one host cell. These components may be transcribed as one or more separate mRNAs and may be regulated together or separately. For example, the term also encompasses functional components positioned in genomic DNA and plasmid(s) in one host cell. For the purpose of efficiency, in one embodiment all components of the functional pgl operon are regulated and expressed simultaneously.

The oligosaccharyl transferase can originate, in some embodiments, from *Campylobacter* spp., and in other embodiments, from *C. jejuni*. In additional embodiments, the oligosaccharyl transferase can originate from other organisms which are known to those of skill in the art as having an oligosaccharyl transferase, such as, for example, *Wolinella* spp. and eukaryotic organisms.

The one or more specific glycosyltransferases capable of assembling an oligosaccharide on a lipid carrier may originate from the host cell or be introduced recombinantly into said host cell, the only functional limitation being that the oligosaccharide assembled by said glycosyltransferases can be transferred from the lipid carrier to the target protein having one or more optimized consensus sequences by the OTase. Hence, the selection of the host cell comprising specific glycosyltransferases naturally and/or replacing specific glycosyltransferases naturally present in said host as well as the introduction of heterologous specific glycosyltransferases will enable those skilled in the art to vary the N-glycans bound to the optimized N-glycosylation consensus site in the proteins of the present invention.

As a result of the above, the present invention provides for the individual design of N-glycan-patterns on the proteins of the present invention. The proteins can therefore be individualized in their N-glycan pattern to suit biological, pharmaceutical and purification needs.

In embodiments of the present invention, the proteins may comprise one but also more than one, such as at least two, at least 3 or at least 5 of said N-glycosylated optimized amino acid sequences.

The presence of one or more N-glycosylated optimized amino acid sequence(s) in the proteins of the present invention can be of advantage for increasing their immunogenicity, increasing their stability, affecting their biological activity, prolonging their biological half-life and/or simplifying their purification.

The optimized consensus sequence may include any amino acid except proline in position(s) X and Z. The term "any amino acids" is meant to encompass common and rare natural amino acids as well as synthetic amino acid derivatives and analogs that will still allow the optimized consensus sequence to be N-glycosylated by the OTase. Naturally occurring common and rare amino acids are preferred for X and Z. X and Z may be the same or different.

It is noted that X and Z may differ for each optimized consensus sequence in a protein according to the present invention.

The N-glycan bound to the optimized consensus sequence will be determined by the specific glycosyltransferases and their interaction when assembling the oligosaccharide on a lipid carrier for transfer by the OTase. In view of the instant invention, those skilled in the art would be able to design the N-glycan by varying the type(s) and amount of the specific glycosyltransferases present in the desired host cell.

"Monosaccharide" as used herein refers to one sugar residue. "Oligo- and polysaccharide" refer to two or more sugar residues. The term "glycans" as used herein refers to mono-, oligo- or polysaccharides. "N-glycans" are defined herein as mono-, oligo- or polysaccharides of variable compositions that are linked to an ε-amide nitrogen of an asparagine residue in a protein via an N-glycosidic linkage. In an embodiment, the N-glycans transferred by the OTase are assembled on an undecaprenol pyrophosphate ("Und-P-P") lipid-anchor that is present in the cytoplasmic membrane of gram-negative or positive bacteria. They are involved in the synthesis of O antigen, O polysaccharide and peptidoglycan (Bugg, T. D., and Brandish, P. E. (1994). From peptidoglycan to glycoproteins: common features of lipid-linked oligosaccharide biosynthesis. FEMS Microbiol Lett 119, 255-262; Valvano, M. A. (2003). Export of O-specific lipopolysaccharide. Front Biosci 8, s452-471).

Studies were conducted to determine whether the biosynthesis of a lipid-linked repeating tetrasaccharide (4-N-acetyl perosamine→fucose→glucose→GalNAc) was initiated by the formation of GalNAc-P-P-Und by WecA. When membrane fractions from E. coli strains K12, O157, and PR4019, a WecA-overexpressing strain, were incubated with UDP-[$^3$H]GalNAc, neither the enzymatic synthesis of [$^3$H]GlcNAc-P-P-Und nor [$^3$H]GalNAc-P-P-Und was detected. However, when membrane fractions from strain O157 were incubated with UDP-[$^3$H]GlcNAc, two enzymatically labeled products were observed with the chemical and chromatographic properties of [$^3$H]GlcNAc-P-P-Und and [$^3$H]GalNAc-P-P-Und, confirming that strain O157 contained an epimerase capable of interconverting GlcNAc-P-P-Und and GalNAc-P-P-Und. The presence of an epimerase was also confirmed by showing that exogenous [$^3$H]GlcNAc-P-P-Und was converted to [$^3$H]GalNAc-P-P-Und when incubated with membranes from strain O157. When strain O157 was metabolically labeled with [$^3$H]GlcNAc, both [$^3$H]GlcNAc-P-P-Und and [$^3$H]GalNAc-P-P-Und were detected. Transformation of E. coli strain 21546 with the Z3206 gene enabled these cells to synthesize GalNAc-P-P-Und in vivo and in vitro. The reversibility of the epimerase reaction was demonstrated by showing that [$^3$H]GlcNAc-P-P-Und was reformed when membranes from strain O157 were incubated with exogenous [$^3$H]GalNAc-P-P-Und. The inability of Z3206 to complement the loss of the gne gene in the expression of the Campylobacter jejuni N-glycosylation system in E. coli indicated that it does not function as a UDP-GlcNAc/UDP-GalNAc epimerase. Based on these results, it was confirmed that GalNAc-P-P-Und is synthesized reversibly by a GlcNAc-P-P-Und epimerase following the formation of GlcNAc-P-P-Und by WecA in E. coli O157.

The initiating reaction of E. coli O157 O-antigen subunit assembly was investigated to confirm that GalNAc-P-P-Und synthesis is catalyzed by some previously unknown mechanism rather than by WecA. The evidence presented herein shows that GalNAc-P-P-Und is not synthesized by GalNAc-P transfer from UDP-GalNAc catalyzed by WecA but rather by the reversible epimerization of the 4-OH of GlcNAc-P-P-Und catalyzed by an epimerase encoded by the Z3206 gene in E. coli O157.

Accordingly, the invention encompasses a novel biosynthetic pathway for the assembly of an important bacterial cell surface component as well as a new biosynthetic route for the synthesis of GalNAc-P-P-Und. A further embodiment of the invention includes the bacterial epimerase as a new target for antimicrobial agents.

E. coli O157 synthesizes an O-antigen with the repeating tetrasaccharide structure (4-N-acetyl perosamine→fucose→glucose→GalNAc). It is shown herein that the biosynthesis of the lipid-linked tetrasaccharide intermediate was not initiated by the enzymatic transfer of GalNAc-P from UDP-GalNAc to Und-P catalyzed by WecA, contrary to earlier genetic studies (Wang, L. and Reeves, P. R. (1998) Infect. Immun. 66, 3545-3551). The invention described herein, obtained by homology searches and then confirmed by results from genetic, enzymology, and metabolic labeling experiments, demonstrates that WecA does not utilize UDP-GalNAc as a substrate, but that WecA is required to synthesize GlcNAc-P-P-Und which is then reversibly converted to GalNAc-P-P-Und by an epimerase encoded by the Z3206 gene in strain O157.

The Z3206 gene of the present invention belongs to a family of genes present in several strains that produce surface O-antigen repeat units containing GalNAc residues at their reducing termini (Table 1). The Z3206 gene sequence is shown in SEQ ID NO: 1. Previous reports identified two genes from E. coli O55 (Wang, L., Huskic, S., Cisterne, A., Rothemund, D. and Reeves, P. R. (2002) J. Bacteriol. 184, 2620-2625) and E. coli O86 (Guo, H., Yi, W., Li, L. and Wang, P. G. (2007) Biochem. Biophys. Res. Comm., 356, 604-609), E. coli O55 gne and E. coli O86 gne1, respectively, that are 100% identical to a Z3206 gene (Table 1). The E. coli O55 gne gene sequence is shown as SEQ ID NO: 3, and E. coli O86 gne1 gene sequence is shown as SEQ ID NO: 5.

TABLE 1

Correlation of Z3206 gene in bacterial strains expressing O-antigen chains with GalNAc at the reducing termini.

| | % Identity with Z3206 | GalNAc at the reducing terminus of O-antigen repeat unit |
|---|---|---|
| E. coli O55 gne (SEQ ID NO: 3) | 100 | Yes |
| E. coli O86 gne1 (SEQ ID NO: 5) | 100 | Yes |
| Shigella boydii O18 gne (SEQ ID NO: 7) | 88 | Yes |

TABLE 1-continued

Correlation of Z3206 gene in bacterial strains expressing O-antigen chains with GalNAc at the reducing termini.

| | % Identity with Z3206 | GalNAc at the reducing terminus of O-antigen repeat unit |
|---|---|---|
| *Salmonella enterica* O30 gne (SEQ ID NO: 9) | 94 | Yes |
| *C. jejuni* gne (SEQ ID NO: 11) | 21 | No |
| *E. coli* K12 galE (SEQ ID NO: 13) | 27 | No |
| *E. coli* O86 gne2 (SEQ ID NO: 15) | 18 | Yes |

Accordingly, we conclude that *E. coli* O55 gne and *E. coli* O86 gne1 also encode epimerases capable of converting GlcNAc-P-P-Und to GalNAc-P-P-Und P-Und in strains O55 and O86, respectively, which also produce O-antigen repeat units with GalNAc at the reducing termini (Table 1).

Figure 8:
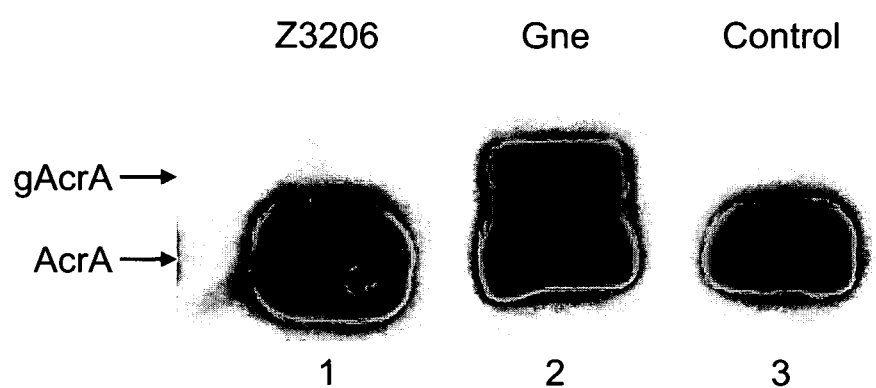
FIG. 8 shows SDS-PAGE analysis of unglycosylated and glycosylated AcrA protein. Periplasmic extracts prepared from E. coli DH5α cells carrying the AcrA expression plasmid and the pgl operon Δgne complemented with pMLBAD: Z3206 (lane 1), pMLBAD:gne (lane 2) or the vector control pMLBAD (lane 3) were separated by 10% SDS-PAGE and transferred to nitrocellulose membranes. AcrA and its glycosylated forms were detected with anti AcrA antisera. The position of bands corresponding to unglycosylated (AcrA) and glycosylated AcrA (gAcrA) is indicated.

Two experimental approaches in this study indicate that the Z3206 protein does not catalyze the epimerization of UDP-GlcNAc to UDP-GalNAc in strain O157. First, when membranes from strain O157 were incubated with [$^3$H]UDP-GalNAc, neither [$^3$H]GlcNAc-P-P-Und nor [$^3$H]GalNAc-P-P-Und was detected (Table 3). If Z3206 catalyzed the conversion of [$^3$H]UDP-GalNAc to [$^3$H]UDP-GlcNAc, it would be expected that [$^3$H]GlcNAc-P-P-Und should be observed. Second, we have shown that hemagglutinin-tagged Z3206 was incapable of complementing the UDP-GalNAc-dependent *C. jejuni* N-glycosylation reporter system (FIG. 8).

*E. coli* O55 gne gene from strain O55 (Wang, L., Huskic, S., Cisterne, A., Rothemund, D. and Reeves, P. R. (2002) J. Bacteriol. 184, 2620-2625) was also assayed for epimerase activity by incubating crude extracts with UDP-GalNAc and indirectly assaying the conversion to UDP-GlcNAc by measuring an increase in reactivity with p-dimethylaminobenzaldehyde after acid hydrolysis. In both studies, the formation of the product was based on changes in reactivity with p-dimethylaminobenzaldehyde, and not a definitive characterization of the sugar nucleotide end product. A 90% pure poly-histidine-tagged *E. coli* O86 gne1 was also shown to have a low level of UDP-glucose epimerase activity relative to Gne2 in a coupled assay.

Accordingly, an embodiment of the invention is directed to a recombinant prokaryotic biosynthetic system containing Z3206 gene, *E. coli* O55 gne gene or *E. coli* O86 gne1 gene that converts GlcNAc-P-P-Und to GalNAc-P-P-Und.

It is significant that *E. coli* O86, which synthesizes an O-antigen containing two GalNAc residues, which would presumably require UDP-GalNAc as the glycosyl donor for the additional, non-reducing terminal GalNAc, also possesses an additional GlcNAc 4-epimerase gene, termed gne2, within the O-antigen gene cluster (Guo, H., Yi, W., Li, L. and Wang, P. G. (2007) *Biochem. Biophys. Res. Commun.*, 356, 604-609). This additional epimerase gene has high homology with the galE gene of the colanic acid gene cluster and appears to be a UDP-GlcNAc 4-epimerase capable of synthesizing UDP-GalNAc.

The Z3206 gene appears to be highly conserved in *E. coli* O-serotypes initiated with GalNAc. In a recent study, 62 *E. coli* strains, with established O-antigen repeat unit structures, were screened for expression of Z3206 by a polymerase chain reaction based method using nucleotide primers designed to specifically detect the *E. coli* O157 Z3206 gene (Wang, L., Huskic, S., Cisterne, A., Rothemund, D. and Reeves, P. R. (2002) J. Bacteriol. 184, 2620-2625). In this study Z3206 was detected in 16 of the 22 *E. coli* strains that were known to contain GalNAc, and in only 4 of the 40 strains lacking GalNAc. Moreover, a similar screen of the 22 GalNAc-containing strains with primers designed to detect an alternative epimerase with UDP-GlcNAc 4-epimerase activity (the GalE gene of *E. coli* O113) detected no strains carrying this gene, indicating that Z3206 is the GlcNAc 4-epimerase gene most commonly associated with the presence of a reducing-terminal GalNAc in O-antigen repeat units of *E. coli*.

Analysis of the Z3206 protein sequence by a variety of web-based topological prediction algorithms indicates that the Z3206 protein is not highly hydrophobic. The majority of the topological prediction algorithms indicate that Z3206 is a soluble 37 kDa protein, although TMPred (Hofmann, K., and Stoffel, W. (1993) Biol. Chem. Hoppe-Seyler 374, 166 (abstr.)) predicted a single weak N-terminal transmembrane helix. However, Western blotting after SDS-PAGE of cellular fractions from *E. coli* cells expressing hemagglutinin-tagged Z3206 clearly shows that the tagged protein is associated with the particulate fraction following hypotonic lysis of the cells. Preliminary experiments show that the protein remains associated with the particulate fraction following incubation of the membrane fraction with 1 M KCl, but is solubilized in an active form by incubation with 0.1% Triton X-100.

*E. coli* O157 Z3206 has significant sequence homology with the short-chain dehydrogenase/reductase family of oxido-reductases including the GXXGXXG motif (Rossman fold), consistent with the NAD(P) binding pocket (Allard, S. T. M., Giraud, M. F., and Naismith, J. H. (2001) Cell. Mol. Life Sci. 58, 1650-1655) and the conserved S $X_{24}YX_3K$ sequence, involved in proton abstraction and donation (Field, R. A. and Naismith, J. H. (2003) *Biochemistry* 42, 7637-7647). Molecular modeling based on crystal structures of UDP-Glc 4-epimerase, another member of the short-chain dehydrogenase/reductase family, suggests that, after hydride abstraction, the 4-keto intermediate rotates around the β phosphate of UDP to present the opposite face of the keto intermediate and allow re-insertion of hydride from the opposite side, thus inverting the configuration of the hydroxyl at carbon 4. The presence of these conserved sequences suggests that Z3206 likely functions via a similar mechanism. Although the equilibrium distribution of the epimerase products, seen in FIG. 7, seems to favor the formation of GlcNAc-P-P-Und, the utilization of GalNAc-P-P-Und for O-antigen repeat unit assembly would drive the epimerization reaction in the direction of GalNAc-P-P-Und by mass action.

Epimerization of the glycosyl moieties of polyisoprenoid lipid intermediates has not been widely reported in nature. In one previous study the 2-epimerization of ribosyl-P-decaprenol to form arabinosyl-P-decaprenol, an arabinosyl donor in arabinogalactan biosynthesis in mycobacteria, was reported (Mikusová, K., Huang, H., Yagi, T., Holsters, M., Vereecke, D., D'Haeze, W., Scherman, M. S., Brennan, P. J., McNeil, M. R., and Crick, D. C. (2005) *J. Bacteriol.* 187, 8020-8025). Arabinosyl-P-decaprenol is formed via a two-step oxidation/reduction reaction requiring two mycobacterial proteins, Rv3790 and Rv3791. Although epimerization was modestly stimulated by the addition of NAD and NADP, neither Rv3790 nor Rv3791 contain either the Rossman fold or the $SX_{24}YXXXK$ motif, characteristic of the short-chain dehydrogenase/reductase family (Allard, S. T. M., Giraud, M.-F. and Naismith, J. H. (2001) *Cell. Mol. Life Sci.* 58, 1650-1655; Field, R. A. and Naismith, J. H. (2003) *Biochemistry* 42, 7637-7647).

In summary, a novel biosynthetic pathway for the formation of GalNAc-P-P-Und by the epimerization of GlcNAc-P-P-Und, is described.

Several antibiotics have been shown to inhibit the synthesis of GlcNAc-P-P-Und, but are limited in their utility because they also block the synthesis of GlcNAc-P-P-dolichol, the initiating dolichol-linked intermediate of the protein N-glycosylation pathway. Although GlcNAc-P-P-dolichol is a structurally related mammalian counterpart of the bacterial glycolipid intermediate, GlcNAc-P-P-Und, there is no evidence for a similar epimerization reaction converting GlcNAc-P-P-dolichol to GalNAc-P-P-dolichol in eukaryotic cells. Thus, this raises the possibility that in strains where the surface O-antigen containing GalNAc at the reducing termini are involved in a pathological process, O-antigen synthesis could potentially be blocked by inhibiting the bacterial epimerases.

An embodiment of the present invention involves an epimerase that converts GlcNAc-P-P-Und (N-acetylglucosaminylpyrophosphorylundecaprenol) to GalNAc-P-P-Und (N-acetylgalactosaminylpyrophosphorylundecaprenol) in *E. coli* O157. A still further exemplary aspect of the invention involves the initiation of synthesis of lipid-bound repeating tetrasaccharide having GalNAc at the reducing terminus.

The basis of another aspect of the invention includes the discovery that *Campylobacter jejuni* contains a general N-linked protein glycosylation system. Various proteins of *C. jejuni* have been shown to be modified by a heptasaccharide. This heptasaccharide is assembled on undecaprenyl pyrophosphate, the carrier lipid, at the cytoplasmic side of the inner membrane by the stepwise addition of nucleotide activated monosaccharides catalyzed by specific glycosyltransferases. The lipid-linked oligosaccharide then flip-flops (diffuses transversely) into the periplasmic space by a flipppase, e.g., PglK. In the final step of N-linked protein glycosylation, the oligosaccharyltransferase (e.g., PglB) catalyzes the transfer of the oligosaccharide from the carrier lipid to asparagine (Asn) residues within the consensus sequence D/E-X-N-Z-S/T (SEQ ID NO:31), where the X and Z can be any amino acid except Pro. The glycosylation cluster for the heptasaccharide had been successfully transferred into *E. coli* and N-linked glycoproteins of *Campylobacter* had been produced.

It had been demonstrated that PglB does not have a strict specificity for the lipid-linked sugar substrate. The antigenic polysaccharides assembled on undecaprenyl pyrophosphate are captured by PglB in the periplasm and transferred to a protein carrier (Feldman, 2005; Wacker, M., et al., Substrate specificity of bacterial oligosaccharyltransferase suggests a common transfer mechanism for the bacterial and eukaryotic systems. Proc Natl. Acad Sci USA, 2006. 103(18): p. 7088-93.) The enzyme will also transfer a diverse array of undecaprenyl pyrophosphate (UPP) linked oligosaccharides if they contain an N-acetylated hexosamine at the reducing terminus. The nucleotide sequence for pglB and the amino acid sequence for PglB are published at WO2009/104074.

Accordingly, one embodiment of the invention involves a recombinant N-glycosylated protein comprising: one or more of an introduced consensus sequence, D/E-X-N-Z-S/T (SEQ ID NO:31), wherein X and Z can be any natural amino acid except proline; and an oligo- or polysaccharide having N-acetylgalactosamine at the reducing terminus and N-linked to each of said one or more introduced consensus sequences by an N-glycosidic linkage.

In a further embodiment, the present invention is directed to a recombinant prokaryotic biosynthetic system for producing all or a portion of a polysaccharide comprising an epimerase that synthesizes N-acetylgalactosamine ("GalNAc") on undecaprenyl pyrophosphate. In a further embodiment, all or a portion of the polysaccharide is antigenic.

In another embodiment, the present invention is directed to a recombinant prokaryotic biosynthetic system comprising: an epimerase that synthesizes GalNAc on undecaprenyl pyrophosphate; and glycosyltransferases that synthesize a polysaccharide having GalNAc at the reducing terminus.

An embodiment of the invention further comprises a recombinant prokaryotic biosynthetic system comprising an epimerase that synthesizes GalNAc on undecaprenyl pyrophosphate and glycosyltransferases that synthesize a polysaccharide, wherein said polysaccharide has the following structure: α-D-PerNAc-α-L-Fuc-β-D-Glc-α-D-GalNAc; and wherein GalNAc is at the reducing terminus of said polysaccharide.

The recombinant prokaryotic biosynthetic system can produce mono-, oligo- or polysaccharides of various origins. Embodiments of the invention are directed to oligo- and polysaccharides of various origins. Such oligo- and polysaccharides can be of prokaryotic or eukaryotic origin. Oligo- or polysaccharides of prokaryotic origin may be from gram-negative or gram-positive bacteria. In one embodiment of the invention, the oligo- or polysaccharide is from *E. coli*. In a further aspect of the invention, said oligo- or polysaccharide is from *E. coli* O157. In another embodiment, said oligo- or polysaccharide comprises the following structure: α-D-PerNAc-α-L-Fuc-β-D-Glc-α-D-GalNAc. In a further embodiment of the invention, the oligo- or polysaccharide is from *Shigella flexneri*. In a still further embodiment, the oligo- or polysaccharide is from *Shigella flexneri* 6. In a still further aspect, said oligo- or polysaccharide comprises the following structure:

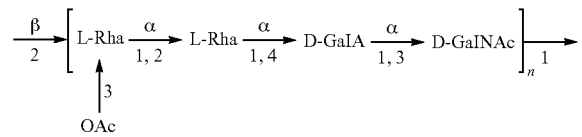

Embodiments of the invention further include proteins of various origins. Such proteins include proteins native to prokaryotic and eukaryotic organisms. The protein carrier can be, for example, AcrA or a protein carrier that has been modified to contain the consensus sequence for protein glycosylation, i.e., D/E-X-N-Z-S/T (SEQ ID No:31), wherein X and Z can be any amino acid except proline (e.g., a modified Exotoxin *Pseudomonas aeruginosa* ("EPA")). In one embodiment of the invention, the protein is *Pseudomonas aeruginosa* EPA.

A further aspect of the invention involves novel bioconjugate vaccines having GalNAc at the reducing terminus of the N-glycan. An additional embodiment of the invention involves a novel approach for producing such bioconjugate vaccines that uses recombinant bacterial cells that contain an epimerase which produces GalNAc on undecaprenyl pyrophosphate. In one embodiment, bioconjugate vaccines can be used to treat or prevent bacterial diseases. In further embodiments, bioconjugate vaccines may have therapeutic and/or prophylactic potential for cancer or other diseases.

A typical vaccination dosage for humans is about 1 to 25 μg, preferably about 1 μg to about 10 μg, most preferably about 10 μg. Optionally, a vaccine, such as a bioconjugate vaccine of the present invention, includes an adjuvant.

In an additional embodiment, the present invention is directed to an expression system for producing a bioconjugate vaccine against at least one bacterium comprising: a nucleotide sequence encoding an oligosaccharyl transferase; a nucleotide sequence encoding a protein carrier; at least one polysaccharide gene cluster from the at least one bacterium, wherein the polysaccharide contains GalNAc at the reducing terminus; and a nucleic acid sequence encoding an epimerase. In a further embodiment, the polysaccharide gene cluster encodes an antigenic polysaccharide.

In still a further embodiment, the present invention is directed to an expression system for producing a bioconjugate vaccine against at least one bacterium comprising: a nucleotide sequence encoding an oligosaccharyl transferase; a nucleotide sequence encoding a protein carrier comprising at least one inserted consensus sequence, D/E-X-N-Z-S/T (SEQ ID NO:31), wherein X and Z may be any natural amino acid except proline; at least one polysaccharide gene cluster from the at least one bacterium, wherein the polysaccharide contains GalNAc at the reducing terminus; and the Z3206 gene. In a further embodiment, the polysaccharide gene cluster encodes an antigenic polysaccharide.

In yet another embodiment, the present invention is directed to a bioconjugate vaccine comprising: a protein carrier; at least one immunogenic polysaccharide chain linked to the protein carrier, wherein said polysaccharide has GalNAc at the reducing terminus, and further wherein said GalNAc is directly linked to the protein carrier; and an adjuvant.

In yet an additional embodiment, the present invention is directed to a bioconjugate vaccine comprising: a protein carrier comprising at least one inserted consensus sequence, D/E-X-N-Z-S/T (SEQ ID NO:31), wherein X and Z may be any natural amino acid except proline; at least one immunogenic polysaccharide from at least one bacterium, linked to the protein carrier, wherein the at least one immunogenic polysaccharide contains GalNAc at the reducing terminus directly linked to the protein carrier; and, optionally, an adjuvant.

Another embodiment of the invention is directed to a method of producing a bioconjugate vaccine, said method comprising: assembling a polysaccharide having GalNAc at the reducing terminus in a recombinant organism through the use of glycosyltransferases; linking said GalNAc to an asparagine residue of one or more target proteins in said recombinant organism, wherein said one or more target proteins contain one or more T-cell epitopes.

In a further embodiment, the present invention is directed to a method of producing a bioconjugate vaccine, said method comprising: introducing genetic information encoding for a metabolic apparatus that carries out N-glycosylation of a target protein into a prokaryotic organism to produce a modified prokaryotic organism; wherein the genetic information required for the expression of one or more recombinant target proteins is introduced into said prokaryotic organism; wherein the genetic information required for the expression of E. coli strain O157 epimerase is introduced into said prokaryotic organism; and wherein the metabolic apparatus comprises glycosyltransferases of a type that assembles a polysaccharide having GalNAc at the reducing terminus on a lipid carrier, and an oligosaccharyltransferase, the oligosaccharyltransferase covalently linking GalNAc of the polysaccharide to an asparagine residue of the target protein, and the target protein containing at least one T-cell epitope; producing a culture of the modified prokaryotic organism; and obtaining glycosylated proteins from the culture medium.

A further aspect of the present invention relates to a pharmaceutical composition. An additional aspect of the invention involves a pharmaceutical composition comprising at least one N-glycosylated protein according to the invention. In light of the disclosure herein, the preparation of medicaments comprising proteins would be well known in the art. A still further aspect of the invention relates to a pharmaceutical composition comprising an antibiotic that inhibits an epimerase that converts GlcNAc-P-P-Und to GalNAc-P-P-Und. In a preferred embodiment, the pharmaceutical composition of the invention comprises a pharmaceutically acceptable excipient, diluent and/or adjuvant.

Suitable excipients, diluents and/or adjuvants are well-known in the art. An excipient or diluent may be a solid, semi-solid or liquid material which may serve as a vehicle or medium for the active ingredient. One of ordinary skill in the art in the field of preparing compositions can readily select the proper form and mode of administration depending upon the particular characteristics of the product selected, the disease or condition to be treated, the stage of the disease or condition, and other relevant circumstances (Remington's Pharmaceutical Sciences, Mack Publishing Co. (1990)). The proportion and nature of the pharmaceutically acceptable diluent or excipient are determined by the solubility and chemical properties of the pharmaceutically active compound selected, the chosen route of administration, and standard pharmaceutical practice. The pharmaceutical preparation may be adapted for oral, parenteral or topical use and may be administered to the patient in the form of tablets, capsules, suppositories, solution, suspensions, or the like. The pharmaceutically active compounds of the present invention, while effective themselves, can be formulated and administered in the form of their pharmaceutically acceptable salts, such as acid addition salts or base addition salts, for purposes of stability, convenience of crystallization, increased solubility, and the like.

In instances where specific nucleotide or amino acid sequences are noted, it will be understood that the present invention encompasses homologous sequences that still embody the same functionality as the noted sequences. In an embodiment of the invention, such sequences are at least 85% homologous. In another embodiment, such sequences are at least 90% homologous. In still further embodiments, such sequences are at least 95% homologous.

The determination of percent identity between two nucleotide or amino acid sequences is known to one of skill in the art.

Nucleic acid sequences described herein, such as those described in the sequence listing below, are examples only, and it will be apparent to one of skill in the art that the sequences can be combined in different ways. Additional embodiments of the invention include variants of nucleic acids. A variant of a nucleic acid (e.g., a codon-optimized nucleic acid) can be substantially identical, that is, at least 80% identical, for example, 80%, 85%, 90%, 91%, 92%, 93%, 94%, 95%, 96%, 97%, 98%, 99% or 99.5% identical, to SEQ ID NO: 1, SEQ ID NO: 3, SEQ ID NO: 5, SEQ ID NO: 7, SEQ ID NO: 9, SEQ ED NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 27, SEQ ID NO: 28 or SEQ ID NO: 29. Nucleic acid variants of a sequence that contains SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 27, SEQ ID NO: 28 or SEQ ID NO: 29 include nucleic acids with a substitution, variation, modification, replacement, deletion, and/or addition of one or more nucleotides (for example, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 125, 150, 175 or 200 nucleotides) from a sequence that contains SEQ ID NO: 1, SEQ ID NO: 3, SEQ ID NO: 5, SEQ ID NO: 7, SEQ ID NO: 9, SEQ ID NO: 11, SEQ NO: 13, SEQ ID NO: 15, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 27, SEQ ID NO: 28 or SEQ ID NO: 29, or parts thereof.

For example, in an embodiment of the instant invention, such variants include nucleic acids that encode an epimerase which converts GlcNAc-P-P-Und to GalNAc-P-P-Und and that i) are expressed in a host cell, such as, for example, E. coli and ii) are substantially identical to SEQ ID NO: 1, SEQ ID NO: 3, SEQ ID NO: 5, SEQ ID NO: 7 or SEQ ID NO: 9, or parts thereof.

Nucleic acids described herein include recombinant DNA and synthetic (e.g., chemically synthesized) DNA. Nucleic acids can be double-stranded or single-stranded. In the case of single-stranded nucleic acids, the nucleic acid can be a sense strand or antisense strand. Nucleic acids can be synthesized using oligonucleotide analogs or derivatives.

Plasmids that include a nucleic acid described herein can be transfected or transformed into host cells for expression. Techniques for transfection and transformation are known to those of skill in the art.

All publications mentioned herein are incorporated by reference in their entirety. It is to be understood that the term "or," as used herein, denotes alternatives that may, where appropriate, be combined; that is, the term "or" includes each listed alternative separately as well as their combination. As used herein, unless the context clearly dictates otherwise, references to the singular, such as the singular forms "a," "an," and "the," include the plural, and references to the plural include the singular.

The invention is further defined by reference to the following examples that further describe the compositions and methods of the present invention, as well as its utility. It will be apparent to those skilled in the art that modifications, both to compositions and methods, may be practiced which are within the scope of the invention.

EXAMPLES

Bacterial Strains and Plasmids—E. coli strains PR4019 (Rush, J. S., Rick, P. D. and Waechter, C. J. (1997) Glycobiology, 7, 315-322) and PR21546 (Meier-Dieter, U., Starman, R., Barr, K., Mayer, H. and Rick, P. D. (1990) J. Biol. Chem., 265, 13490-13497) were generous gifts from Dr. Paul Rick, Bethesda, Md., and E. coli O157:H45 (Stephan, R., Borel, N., Zweifel, C., Blanco, M., and Blanco, J. E. (2004) BMC Microbiol 4:10) was a gift from Dr. Claudio Zweifel, Veterinary Institute, University of Zurich. E. coli DH5α (Invitrogen) was used as the host for cloning experiments and for protein glycosylation analysis. Plasmids used are listed in Table 2.

TABLE 2

Plasmids used in Examples

| Plasmid | Description | Ref |
|---|---|---|
| pMLBAD | Cloning vector, $Tmp^R$ | Lefebre & Valvano (2002) |
| pMLBAD:Z3206 (SEQ ID NO: 23) | Z3206 in pMLBAD, $Tmp^R$, expression controlled by arabinose-inducible promoter | Examples herein |
| pMLBAD:gne (SEQ ID NO: 24) | gne in pMLBAD, $Tmp^R$, expression controlled by arabinose-inducible promoter | Examples herein |
| pACYCpgl | C. jejuni pgl cluster $Cm^R$ | Wacker, et al. (2002) |
| pACYCgne::kan | C. jejuni pgl cluster containing a kan cassette in gne, $Cm^R$, $Kan^R$ | Linton, et al. (2005) |
| pWA2 | Soluble periplasmic hexa-His-tagged AcrA under control of Tet promoter in pBR322, $Amp^R$ | Feldman, et al. (2005) |

Materials—[1,6-$^3$H]GlcNAc (30 Ci/mmol), UDP-[1-$^3$H]GlcNAc (20 Ci/mmol) and UDP-[6-$^3$H]GalNAc (20 Ci/mmol) were obtained from American Radiolabeled Chemicals (St. Louis, Mo.). Quantum 1 silica gel G thin layer plates are a product of Quantum Industries (Fairfield, N.J.), and Baker Si250 Silica Gel G plates are manufactured by Mallinckrodt Chemical Works. Yeast extract and Bacto-peptone were products of BD Biosciences. All other chemicals were obtained from standard commercial sources. Trimethoprim (50 μg/ml), chloramphenicol (20 μg/ml), ampicillin (100 μg/ml), and kanamycin (50 μg/ml) were added to the media as needed.

Construction of Recombinant Plasmids—E. coli strain DH5α was used for DNA cloning experiments and constructed plasmids were verified by DNA sequencing. The Z3206 gene was amplified from E. coli O157:H45 by PCR with oligonucleotides Z3206-Fw and Z3206-RvHA (AAA CCCGGGATGAACGATAACG TTTTGCTC (SEQ ID NO: 17) and AAATCTAGATTAAGCGTAATCTGGAACATC GTATGGGTACTCAGAAACAA ACGTTATGTC (SEQ ID NO: 18); restriction sites are underlined). The PCR fragment was digested with SmaI and XbaI and ligated into SmaI-XbaI cleaved pMLBAD vector (Lefebre, M. D. and Valvano M. A. (2002) Appl Environ Microbiol 68: 5956-5964). This resulted in plasmid pMLBAD:Z3206 (SEQ ID NO: 23) encoding Z3206 with a C-terminal hemagglutinin tag.

The gne gene was amplified from pACYCpgl (Wacker, M., Linton, D., Hitchen, P. G., Nita-Lazar, M., Haslam, S. M., North, S. J., Panico, M., Morris, H. R., Dell, A., Wrenn, B. W., Aebi, M. (2002) Science 298, 1790-1793), encoding Campylobacter jejuni pgl cluster, with oligonucleotides gne-Fw and gne-RV (AAACCATGGATGAAAATTCTTATTAGCGG (SEQ ID NO: 19) and AAATCTAGATTAAGCGTAATCTG GAACATCGTATGGGTAGCACTGTTTTTCCCAATC (SEQ ID NO: 20); restriction sites are underlined). The PCR product was digested with NcoI and XbaI and ligated into the same sites of pMLBAD to generate plasmid pMLBAD:gne (SEQ ID NO: 24) which encodes Gne with a C-terminal hemagglutinin tag (Table 2).

Growth Conditions, Protein Expression and Immunodetection—E. coli strains were cultured in Luria-Bertani medium (1% yeast extract, 2% Bacto-peptone, 0.6% NaCl) at 37° C. with vigorous shaking. Arabinose inducible expression was achieved by adding arabinose at a final concentration of 0.02-0.2% (w/v) to E. coli cells grown up to an $A_{600}$ of 0.05-0.4. The same amount of arabinose was added again 5 h post-induction, and incubation continued for 4-15 h.

Analytical Procedures—Protein concentrations were determined using the BCA protein assay (Pierce) after precipitation of membrane proteins with deoxycholate and trichloroacetic acid according to the Pierce Biotechnology bulletin "Eliminate Interfering Substances from Samples for BCA Protein Assay." Samples were analyzed for radioactivity by scintillation spectrometry in a Packard Tri-Carb 2100TR liquid scintillation spectrometer after the addition of 0.5 ml of 1% SDS and 4 ml of Econosafe Economical Biodegradable Counting Mixture (Research Products International, Corp., Mount Prospect, Ill.).

Example 1

Identification of an *E. coli* O157 Gene Encoding GlcNAc-P-P-Und 4-Epimerase

Figure 2:
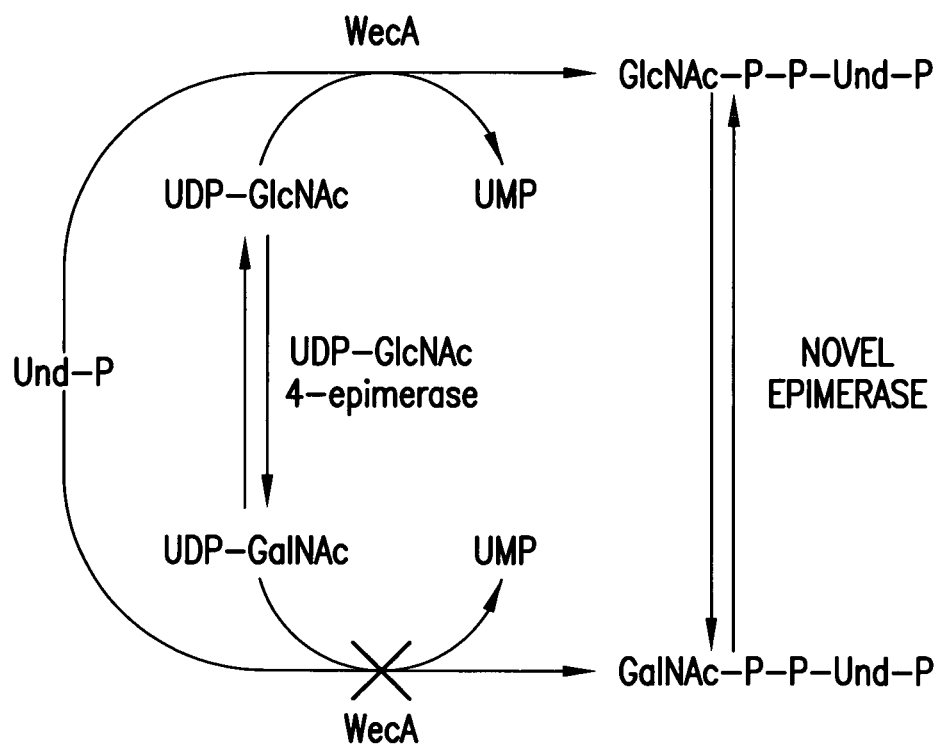
FIG. 2 shows the proposed biosynthetic pathway for the formation of GalNAc-P-P-Und from GlcNAc-P-P-Und.

We describe herein the surprising discovery of a new biosynthetic pathway in which GalNAc-P-P-Und is formed by the epimerization of the 4-OH of GlcNAc-P-P-Und catalyzed by the previously unknown action of a 4-epimerase. In this pathway, GlcNAc-P-P-Und is formed by the transfer of GlcNAc-P from UDP-GlcNAc, catalyzed by WecA, and then GlcNAc-P-P-Und is epimerized to GalNAc-P-P-Und by GlcNAc-P-P-Und -4-epimerase, which was a previously unknown pathway (FIG. 2).

The gene encoding a candidate for the GlcNAc-P-P-Und 4-epimerase was identified by DNA homology searches. Homology searches were performed using the U.S. National Library of Medicine databases found at http://blast.ncbi.nlm.nih.gov/Blast.cgi. Genomic sequences of different bacteria encoding O antigen repeating units having a GalNAc at the reducing terminus were screened. One group with a repeating unit containing a GalNAc at the reducing terminus, and a second group lacking a terminal GalNAc in the repeating unit were compared to identify potential epimerases. Using these criteria, Z3206 was identified as a candidate GlcNAc-P-P-Und 4-epimerase (Table 1).

The GlcNAc 4-epimerase genes present in *E. coli* strains with O-antigen repeat units containing GalNAc can be separated into two homology groups as shown in Table 1. It was surprisingly discovered that one homology group (containing gne1) clearly was correlated with the presence of GalNAc as the initiating sugar on the O-antigen repeat unit. It was further surprisingly discovered that the second group (containing gne2) exhibits a high degree of similarity to the UDP-Glc epimerase, GalE, and is found in *E. coli* strains that do not initiate O-antigen repeat unit synthesis with GalNAc. Z3206 in *E. coli* O157, a gene with a high degree of homology to gne1, was identified as a candidate GlcNAc-P-P-Und 4-epimerase. The genomic location of the Z3206 gene is consistent with a role in this pathway, as it resides between galF of the O-antigen cluster and wcaM which belongs to the colanic acid cluster.

The research described in Examples 2-11 further confirms the above discoveries, including identifying the GlcNAc 4-epimerase (*E. coli* O157 Z3206) as catalyzing the formation of GalNAc-P-P-Und.

Example 2

UDP-GalNAc is Not a Substrate for *E. coli* WecA (GlcNAc-phosphotransferase)

To determine if *E. coli* WecA will utilize UDP-GalNAc as a GalNAc-P donor to form GalNAc-P-P-Und, membrane fractions from *E. coli* strains K12, PR4019, a WecA-overexpressing strain, and O157, which synthesize a tetrasaccharide O-antigen repeat unit with GalNAc at the reducing terminus presumably initiated by the synthesis of GalNAc-P-P-Und, were incubated with UDP-[$^3$H]GalNAc.

Preparation of *E. coli* membranes—Bacterial cells were collected by centrifugation at 1,000×g for 10 min, washed once in ice-cold phosphate-buffered saline, once with cold water, and once with 10 mM Tris-HCl, pH 7.4, 0.25 M sucrose. The cells were resuspended to a density of ~200 $A_{600}$ units/ml in 10 mM Tris-HCl, pH 7.4, 0.25 M sucrose, 10 mM EDTA containing 0.2 mg/ml lysozyme, and incubated at 30° C. for 30 min. Bacterial cells were recovered by centrifugation at 1,000×g for 10 min, quickly resuspended in 40 volumes of ice-cold 10 mm Tris-HCl, pH 7.4, and placed on ice. After 10 min the cells were homogenized with 15 strokes with a tight-fitting Dounce homogenizer and supplemented with 0.1 mM phenylmethylsulfonyl fluoride and sucrose to a final concentration of 0.25 M. Unbroken cells were removed by centrifugation at 1,000×g for 10 min, and cell envelopes were recovered by centrifugation at 40,000×g for 20 min. The membrane fraction was resuspended in 10 mm Tris-HCl, pH 7.4, 0.25 M sucrose, 1 mM EDTA and again sedimented at 40,000×g and resuspended in the same buffer to a protein concentration of ~20 mg/ml. Membrane fractions were stored at −20° C. until needed.

Assay For the Biosynthesis of [$^3$H]GlcNAc-P-P-Und and [$^3$H]GalNAc-P-P-Und in *E. coli* Membranes In Vitro—Reaction mixtures for the synthesis of GlcNAc-P-P-Und and GalNAc-P-P-Und contained 50 mM Tris-HCl, pH 8, 40 mM $MgCl_2$, 5 mM dithiothreitol, 5 mM 5'AMP, *E. coli* membrane fraction (50-200 μg membrane protein, and either 5 μm UDP-[$^3$H]GlcNAc/GalNAc (500-2500 dpm/pmol) in a total volume of 0.05 ml. After incubation at 37° C., reactions were terminated by the addition of 40 volumes of $CHCl_3/CH_3OH$ (2:1), and the total lipid extract containing [$^3$H]HexNAc-P-P-undecaprenols was prepared as described previously (Waechter, C. J., Kennedy, J. L. and Harford, J. B. (1976) *Arch. Biochem. Biophys.* 174, 726-737). After partitioning, the organic phase was dried under a stream of nitrogen and redissolved in 1 ml $CHCl_3/CH_3OH$ (2:1), and an aliquot (0.2 ml) was removed, dried in a scintillation vial, and analyzed for radioactivity by liquid scintillation spectrometry in a Packard Tri-Carb 2100 TR liquid scintillation spectrometer. To determine the rate of synthesis of [$^3$H]GlcNAc-P-P-Und or [$^3$H]GalNAc-P-P-Und, the lipid extract was dried under a stream of nitrogen, redissolved in a small volume of $CHCl_3/CH_3OH$ (2:1), and spotted on a 10×20-cm borate-impregnated Baker Si250 silica gel plate, and the plate was developed with $CHCl_3$, $CH_3OH$, $H_2O$, 0.2 M sodium borate (65:25:2:2). Individual glycolipids were detected with a Bioscan AR2000 Imaging Scanner (Bioscan, Washington, D.C.). The biosynthetic rates for each glycolipid were calculated by multiplying the total amount of radioactivity in [$^3$H]GlcNAc/GalNAc-P-P-Und by the percentage of the individual [$^3$H] glycolipids.

Membrane fractions from different *E. coli* strains (K12, PR4019 and O157) were incubated with either UDP-[$^3$H]GlcNAc or UDP-[$^3$H]GalNAc and the incorporation into [$^3$H]GlcNAc/GalNAc-P-P-Und was determined as described above. As seen in Table 3, no labeled glycolipids were detected after the incubation with UDP-[$^3$H]GalNAc, only GlcNAc-P-P-Und was detectable when membrane fractions were incubated with UDP-[$^3$H]GlcNAc

TABLE 3

Synthesis of [$^3$H]GlcNAc/GalNAc-P-P-undecaprenol in *E. coli* membrane fractions using either UDP-[$^3$H]GlcNAc or UDP-[$^3$H]GalNAc as substrate

| | | [$^3$H]Glycolipid formed | |
|---|---|---|---|
| Source of membranes | Sugar nucleotide added | GlcNAc-P-P-Und (pmol/mg) | GalNAc-P-P-Und (pmol/mg) |
| K12 | UDP-[$^3$H]GlcNAc | 6.4 | <0.01 |
| K12 | UDP-[$^3$H]GalNAc | <0.01 | <0.01 |
| PR4019 | UDP-[$^3$H]GlcNAc | 44 | <0.01 |

TABLE 3-continued

Synthesis of [$^3$H]GlcNAc/GalNAc-P-P-undecaprenol in
E. coli membrane fractions using either UDP-[$^3$H]GlcNAc
or UDP-[$^3$H]GalNAc as substrate

| Source of membranes | Sugar nucleotide added | [$^3$H]Glycolipid formed | |
|---|---|---|---|
| | | GlcNAc-P-P-Und (pmol/mg) | GalNAc-P-P-Und (pmol/mg) |
| PR4019 | UDP-[$^3$H]GalNAc | <0.01 | <0.01 |
| O157 | UDP-[$^3$H]GlcNAc | 1.5 | 0.5 |
| O157 | UDP-[$^3$H]GalNAc | <0.01 | <0.01 |

Moreover, neither the addition of exogenous Und-P to incubations with membranes from PR4019, the WecA-overexpressing strain, or the addition of cytosolic fractions from O157 cells resulted in the formation of GalNAc-P-P-Und from UDP-GalNAc. These results demonstrate that UDP-GalNAc is not a substrate for WecA and suggest that GalNAc-P-P-Und is formed by an alternative mechanism.

When membranes from strain K12 were incubated with UDP-[$^3$H]GlcNAc, [$^3$H]GlcNAc-P-P-Und was synthesized as expected (Rush, J. S., Rick, P. D. and Waechter, C. J. (1997) Glycobiology, 7, 315-322). However, when membranes from strain O157 were incubated with UDP-[$^3$H]GlcNAc, in addition to [$^3$H]GlcNAc-P-P-Und, a second labeled lipid shown to be [$^3$H]GalNAc-P-P-Und (see below) was observed. When the time course for the formation of the two glycolipids was examined, the incorporation of radioactivity into [$^3$H] GlcNAc-P-P-Und (FIG. 1, O) occurred more quickly and to a higher extent than into [$^3$H]GalNAc-P-P-Und (FIG. 1, ●), compatible with a precursor-product relationship (FIG. 2).

The observation that E. coli O157 membranes do not utilize UDP-GalNAc as a GalNAc-P donor for the synthesis of GalNAc-P-P-Und is one example which confirms the biosynthetic pathway for the formation of GalNAc-P-P-Und illustrated in FIG. 2. In this scheme, GlcNAc-P-P-Und is formed by the transfer of GlcNAc-P from UDP-GlcNAc, catalyzed by WecA, and then GlcNAc-P-P-Und is epimerized by the action of a previously unknown 4-epimerase to produce GalNAc-P-P-Und.

Example 3

Characterization of [$^3$H]GalNAc-P-P-Und Formed in Vitro with Membrane Fractions from E. coli Strain O157

Consistent with the additional O157-specific glycolipid product detected in FIG. 1, as GalNAc-P-P-Und, it was stable to mild alkaline methanolysis (toluene/methanol 1:3, containing 0.1 N KOH, 0° C., 60 min), retained by DEAE-cellulose equilibrated in CHCl$_3$/CH$_3$OH/H$_2$O (10:10:3), and eluted with CHCl$_3$/CH$_3$OH/H$_2$O (10:10:3) containing 20 mM ammonium acetate as reported previously for [$^3$H] GlcNAc$_{1-2}$-P-P-Dol (Waechter, C. J. and Harford, J. B. (1977) Arch. Biochem. Biophys. 181, 185-198).

Figure 3A:
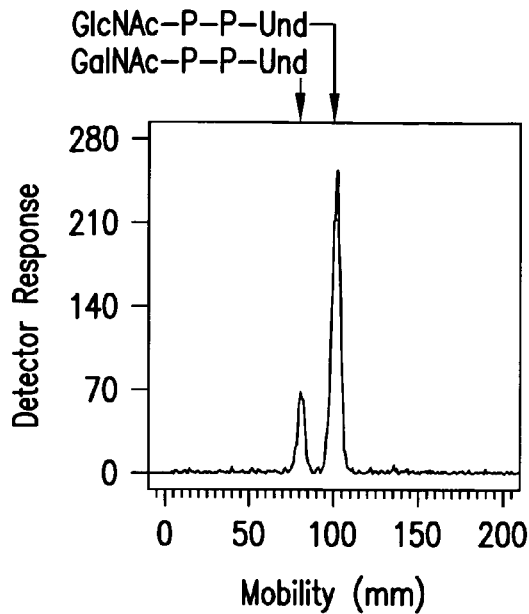
FIG. 3A, preparative thin layer chromatogram of [$^3$H]HexNAc lipids on borate-impregnated silica gel G (Quantum 1) after purification on DEAE-cellulose is shown.

[$^3$H]GalNAc-P-P-Und was clearly resolved from [$^3$H] GlcNAc-P-P-Und by thin layer chromatography on borate-impregnated silica gel G (Kean, E. L. (1966) J. Lipid Res. 7, 449-452) and purified by preparative TLC as shown in FIG. 3A and FIG. 3B.

Preparation of Borate-impregnated Thin Layer Plates and Whatman No. 1 Paper—Silica gel thin layer plates were impregnated with sodium borate by briefly immersing the plates in 2.5% Na$_2$B$_4$O$_7$·10 H$_2$O in 95% methanol as described by Kean (Kean, E. L. (1966) J. Lipid Res. 7, 449-452). The borate-impregnated TLC plates were dried overnight at room temperature and stored in a vacuum dessicator over Drierite until use. Immediately before chromatography, the plates were activated by heating briefly (~10-15 min) to 100° C. Whatman No. 1 paper was impregnated with sodium borate by dipping 20×30-cm sheets of Whatman 1 paper in 0.2 Na$_2$B$_4$O$_7$·10 H$_2$O. The Whatman No. 1 paper sheets were pressed firmly between two sheets of Whatman No. 3MM paper and allowed to dry at room temperature for several days, as described by Cardini and Leloir (Cardini, C. E. and Leloir, L. F. (1957) J. Biol. Chem. 225, 317-324).

Characterization of Glycan Products Formed in in Vitro Reactions—The glycans of the individual glycolipids ([$^3$H] GalNAc-P-P-Und and [$^3$H]GlcNAc-P-P-Und) were characterized by descending paper chromatography after release by mild acid hydrolysis. The GlcNAc/GalNAc lipids were dried under a stream of nitrogen in a conical screw-cap tube and heated to 100° C., 15 min in 0.2 ml 0.01 M HCl. After hydrolysis the samples were applied to a 0.8-ml mixed-bed ion-exchange column containing 0.4 ml of AG50WX8 (H$^+$) and 0.4 ml AG1X8 (acetate form) and eluted with 1.5 ml water. The eluate was dried under a stream of nitrogen, redissolved in a small volume of H$_2$O (0.02 ml), spotted on a 30-cm strip of borate-impregnated Whatman No. 1 paper, and developed in descending mode with butanol/pyridine/water (6:4:3) for 40-50 h. After drying, the paper strips were cut into 1-cm zones and analyzed for radioactivity by scintillation spectrometry. GlcNAc and GalNAc standards were detected using an aniline-diphenylamine dip reagent (Schwimmer, S. and Benvenue, A. (1956) Science 123, 543-544).

Glycan products were converted to their corresponding alditols by reduction with 0.1 M NaBH$_4$ in 0.1 M NaOH (final volume 0.1 ml) following mild acid hydrolysis as described above. After incubation at room temperature overnight, the reactions were quenched with several drops of glacial acetic acid and dried under a stream of nitrogen out of methanol containing 1 drop of acetic acid, several times. The alditols were dissolved in water, desalted by passage over 0.5 ml columns of AG50WX8 (H+) and AG1X8 (acetate), dried under nitrogen, and spotted on 30-cm strips of Whatman No. 3MM paper. The Whatman No. 3 MM strips were developed overnight in descending mode with ethyl acetate, pyridine, 0.1 M boric acid (65:25:20), dried, cut into 1-cm zones, and analyzed for radioactivity by scintillation spectrometry. GlcNAcitol and GalNAcitol standards were visualized using a modification of the periodate-benzidine dip procedure (Gordon, H. T., Thornburg, W. and Werum, L. N. (1956) Anal. Chem. 28, 849-855). The paper strips were dipped in acetone, 0.1 M NaIO$_4$ (95:5), allowed to air dry for 3 min, and then dipped in acetone/acetic acid/H$_2$O/o-tolidine (96:0.6:4.4:0.2 gm). Alditols containing cis-diols stain as yellow spots on a blue background.

Mass Spectrometry ("MS") of Glycolipids—Purified glycolipids were analyzed using an ABI/MDS Sciex 4000 Q-Trap hybrid triple quadrupole linear ion trap mass spectrometer with an ABI Turbo V electrospray ionsource (ABI/MDS-Sciex, Toronto, Canada). In brief, samples were infused at 10 µl/min with ion source settings determined empirically, and MS/MS (mass spectroscopy in a second dimension) information was obtained by fragmentation of the molecular ion in linear ion trap mode.

Figure 3C:
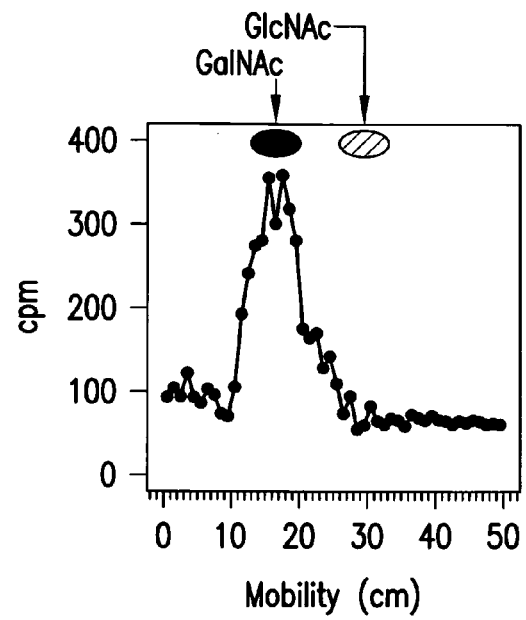
FIG. 3C, descending paper chromatogram (borate-impregnated Whatman No. 1 paper) of the [$^3$H]-amino sugar recovered after mild acid hydrolysis of [$^3$H]GalNAc-P-P-Und purified in FIG. 3B is shown.
Figure 3B:
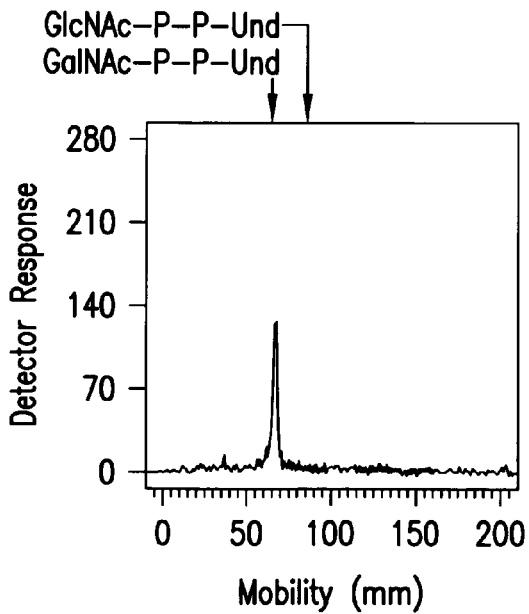
FIG. 3B, thin layer chromatography of purified [$^3$H]GalNAc-P-P-Und on borate-impregnated silica gel G (Baker, Si250) after recovery from the preparative plate in panel A is shown.
Figure 3D:
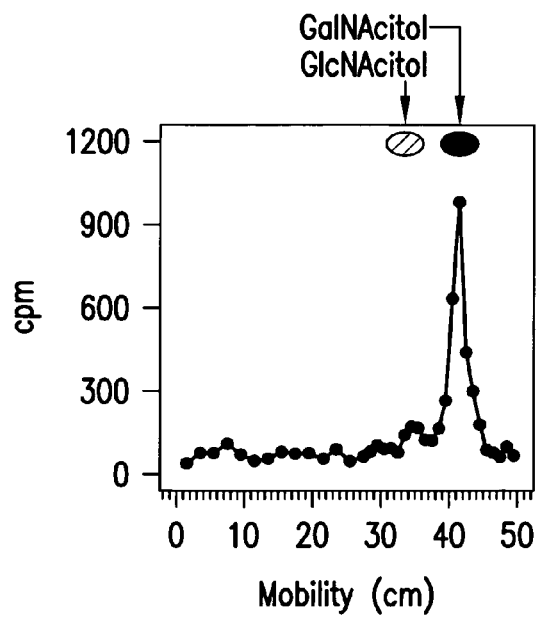
FIG. 3D, descending paper chromatogram (Whatman No. 3MM) of the [$^3$H]HexNAc-alditol produced by reduction of the [$^3$H] amino sugar from FIG. 3C with NaBH$_4$.

When the glycolipid was treated with mild acid (0.01 N HCl, 100° C., 15 min), the water-soluble product co-chromatographed with [$^3$H]GalNAc on descending paper chromatography with borate-impregnated Whatman No. 1 paper (FIG. 3C). In addition, when the labeled sugar was reduced, it was converted to [$^3$H]alditol, GalNAc-OH (FIG. 3D). Moreover, negative-ion MS analysis yielded the [M-H]-ion of m/z=1128, expected for GalNAc-P-P-Und, and the MS/MS daughter ion spectrum showed a prominent ion at m/z=907, expected for a glycolipid containing P-P-Und (Guan, Z., Breazeale, S. D. and Raetz, C. R. (2005) *Anal. Biochem.* 345, 336-339). The identification of the glycolipid product formed by strain O157 as GalNAc-P-P-Und is also supported by its formation from exogenous GlcNAc-P-P-Und (see Example 7).

Example 4

Metabolic Labeling of [$^3$H]GalNAc-P-P-Und (in vivo) with [$^3$H]GlcNAc in *E. coli* Cells Expressing the Z3206 Gene To investigate whether expression of the *E. coli* O157 Z3206 gene enabled cells to synthesize GalNAc-P-P-Und, *E. coli* strain 21546 (Meier-Dieter, U., Starman, R., Barr, K., Mayer, H. and Rick, P. D. (1990) *J. Biol. Chem.*, 265, 13490-13497) expressing the Z3206 gene was labeled metabolically with [$^3$H]GlcNAc and analyzed for [$^3$H]GlcNAc/GalNAc-P-P-Und formation.

Metabolic Labeling of Bacterial Cells—*E. coli* cells were cultured with vigorous shaking in Luria-Bertani medium at 37° C. to an $A_{600}$ of 0.5-1. [$^3$H]GlcNAc was added to a final concentration of 1 µCi/ml and the incubation was continued for 5 min at 37° C. The incorporation of radiolabel into glycolipids was terminated by the addition of 0.5 gm/ml crushed ice, and the cultures were thoroughly mixed. The bacterial cells were recovered by centrifugation at 4000×g for 10 min, and the supernatant was discarded. The cells were washed with ice-cold phosphate-buffered saline two times, resuspended by vigorous vortex mixing in 10 volumes (cell pellet) of methanol, and sonicated briefly with a probe sonicator at 40% full power. After sonication, 20 volumes of chloroform were added, and the extracts were mixed vigorously and allowed to stand at room temperature for 15 min. The insoluble material was sedimented by centrifugation, and the pellet was re-extracted with a small volume of CHCl$_3$/CH$_3$OH (2:1) twice. The combined organic extracts were then processed as described below.

Purification of GlcNAc-P-P-Und and GalNAc-P-P-Und—GlcNAc/GalNAc-P-P-Und was extracted with CHCl$_3$/CH$_3$OH (2:1) and freed of water-soluble material by partitioning as described elsewhere (Waechter, C. J., Kennedy, J. L. and Harford, J. B. (1976) *Arch. Biochem. Biophys.* 174, 726-737). The organic extract was then dried under a stream of nitrogen, and the bulk glycerophospholipids were destroyed by deacylation in toluene/methanol (1:3) containing 0.1 N KOH at 0° C. for 60 min. The deacylation reaction was neutralized with acetic acid, diluted with 4 volumes of CHCl$_3$/CH$_3$OH (2:1), and washed with ⅕ volume of 0.9% NaCl. The organic (lower) phase was washed with ⅓ volume of CHCl$_3$, CH$_3$OH, 0.9% NaCl (3:48:47), and the aqueous phase was discarded. The organic phase was diluted with sufficient methanol to accommodate the residual aqueous phase in the organic phase and applied to a DEAE-cellulose column (5 ml) equilibrated with CHCl$_3$/CH$_3$OH (2:1). The column was washed with 20 column volumes of CHCl$_3$/CH$_3$OH/H$_2$O (10:10:3) and then eluted with CHCl$_3$/CH$_3$OH/H$_2$O (10:10:3) containing 20 mm ammonium acetate. Fractions (2 ml) were collected and monitored for either radioactivity, or GlcNAc/GalNAc-P-P-Und using an anisaldehyde spray reagent (Dunphy, P. J., Kerr, J. D., Pennock, J. F., Whittle, K. J., and Feeney, J. (1967) *Biochim. Biophys. Acta* 136, 136-147) after resolution by thin layer chromatography on borate-impregnated silica plates (as described earlier).

Figure 4A:
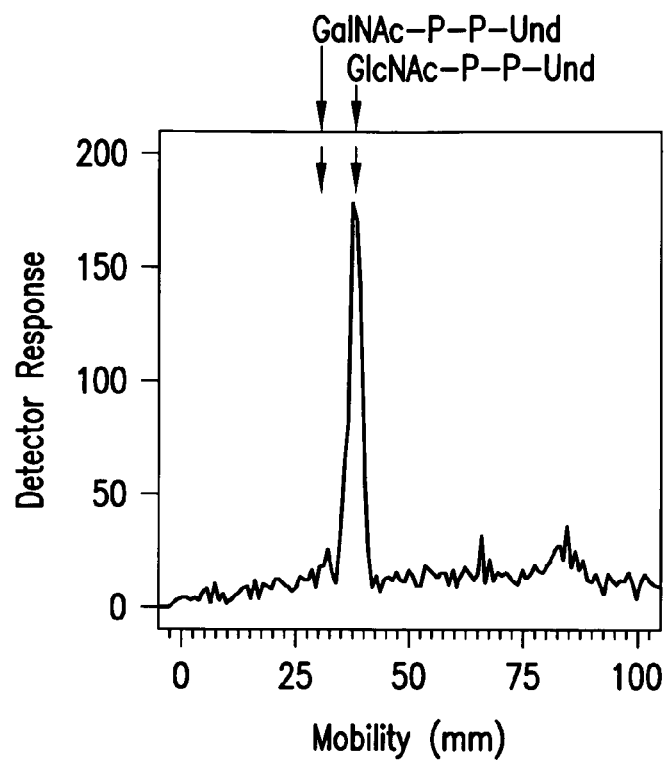
FIG. 4 shows metabolic labeling of E. coli 21546 cells and E. coli 21546 cells after transformation with pMLBAD: Z3206. E. coli 21546 (FIG. 4A) and E. coli 21546:pMLBAD/Z3206 (FIG. 4B) were labeled metabolically with [$^3$H] GlcNAc for 5 min at 37° C. [$^3$H]GlcNAc/GalNAc-P-P-Und were extracted, freed of water soluble contaminants and separated by thin layer chromatography on borate-impregnated silica gel plates (Baker Si250) as described in Example 3. Radioactive lipids were detected using a Bioscan chromatoscanner. The chromatographic positions of GalNAc-P-P-Und and GlcNAc-P-P-Und are indicated by arrows.
Figure 4B:
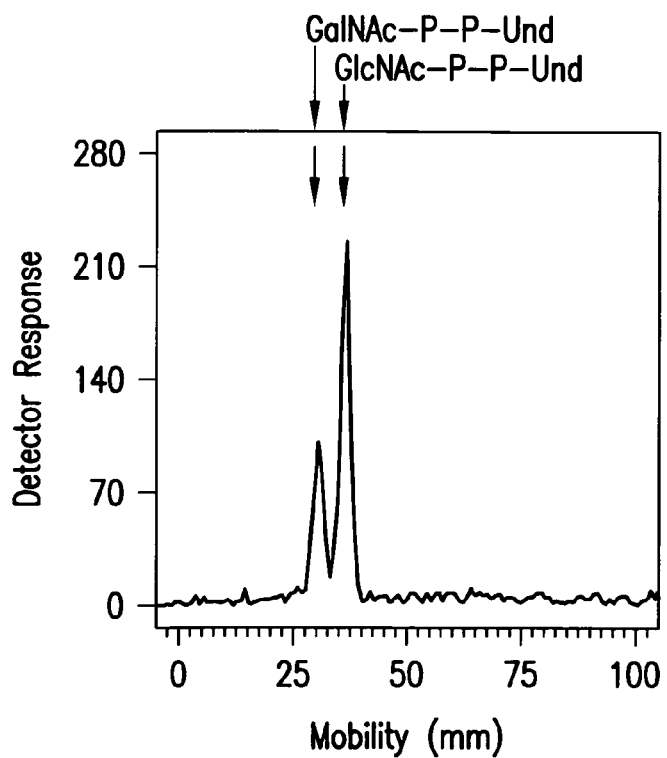
Figure 5A:
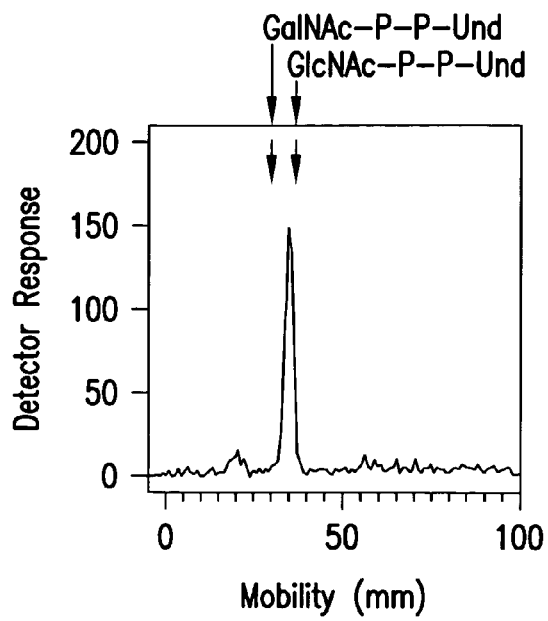
FIG. 5 shows thin layer chromatography of [$^3$H]GlcNAc/GalNAc-P-P-Und formed by incubation of membrane fractions from E. coli strains with UDP-[$^3$H]GlcNAc. Membrane fractions from E. coli strains K12 (FIG. 5A), O157 (FIG. 5B), 21546 (FIG. 5C), and 21546:pMLBAD/Z3206 (FIG. 5D) were incubated with UDP-[$^3$H]GlcNAc for 10 min at 37° C., and the [$^3$H]lipid products were extracted, freed of water-soluble contaminants by partitioning, and separated by thin layer chromatography on borate-impregnated silica gel plates (Baker Si250) as described in Example 3. The chromatographic positions of GalNAc-P-P-Und and GlcNAc-P-P-Und are indicated by arrows.
Figure 5C:
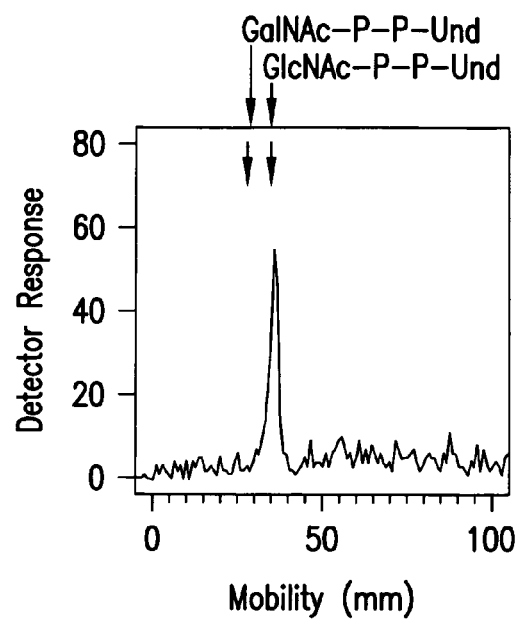
Figure 5B:
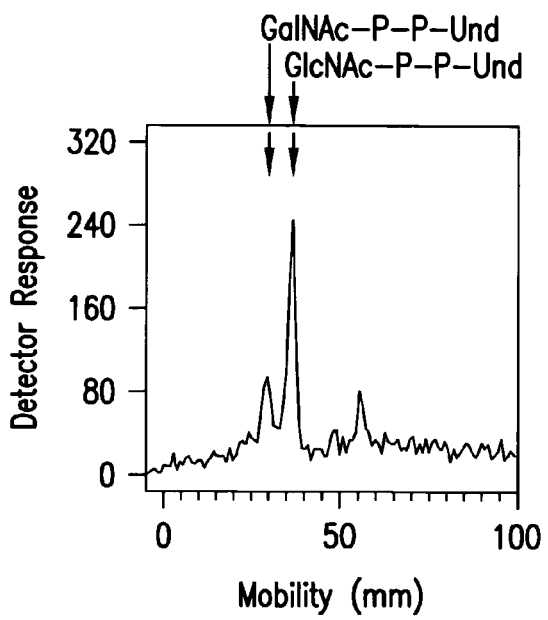
Figure 5D:
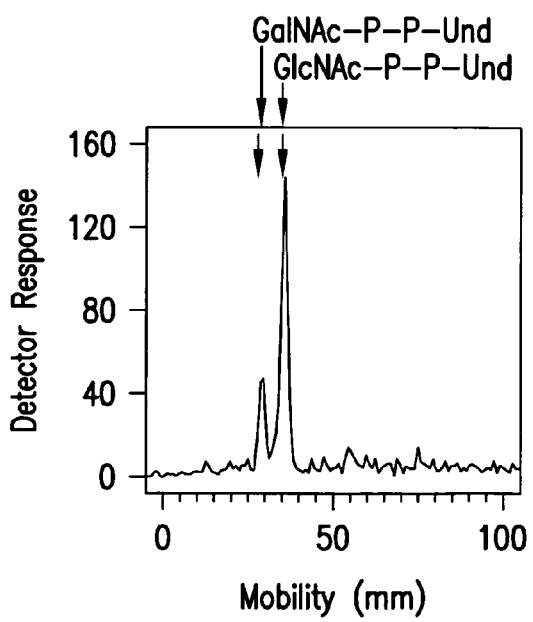

*E. coli* strain 21546 was selected as the host for the Z3206 expression studies because a mutation in UDP-ManNAcA synthesis results in a block in the utilization of GlcNAc-P-P-Und for the synthesis of the enterobacterial common antigen. Because *E. coli* 21546 is derived from *E. coli* K12 it does not synthesize an O-antigen repeat as well (Stevenson, G., Neal, B., Liu, D., Hobbs, M., Packer, N. H., Batley, M., Redmond, J. W., Lindquist, L. and Reeves, P. (1994) *J. Bacteriol.*, 176, 4144-4156), and thus, larger amounts of GlcNAc-P-P-Und accumulate for the conversion to GalNAc-P-P-Und. When strain 21546 and the transformant expressing the Z3206 gene were labeled with [$^3$H]GlcNAc and the radiolabeled lipids were analyzed by thin layer chromatography on borate-impregnated silica gel plates, the parental strain (FIG. 4A) synthesized only one labeled lipid, GlcNAc-P-P-Und. However, 21546 cells expressing the Z3206 gene (FIG. 4B) also synthesized an additional labeled lipid shown to be GalNAc-P-P-Und.

Example 5

Membrane Fractions from *E. coli* Cells Expressing the Z3206 Gene Synthesize GalNAc-P-P-Und in Vitro To corroborate that the protein encoded by the *E. coli* O157 Z3206 gene catalyzed the synthesis of GalNAc-P-P-Und, membrane fractions from *E. coli* cells expressing the Z3206 gene were incubated with [$^3$H]UDP-GlcNAc and the [$^3$H] glycolipid products were analyzed by thin layer chromatography (chromatographic preparation and characterization methods are described in Example 3) on borate-impregnated silica gel plates as shown in FIG. 5. When membrane fractions from *E. coli* K12 or the host strain *E. coli* 21546 cells were incubated with UDP-[$^3$H]GlcNAc, only [$^3$H]GlcNAc-P-P-Und was observed (FIG. 5A and FIG. 5C). However, membrane fractions from *E. coli* O157 and *E. coli* 21546 expressing Z3206 formed GalNAc-P-P-Und as well (FIG. 5B and FIG. 5D).

Example 6

Formation of GlcNAc-P-P-Und, but Not GalNAc-P-P-Und, is Reversed in the Presence of UMP To provide additional evidence that GalNAc-P-P-Und is synthesized from GlcNAc-P-P-Und, and not by the action of WecA using UDP-GalNAc as a glycosyl donor, the effect of discharging endogenous, pre-labeled [$^3$H]GlcNAc-P-P-Und and [$^3$H]GalNAc-P-P-Und with UMP was examined. The GlcNAc-phosphotransferase reaction catalyzed by WecA is freely reversible by the addition of excess UMP re-synthesizing UDP-GlcNAc and releasing Und-P.

Figure 6A:
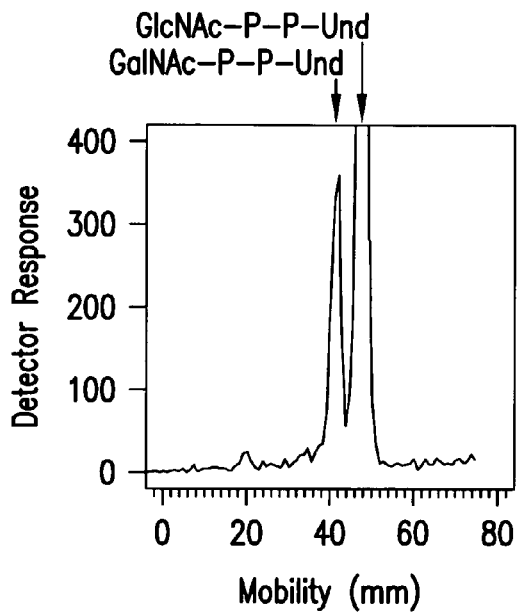
FIG. 6 shows discharge of GlcNAc-P by incubation with UMP. Membrane fractions from E. coli 21546:Z3206 were preincubated with UDP-[$^3$H]GlcNAc to enzymatically label GlcNAc-P-P-Und for 10 min (FIG. 6A) at 37° C. followed by a second incubation period with 1 mM UMP included for either 1 min (FIG. 6B) or 2 min (FIG. 6C). After the indicated incubation periods [$^3$H]GlcNAc/GalNAc-P-P-Und were extracted and resolved by thin layer chromatography on borate-impregnated silica gel plates (Baker Si250) as described in Example 3. The chromatographic positions of GalNAc-P-P-Und and GlcNAc-P-P-Und are indicated by arrows.
Figure 6B:
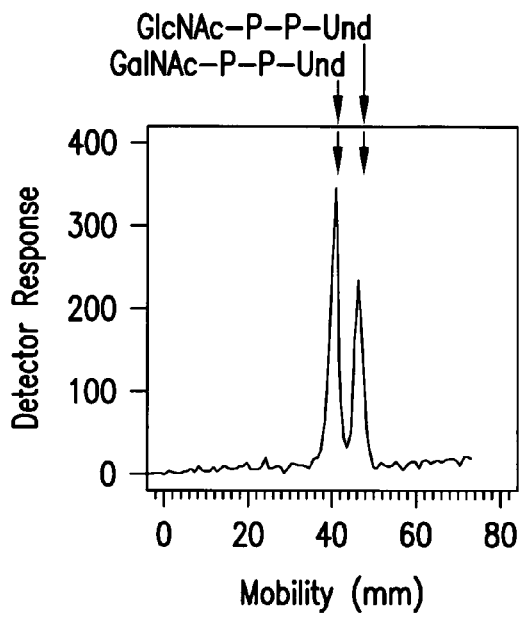

In this experiment membrane fractions from *E. coli* strain 21546 expressing Z3206 were pre-labeled for 10 min with UDP-[$^3$H]GlcNAc followed by the addition of 1 mM UMP, and the amount of each labeled glycolipid remaining was determined. The results illustrated in FIG. 6A show the relative amounts of [$^3$H]GlcNAc-P-P-Und and [$^3$H]GalNAc-P-P-Und at the end of the 10 min labeling period. After incubation with 1 mm UMP for 1 min it can be seen that there is a substantial loss of [$^3$H]GlcNAc-P-P-Und, whereas the [$^3$H] GalNAc-P-P-Und peak is relatively unchanged (FIG. 6B)

Figure 6C:
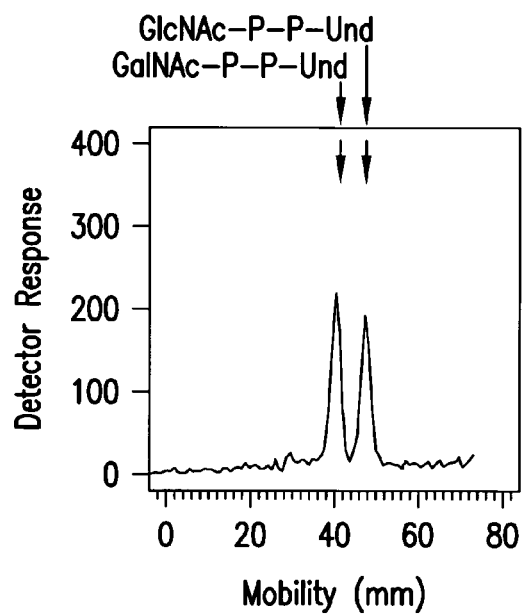

(chromatographic preparation and characterization methods are described in Example 5). This observation is consistent with the results in Table 3 indicating that WecA does not catalyze the transfer of GalNAc-P into GalNAc-P-P-Und from UDP-GalNAc. It is noteworthy that during the second minute of incubation with UMP (FIG. 6C), the loss of GlcNAc-P-P-Und slows, and there is a slight reduction in the peak of [$^3$H]GalNAc-P-P-Und, suggesting that [$^3$H]GalNAc-P-P-Und is re-equilibrating with the [$^3$H]GlcNAc-P-P-Und pool by reversal of the epimerase reaction (see Example 7).

Example 7

Interconversion of Exogenous, Purified [$^3$H]GlcNAc-P-P-Und and [$^3$H]GalNAc-P-P-Und Catalyzed by Membranes from E. coli Cells Expressing Z3206

To provide direct evidence that GlcNAc-P-P-Und and GalNAc-P-P-Und can be directly interconverted by membrane fractions from E. coli cells expressing Z3260, purified [$^3$H]GlcNAc-P-P-Und and [$^3$H]GalNAc-P-P-Und were tested as exogenous substrates.

Purified [$^3$H]GlcNAc-P-P-Und/[$^3$H]GalNAc-P-P-Und were prepared as in Example 4 (Metabolic Labeling of Bacterial Cells and Purification of GlcNAc-P-P-Und and GalNAc-P-P-Und). [$^3$H]HexNAc-P-P-undecaprenols (2000 dpm/pmol, dispersed in 1% Triton X-100, final concentration 0.1%) were incubated with E. coli membranes as in Example 2 in Assay For the Biosynthesis of [$^3$H]GlcNAc-P-P-Und and [$^3$H]GalNAc-P-P-Und in E. coli Membranes In Vitro.

Figure 7A:
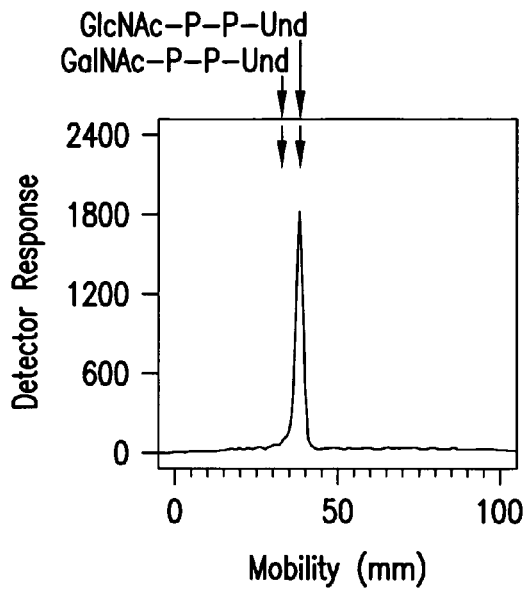
FIG. 7 shows conversion of exogenous [$^3$H]GlcNAc-P-P-Und and [$^3$H]GalNAc-P-P-Und to the pertinent [$^3$H]HexNAc-P-P-Und product catalyzed by membranes from strain 21546 expressing Z3206. Membrane fractions from E. coli strain 21546 (FIG. 7B and FIG. 7E) and 21546:pMLBAD/Z3206 (FIG. 7C and FIG. 7F) were incubated with purified [$^3$H]GlcNAc-P-P-Und (FIG. 7A, FIG. 7B, and FIG. 7C) or [$^3$H]GalNAc-P-P-Und (panels at FIG. 7D, FIG. 7E, and FIG. 7F) (dispersed ultrasonically in 1% Triton X-100) for 1 min at 37° C. [$^3$H]GlcNAc/GalNAc-P-P-Und were extracted, resolved by thin layer chromatography on borate-impregnated silica gel plates (Baker Si250) and detected with a Bioscan AR2000 radiochromatoscanner as described in Example 3.
Figure 7B:
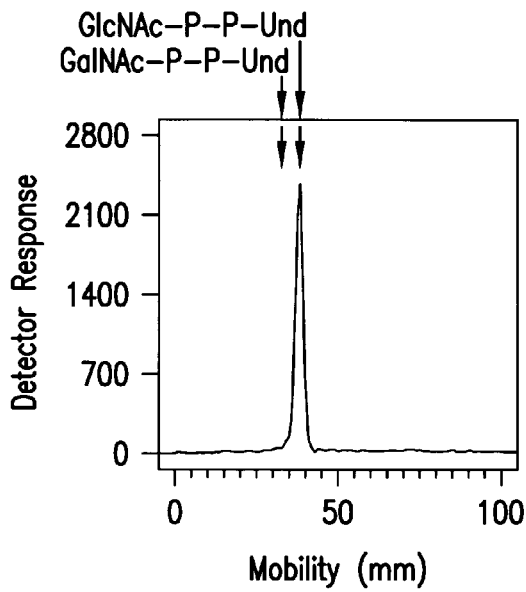
Figure 7C:
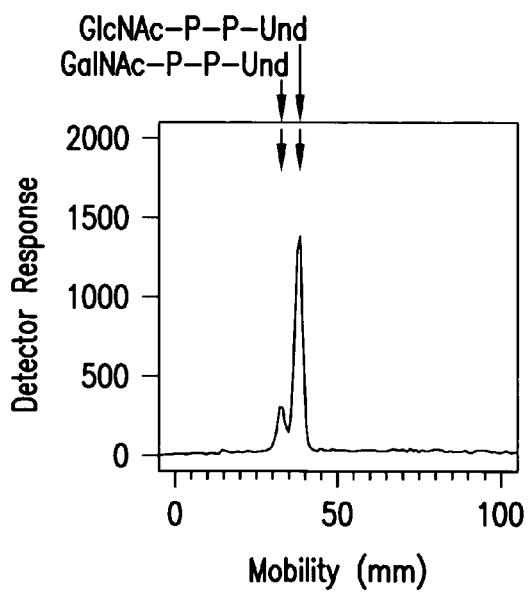
Figure 7D:
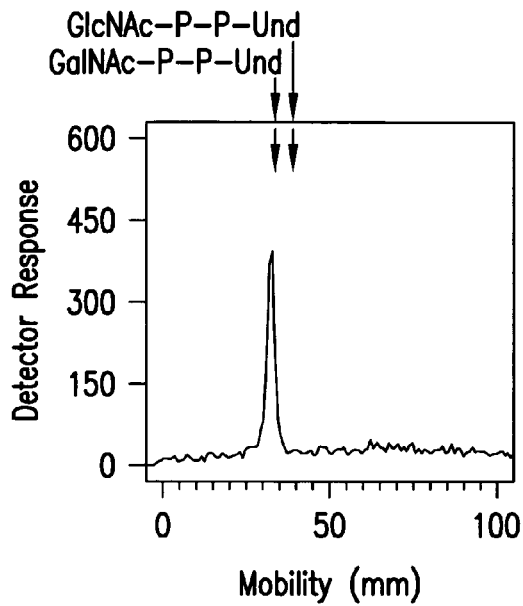
Figure 7E:
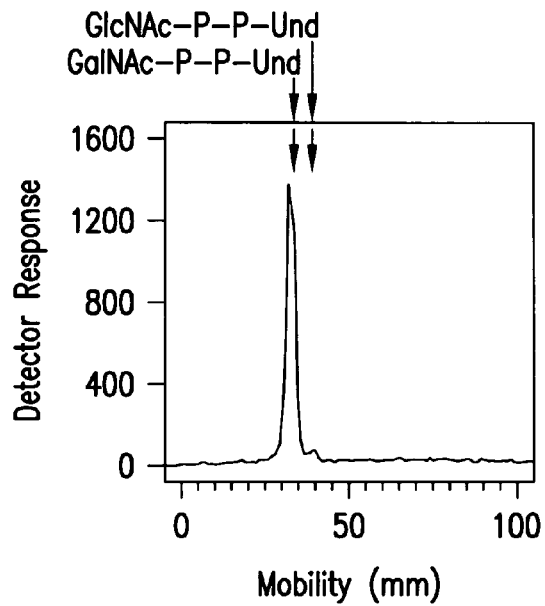
Figure 7F:
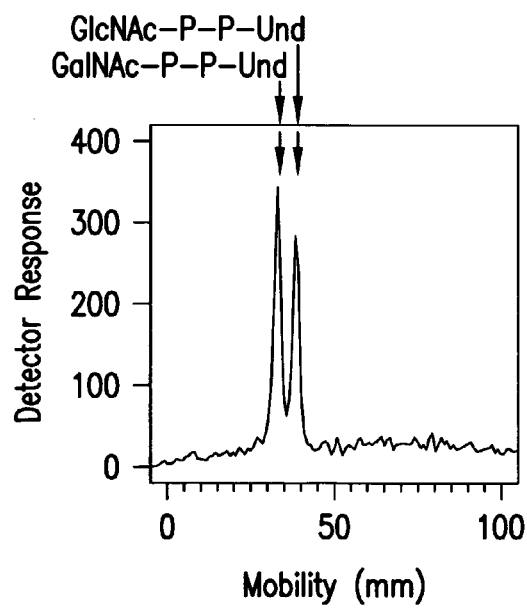

Preliminary experiments showed that the epimerase was active when exogenous [$^3$H]GlcNAc-P-P-Und was added to the reaction mixtures dispersed in Triton X-100, CHAPS (3-[(3-cholamidopropyl)dimethylammonio]-1-propanesulfonic acid), Nonidet P-40, or octylglucoside and exhibited a pH optimum in the range 7-8.5. The chromatographic mobility of the purified [$^3$H]GlcNAc-P-P-Und and [$^3$H]GalNAc-P-P-Und before incubation with membrane fractions is shown in FIG. 7A and FIG. 7D. As seen in FIG. 7B and FIG. 7E, the glycolipids are unaffected by incubation with membrane fractions from E. coli 21546. However, incubation of the purified glycolipids with membrane fractions from E. coli 21546 expressing Z3206 catalyzes the conversion of exogenous [$^3$H]GlcNAc-P-P-Und to [$^3$H]GalNAc-P-P-Und (FIG. 7C) and the conversion of [$^3$H]GalNAc-P-P-Und to [$^3$H]GlcNAc-P-P-Und (FIG. 7F). These results demonstrate directly that GlcNAc-P-P-Und and GalNAc-P-P-Und can be enzymatically interconverted in E. coli strains expressing the Z3206.

Example 8

E. coli Z3206 is Not a UDP-GlcNAc 4-Epimerase

To determine if Z3206 can catalyze the formation of UDP-GalNAc, the N-glycosylation apparatus from C. jejuni was expressed in E. coli. In this reporter system, glycosylation of the target protein AcrA is dependent on the presence of the pgl locus (Wacker, M., Linton, D., Hitchen, P.G., Nita-Lazar, M., Haslam, S. M., North, S. J., Panico, M., Morris, H. R., Dell, A., Wrenn, B. W., Aebi, M. (2002) Science 298, 1790-1793), including a functional Gne UDP-Glc/UDP-GlcNAc epimerase (Bernatchez, S., Szymanski, C. M., Ishiyama, N., Li, J., Jarrell, H. C., Lau, P. C., Berghuis, A. M., Young, N. M., Wakarchuk, W. W. (2005) J. Biol. Chem. 280, 4792-4802). Glycosylation of AcrA is lost if the pgl cluster contains a deletion of gne (Linton, D., Dorrell, N., Hitchen, P. G., Amber, S., Karlyshev, A. V., Morris, H. R., Dell, A., Valvano, M. A., Aebi, M. and Wren, B. W. (2005) Mol Microbiol. 55, 1695-1703). The ability of Z3206 to restore AcrA-glycosylation in the presence of the pgl operon Δgne was investigated in vivo by expressing AcrA (pWA2) together with the pgl locus Δgne complemented by either Gne (pMLBAD:gne) or Z3206 (pMLBAD:Z3206).

Total E. coli cell extracts were prepared for immunodetection analysis using cells at a concentration equivalent to 1 $A_{600}$ unit that were resuspended in 100 μl of SDS loading buffer (Laemmli, U. (1970) Nature 227, 680-685). Aliquots of 10 μl were loaded on 10% SDS-PAGE. Periplasmic extracts of E. coli cells were prepared by lysozyme treatment (Feldman, M. F., Wacker, M., Hernandez, M., Hitchen, P. G., Marolda, C. L., Kowarik, M., Morris, H. R., Dell, A., Valvano, M. A., Aebi, M. (2005) Proc Natl Acad Sci USA 102, 3016-3021), and 10 μl of the final sample (corresponding to 0.2 $A_{600}$ units of cells) was analyzed by SDS-PAGE. After being blotted on nitrocellulose membrane, sample was immunostained with the specific antiserum (Aebi, M., Gassenhuber, J., Domdey, H., and to Heesen, S. (1996) Glycobiology 6, 439-444). Anti-AcrA (Wacker, M., Linton, D., Hitchen, P. G., Nita-Lazar, M., Haslam, S. M., North, S. J., Panico, M., Morris, H. R., Dell, A., Wrenn, B. W., Aebi, M. (2002) Science 298, 1790-1793) antibodies were used. Anti-rabbit IgG-HRP (Bio-Rad) was used as secondary antibody. Detection was carried out with ECL™ Western blotting detection reagents (Amersham Biosciences).

As shown in FIG. 8, the glycosylated protein, which migrates slower than the unglycosylated form, was formed only when cells expressing pgl locus Δgne were complemented by Gne (lane 2). Z3206 was unable to restore glycosylation of the reporter glycoprotein (FIG. 8, lane 1). Accordingly, Z3206 does not complement glycosylation of AcrA in a Gne dependent glycosylation system. Expression of Gne and membrane-associated Z3206 were confirmed by immunodetection.

Example 9

Analysis of S. flexneri 6+/−Z3206 LPS

Figure 9:
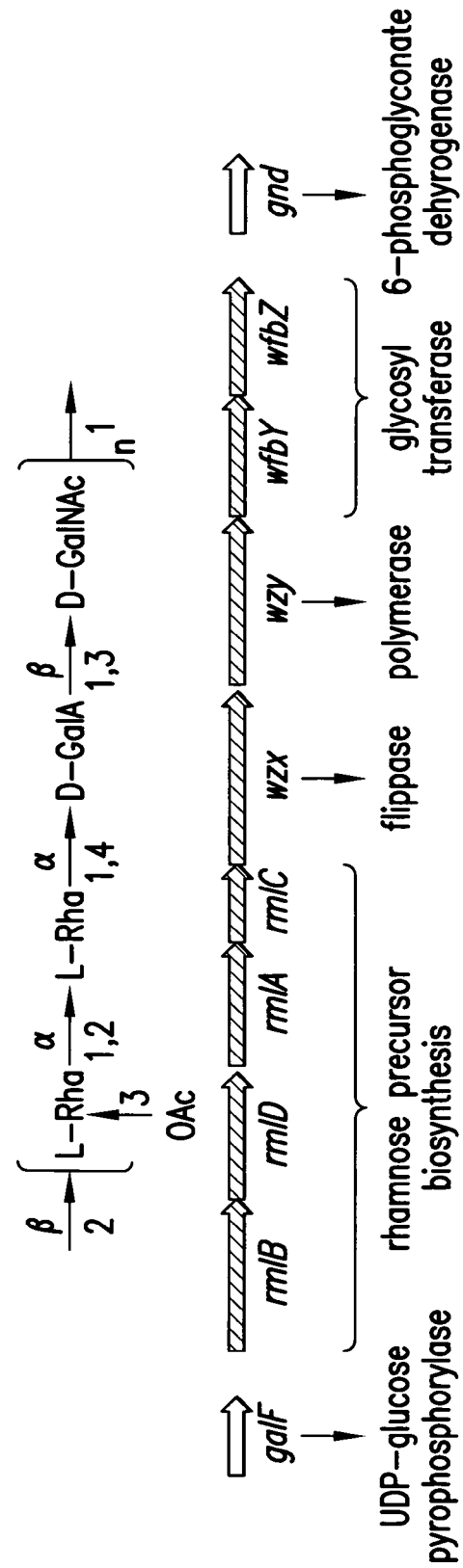
FIG. 9 shows the genes that have been identified by Liu B et al. (*Structure and genetics of Shigella O antigens* FEMS Microbiology Review, 2008. 32: p. 27).

In FIG. 9 are depicted some of the genes required for the biosynthesis of the Shigella flexneri 6 O-antigen: genes encoding enzymes for biosynthesis of nucleotide sugar precursors; genes encoding glycosyltransferases; genes encoding O antigen processing proteins; and genes encoding proteins responsible for the O-acetylation. The structure of the O antigen has been elucidated by Dmitriev, B. A. et al (Dmitriev, B. A., et al Somatic Antigens of Shigella Eur J Biochem, 1979. 98: p. 8; Liu B et al Structure and genetics of Shigella O antigens FEMS Microbiology Review, 2008. 32: p. 27).

To identify all the genes required for the biosynthesis of the Shigella flexneri 6 O-antigen a genomic library was constructed.

Cloning of S. flexneri 6 genomic DNA_S. flexneri 6 genomic DNA was isolated using a Macherey-Nagel NucleoSpin® Tissue Kit following the protocol for DNA isolation from bacteria. DNA was isolated from five S. flexneri 6 overnight cultures at 2 ml each and final elution was done with 100 μl elution buffer (5 mM Tris/HCl, pH 8.5). The eluted fractions were pooled, precipitated by isopropanol and the final pellet was resuspended in 52 μl TE buffer of which the total volume was subjected to end-repair according to the protocol given by CopyControl™ Fosmid Library Production Kit (EPICENTRE). End-repaired DNA was purified on a 1% low melting point agarose gel run with 1×TAE buffer, recovered and precipitated by ethanol as described in the kit protocol. Resuspension of the precipitated DNA was done in 7 µl TE buffer of which 0.15 µl DNA was ligated into pCC1FOS (SEQ ID NO: 27) according to the EPICENTRE protocol. Packaging of the ligation product into phage was performed according to protocol and the packaged phage was diluted 1:1 in phage dilution buffer of which 10 µl were used to infect 100 µl EPI300-T1 cells that were previous grown as described by EPICENTRE. Cells (110 µl) were plated six times with approximately 100 colonies per plate such that the six plates contain the entire S. flexneri 6 genomic library. Plates were developed by colony blotting and positive/negative colonies were western blotted and silver stained.

Colony blotting_For colony blots a nitrocellulose membrane was laid over the solid agar plate, removed, washed three times in 1×PBST and treated in the same manner. The membrane was first blocked in 10% milk for one hour at room temperature after which it was incubated for one hour at room temperature in 2 ml 1% milk (in PBST) with the anti-type VI antiserum (primary antibody). After three washes in PBST at 10 minutes each, the membrane was incubated for another hour at room temperature in the secondary antibody, 1:20000 peroxidase conjugated goat-anti-rabbit IgG (BioRad) in 2 ml 1% milk (in PBST). After a final three washes with PBST (10 minutes each) the membrane was developed in a UVP Chemi Doc Imaging System with a 1:1 mix of luminol and peroxide buffer provided by the SuperSignal® West Dura Extended Duration Substrate Kit (Thermo Scientific).

Figure 10:
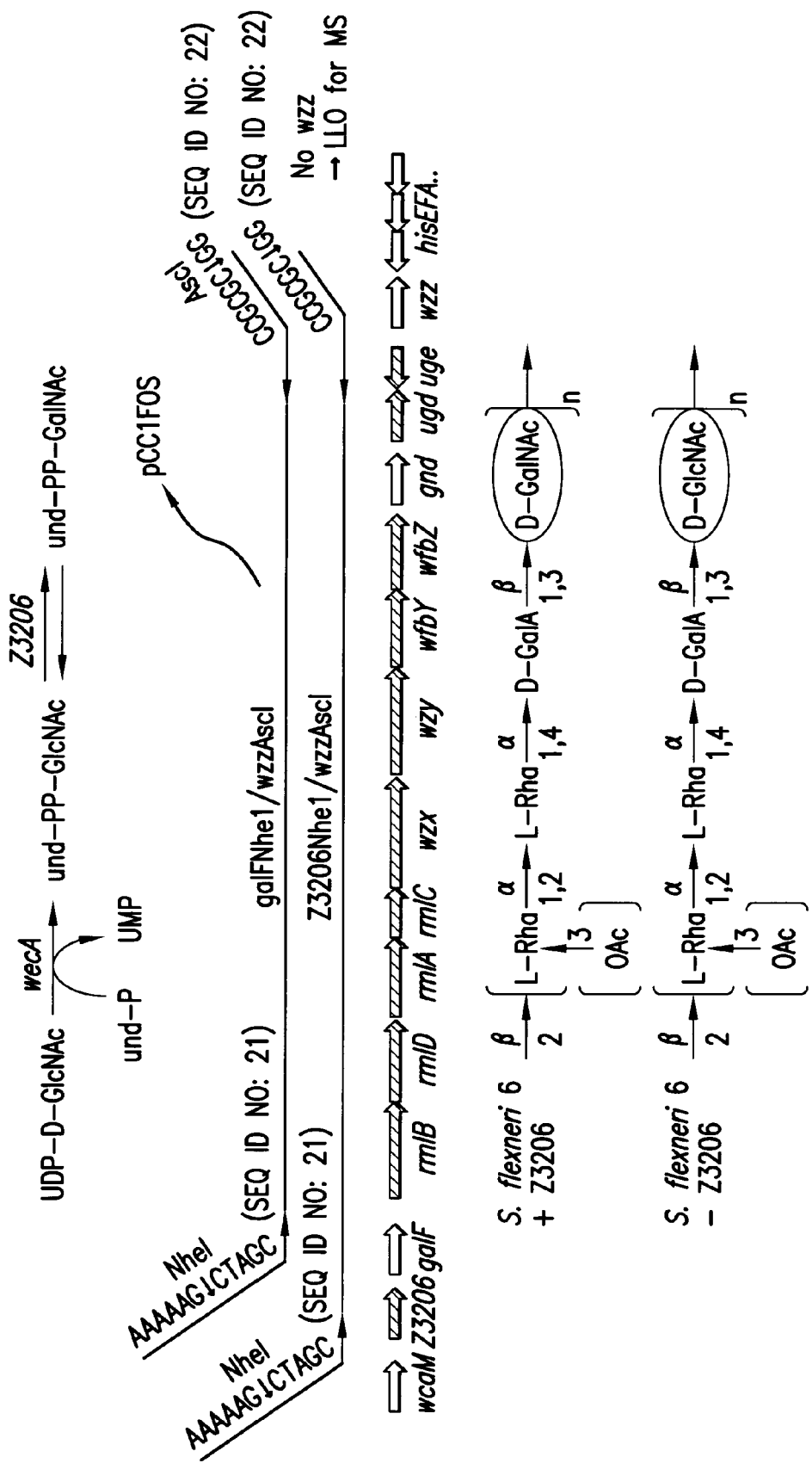
FIG. 10 is a scheme showing the DNA region containing the genes required to synthesize the *S. flexneri* 6 O antigen.

The clone reacting with S. flexneri 6 antiserum following production of a S. flexneri 6 genomic library was sequenced by primer walking out of the region previously sequenced by Liu et al. (Liu et al., 2008) reaching from rmlB to wfbZ (FIG. 9). Primers rm1B_rev and wfbZ_fwd (S. flexneri–Z3206) annealed in rmlB and wfbZ and were used to sequence the insert of the clone until wcaM and hisI/F were reached (S. flexneri+Z3206), respectively (FIG. 10).

In order to establish whether O antigen synthesis is maintained in clones lacking Z3206 (thus hindering epimerization of und-GlcNAc to und-GalNAc), two plasmids were constructed (SEQ ID NO. 28 and SEQ ID NO. 29) (FIG. 10), transformed into E. coli cells and analyzed by silver staining and western blot.

Figure 11:
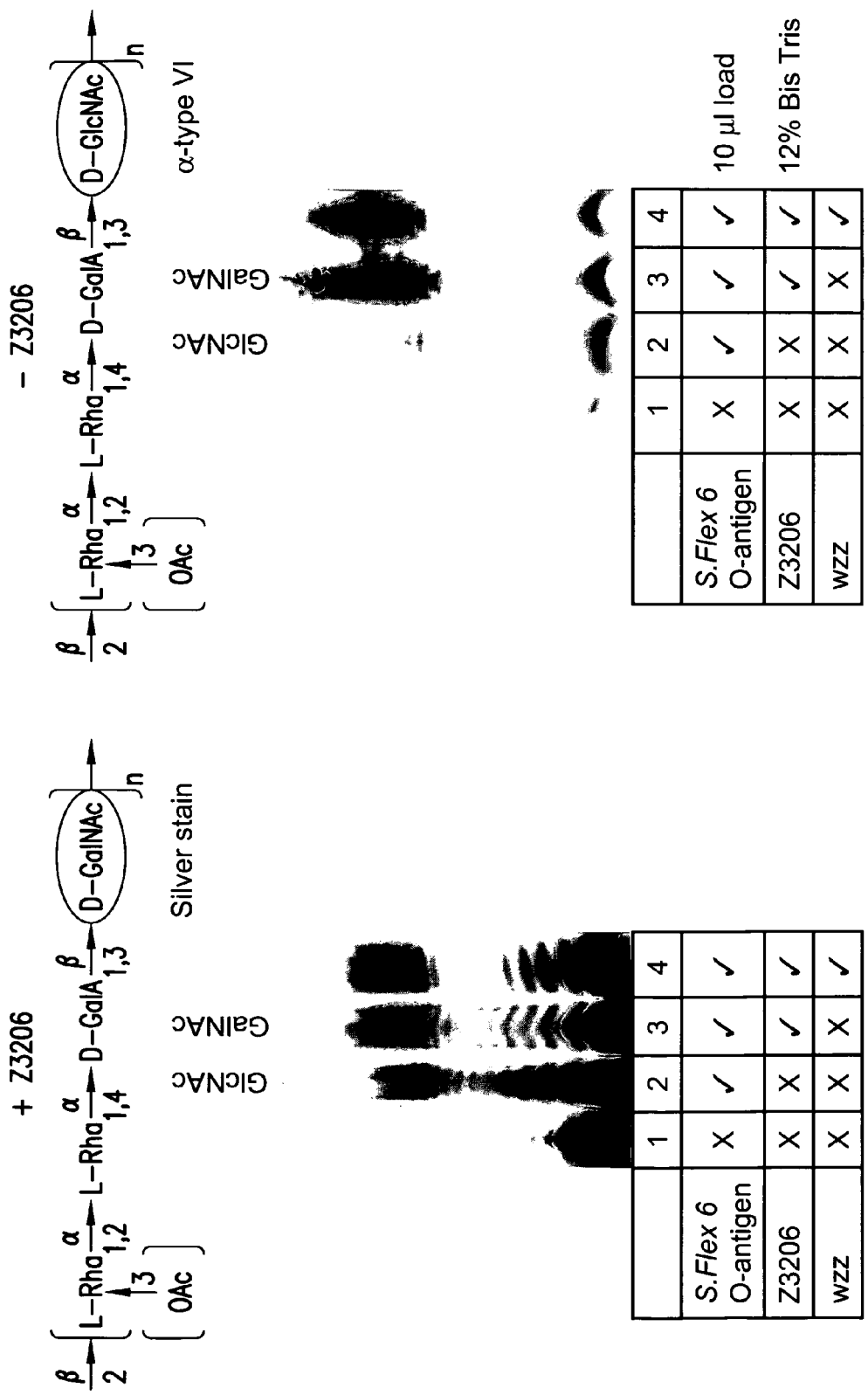
FIG. 11 shows expression of the *S. flexneri* 6 O antigen in *E. coli*. LPS was visualized by either silver staining or by transfer to nitrocellulose membranes and detection by antibodies directed against *S. flexneri* 6.

As shown in FIG. 11, LPS is produced in E. coli cells + or –Z3206. The O antigen can be produced without Z3206 however with lower production yield, which indicates that the efficiency of polysaccharide production without the epimerase (Z3206) is lower.

Example 10

Analysis of S. flexneri 6+/–Z3206 LLO

Purification of undecaprenol-PP-O antigen by C18 column chromatography_E. coli cells expressing S. flexeneri antigen +/–Z3206 were pelleted, washed once in 50 ml 0.9% NaCl and the final pellets were lyophilized overnight. The pellets were washed once in 30 ml 85-95% methanol, reextracted with 10:10:3 chloroform-methanol-water (v/v/v) and the extracts were converted to a two-phase Bligh/Dyer system by addition of water, resulting in a final ratio of 10:10:9 (C:M:W). Phases were separated by centrifugation and the upper aqueous phases were loaded each on a C18 Sep-Pak cartridge conditioned with 10 ml methanol and equilibrated with 10 ml 3:48:47 (C:M:W). Following loading, the cartridges were washed with 10 ml 3:48:47 (C:M:W) and eluted with 5 ml 10:10:3 (C:M:W). 20 OD samples of the loads, flow-throughs, washes and elutions of the C 18 column were dried in an Eppendorf Concentrator Plus, washed with 250 µl methanol, reevaporated and washed a further three times with 30 µl ddH2O.

Glycolipid hydrolysis The glycolipid samples from the wash of the C18 column were hydrolysed by dissolving the dried samples in 2 ml n-propanol:2 M trifluoroacetic acid (1:1), heating to 50° C. for 15 minutes and evaporating to dryness under N2.

Oligosaccharide labeling with 2-aminobenzoate and HPLC Labeling was done according to Bigge et al. (Bigge, 1995) and glycan cleanup was performed using the paper disk method described in Merry et al. (2002) (Merry et al., 2002). Separation of 2-AB labeled glycans was performed by HPLC using a GlycoSep-N normal phase column according to Royle et al. (Royle, 2002) but modified to a three solvent system. Solvent A was 10 mM ammonium formate pH 4.4 in 80% acetonitrole. Solvent B was 30 mM ammonium formate pH 4.4. in 40% acetonitrile. Solvent C was 0.5% formic acid. The column temperature was 30° C. and 2-AB labeled glycans were detected by fluorescence ($\lambda$ex=330 nm, $\lambda$em=420 nm). Gradient conditions were a linear gradient of 100% A to 100% B over 160 minutes at a flow rate of 0.4 ml/min, followed by 2 minutes 100% B to 100% C, increasing the flow rate to 1 ml/min. The column was washed for 5 minutes with 100% C, returning to 100% A over 2 minutes and running for 15 minutes at 100% A at a flow rate of 1 ml/min, then returning the flow rate to 0.4 ml/min for 5 minutes. All samples were injected in water.

Figure 12:
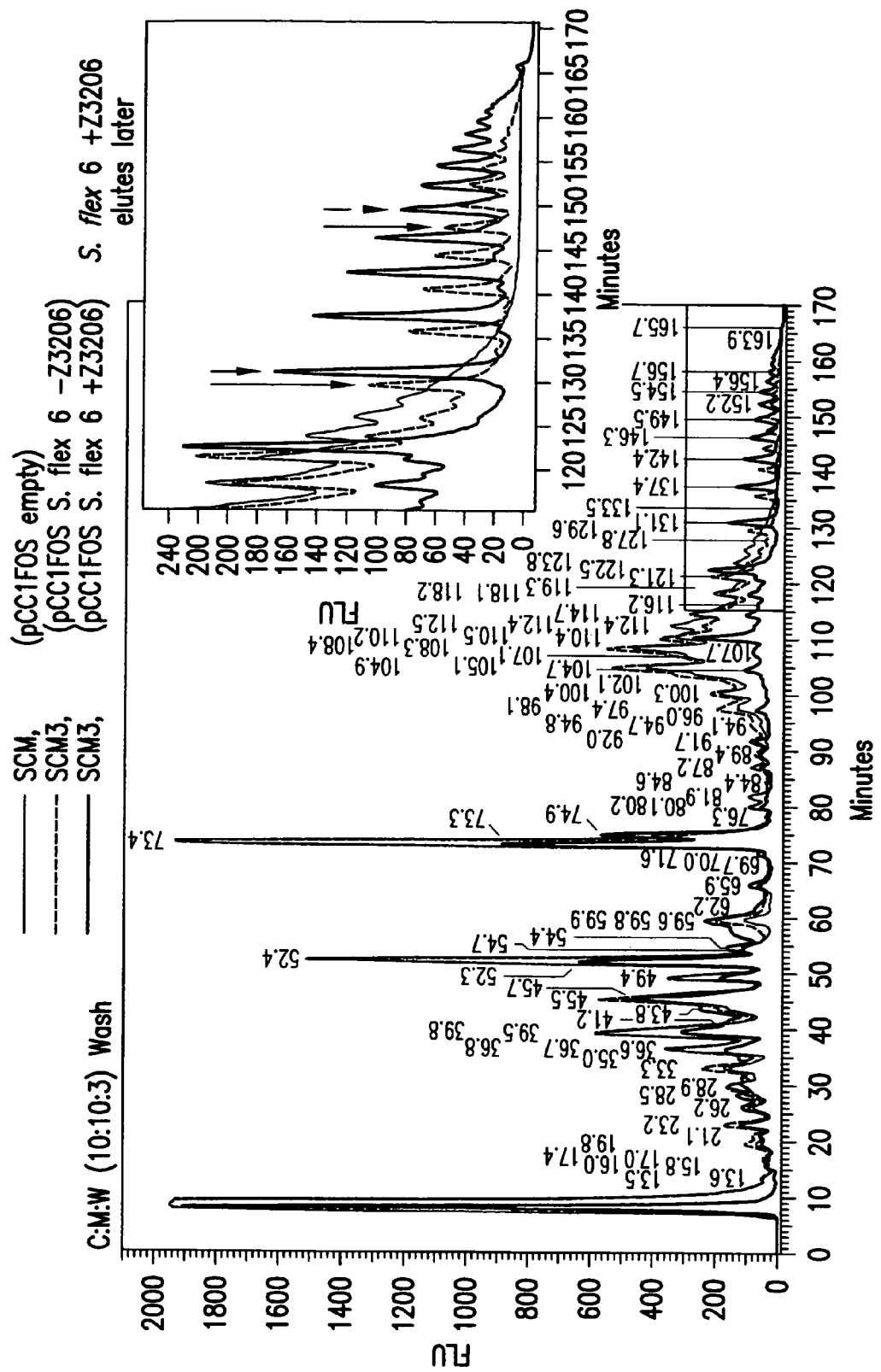
FIG. 12 shows HPLC of O antigen. LLO analysis of *E. coli* cells (SCM3) containing *S. flexneri*−Z3206, *E. coli* cells (SCM3) containing *S. flexneri*+Z3206 or empty *E. coli* (SCM3) cells.

The plasmids expressing the S. flexneri O antigen with (SEQ ID NO: 29) or without (SEQ ID NO: 28) Z3206 were transformed into SCM3 cells (FIG. 10). Traces at late elution volumes shows a difference between the curves of the two samples containing the S. flexneri O antigen +/–Z3206 (FIG. 12). This difference in the elution pattern can be explained by a different oligosaccharide structure carrying a different monosaccharide at the reducing end: GlcNAc or GalNAc depending on the presence of the epimerase (Z3206).

Example 11

Analysis of pglB Specificity by Production and Characterization of Bioconjugate Produced from S. flexneri 6+/–Z3206

Figure 13:
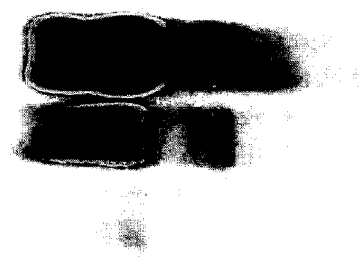
FIG. 13 shows Western blot of Nickel purified proteins from *E. coli* cells expressing EPA, pglB and *S. flexneri* 6 O-antigen+/−Z3206
Figure 13:
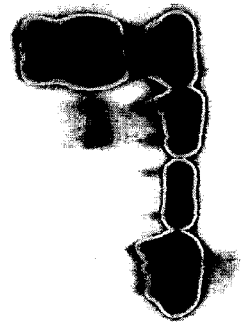

To assess whether PglB can transfer oligosaccharides having GlcNAc (S. flexneri 6 O-antigen) at the reducing end to the carrier protein EPA Nickel purified extracts from E. coli cells expressing EPA (SEQ ID NO: 25), Pg1B (SEQ ID NO: 26) and S. flexneri 6 O-antigen+/–Z3206 (SEQ ID NO: 29/SEQ ID NO: 28) were analyzed by western blot using anti EPA and anti type VI antibodies. The S. flexneri O6 antigen with and without GalNAc at the reducing end was transferred to EPA by PglB as detected by antiEPA and anti VI antisera (FIG. 13).

The O antigen is still produced and detected, but with lower production yield, which indicates that the efficiency of polysaccharide production without the epimerase is lower.

While this invention has been particularly shown and described with references to embodiments thereof, it will be understood by those skilled in the art that various changes in form and detail may be made therein without departing from the scope of the invention encompassed by the claims. Such various changes that will be understood by those skilled in the art as covered within the scope of the invention include, in particular, N-glycosylated proteins and bioconjugates comprising a glycan other than those from E. coli and S. flexneri with GalNAc at the reducing terminus.

The invention claimed is:

1. A recombinant prokaryotic biosynthetic system comprising:
   (i) a nucleic acid encoding an epimerase that synthesizes N-acetylgalactosamine on undecaprenyl pyrophosphate, wherein said epimerase comprises the amino acid sequence of SEQ ID NO. 2;
   (ii) a nucleic acid encoding a glycosyltransferase that participates in the assembly of an oligo- or polysaccharide on a lipid carrier;
   (iii) a nucleic acid encoding an oligosaccharyl transferase; and
   (iv) a nucleic acid encoding a protein comprising one or more of an introduced consensus sequence, D/E-X-N-Z-S/T (SEQ ID NO:31), wherein X and Z can be any natural amino acid except proline.

2. The recombinant prokaryotic biosynthetic system of claim 1, wherein said oligosaccharyl transferase is from *Campylobacter jejuni*.

3. The recombinant prokaryotic biosynthetic system of claim 1, wherein said protein is *P. aeruginosa* exoprotein.

4. The recombinant prokaryotic biosynthetic system of claim 1, wherein said oligo- or polysaccharide is from a Gram-negative bacterium.

5. The recombinant prokaryotic biosynthetic system of claim 4, wherein said oligo- or polysaccharide is from *Shigella flexneri*.

6. The recombinant prokaryotic biosynthetic system of claim 5, wherein said oligo- or polysaccharide is from *Shigella flexneri* 6.

7. The recombinant prokaryotic biosynthetic system of claim 1, wherein said oligo- or polysaccharide comprises a structure:

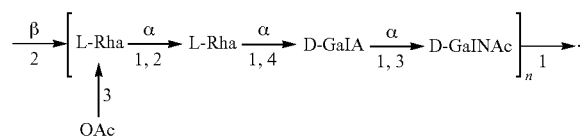

8. The recombinant prokaryotic biosynthetic system of claim 4, wherein said oligo- or polysaccharide is from *E. coli*.

9. The recombinant prokaryotic biosynthetic system of claim 8, wherein said oligo- or polysaccharide is from *E. coli* 0157.

10. The recombinant prokaryotic biosynthetic system of claim 1, wherein said oligo- or polysaccharide comprises a structure, α-D-PerNAc-α-L-Fuc-β-D-Glc-α-D-GalNAc.

11. A method of producing an N-linked glycosylated protein, comprising:
   a.) introducing into a host organism:
      i.) a nucleic acid encoding an epimerase that synthesizes N-acetylgalactosamine on undecaprenyl pyrophosphate, wherein said epimerase comprises the amino acid sequence of SEQ ID NO. 2;
      ii.) a nucleic acid encoding a glycosyltransferase that participates in the assembly of an oligo- or polysaccharide on a lipid carrier;
      iii.) a nucleic acid encoding an oligosaccharyl transferase; and
      iv.) a nucleic acid encoding a protein comprising one or more of an introduced consensus sequence, D/E-X-N-Z-S/T (SEQ ID NO:31), wherein X and Z can be any natural amino acid except proline; and
   b.) culturing said host organism until at least one N-glycosylated protein is produced.

12. The method of claim 11, wherein said oligosaccharyl transferase is from *Campylobacter jejuni*.

13. The method of claim 11, wherein said protein is *P. aeruginosa* exoprotein.

14. The method of claim 11, wherein said oligo- or polysaccharide is from a Gram-negative bacterium.

15. The method of claim 14, wherein said oligo- or polysaccharide is from *Shigella flexneri*.

16. The method of claim 15, wherein said oligo- or polysaccharide is from *Shigella flexneri* 6.

17. The method of claim 11, wherein said oligo- or polysaccharide comprises a structure:

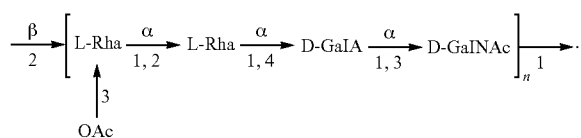

18. The method of claim 14, wherein said oligo- or polysaccharide is from *E. coli*.

19. The method of claim 18, wherein said oligo- or polysaccharide is from *E. coli* 0157.

20. The method of claim 11, wherein said oligo- or polysaccharide comprises a structure, α-D-PerNAc-α-L-Fuc-β-D-Glc-α-D-GalNAc.

* * * * *

SEQUENCE LISTING

<160> NUMBER OF SEQ ID NOS: 31

<210> SEQ ID NO 1
<211> LENGTH: 993
<212> TYPE: DNA
<213> ORGANISM: Escherichia coli

<400> SEQUENCE: 1

```
atgaacgata acgttttgct cataggagct tccggattcg taggaacccg actacttgaa      60
acggcaattg ctgactttaa tatcaagaac ctggacaaac agcagagcca cttttatcca     120
gaaatcacac agattggcga tgttcgcgat caacaggcac tcgaccaggc gttagtcggt     180
tttgacactg ttgtactact ggcagcggaa caccgcgatg acgtcagccc tacttctctc     240
tattatgatg tcaacgttca gggtacccgc aatgtgctgg cggccatgga aaaaaatggc     300
gttaaaaata tcatctttac cagttccgtt gctgtttatg gtttgaacaa acacaaccct     360
gacgaaaacc atccacacga ccctttcaac cactacggca aaagtaagtg gcaggcagag     420
gaagtgctgc gtgaatggta taacaaagca ccaacagaac gttcattaac catcatccgt     480
cctaccgtta tcttcggtga acgcaaccgc ggtaacgtct ataacttgct gaaacagatc     540
gctggcggca gtttatgat ggtgggcgca gggactaact ataagtccat ggcttatgtt     600
ggaaacattg ttgagtttat caagtacaaa ctgaagaatg ttgccgcagg ttatgaggtt     660
tataactacg ttgataagcc agacctgaac atgaaccagt tggttgctga agttgaacaa     720
agcctgaaca aaaagatccc ttctatgcac ttgccttacc cactaggaat gctgggtgga     780
tattgctttg atatcctgag caaaattacg ggcaaaaaat acgctgtcag ctcagtgcgc     840
gtgaaaaaat tctgcgcaac aacacagttt gacgcaacga aagtgcattc ttcaggtttt     900
gtggcaccgt atacgctgtc gcaaggtctg gatcgaacac tgcagtatga attcgttcat     960
gccaaaaaag acgacataac gtttgtttct gag                                   993
```

<210> SEQ ID NO 2
<211> LENGTH: 331
<212> TYPE: PRT
<213> ORGANISM: Escherichia coli

<400> SEQUENCE: 2

```
Met Asn Asp Asn Val Leu Leu Ile Gly Ala Ser Gly Phe Val Gly Thr
  1               5                  10                  15

Arg Leu Leu Glu Thr Ala Ile Ala Asp Phe Asn Ile Lys Asn Leu Asp
             20                  25                  30

Lys Gln Gln Ser His Phe Tyr Pro Glu Ile Thr Gln Ile Gly Asp Val
         35                  40                  45

Arg Asp Gln Gln Ala Leu Asp Gln Ala Leu Val Gly Phe Asp Thr Val
     50                  55                  60

Val Leu Leu Ala Ala Glu His Arg Asp Asp Val Ser Pro Thr Ser Leu
 65                  70                  75                  80

Tyr Tyr Asp Val Asn Val Gln Gly Thr Arg Asn Val Leu Ala Ala Met
                 85                  90                  95

Glu Lys Asn Gly Val Lys Asn Ile Ile Phe Thr Ser Ser Val Ala Val
            100                 105                 110

Tyr Gly Leu Asn Lys His Asn Pro Asp Glu Asn His Pro His Asp Pro
        115                 120                 125

Phe Asn His Tyr Gly Lys Ser Lys Trp Gln Ala Glu Glu Val Leu Arg
    130                 135                 140
```

```
Glu Trp Tyr Asn Lys Ala Pro Thr Glu Arg Ser Leu Thr Ile Ile Arg
145                 150                 155                 160

Pro Thr Val Ile Phe Gly Glu Arg Asn Arg Gly Asn Val Tyr Asn Leu
                165                 170                 175

Leu Lys Gln Ile Ala Gly Gly Lys Phe Met Met Val Gly Ala Gly Thr
            180                 185                 190

Asn Tyr Lys Ser Met Ala Tyr Val Gly Asn Ile Val Glu Phe Ile Lys
        195                 200                 205

Tyr Lys Leu Lys Asn Val Ala Ala Gly Tyr Glu Val Tyr Asn Tyr Val
    210                 215                 220

Asp Lys Pro Asp Leu Asn Met Asn Gln Leu Val Ala Glu Val Glu Gln
225                 230                 235                 240

Ser Leu Asn Lys Lys Ile Pro Ser Met His Leu Pro Tyr Pro Leu Gly
                245                 250                 255

Met Leu Gly Gly Tyr Cys Phe Asp Ile Leu Ser Lys Ile Thr Gly Lys
            260                 265                 270

Lys Tyr Ala Val Ser Ser Val Arg Val Lys Phe Cys Ala Thr Thr
    275                 280                 285

Gln Phe Asp Ala Thr Lys Val His Ser Ser Gly Phe Val Ala Pro Tyr
290                 295                 300

Thr Leu Ser Gln Gly Leu Asp Arg Thr Leu Gln Tyr Glu Phe Val His
305                 310                 315                 320

Ala Lys Lys Asp Asp Ile Thr Phe Val Ser Glu
                325                 330

<210> SEQ ID NO 3
<211> LENGTH: 993
<212> TYPE: DNA
<213> ORGANISM: Escherichia coli

<400> SEQUENCE: 3
atgaacgata acgttttgct cataggagct tccggattcg taggaacccg actacttgaa      60
acggcaattg ctgactttaa tatcaagaac ctggacaaac agcagagcca cttttatcca     120
gaaatcacac agattggtga tgttcgtgat caacaggcac tcgaccaggc gttagccggt     180
tttgacactg ttgtgctact ggcagcggaa caccgcgatg acgtcagccc tacttctctc     240
tattatgatg tcaacgttca gggtacccgc aatgtgctgg cggccatgga aaaaaatggc     300
gttaaaaata tcatctttac cagttccgtt gctgtttatg gtttgaacaa acacaaccct     360
gacgaaaacc atccacacga tcctttcaac cactacggca aaagtaagtg gcaggcagag     420
gaagtgctgc gtgaatggta taacaaagca ccaacagaac gttcattaac catcatccgt     480
cctaccgtta tcttcggtga acggaaccgc ggtaacgtct ataacttgct gaaacagatc     540
gctggcggca gtttatgat ggtgggcgca gggactaact ataagtccat ggcttatgtt     600
ggaaacattg ttgagtttat caagtacaaa ctgaagaatg ttgccgcagg ttacgaggtt     660
tataactacg ttgataagcc agacctgaac atgaaccagt tggttgctga agttgaacaa     720
agcctgaaca aaaagatccc ttctatgcac ttgccttacc cactaggaat gctgggtgga     780
tattgctttg atatcctgag caaaattacg ggcaaaaat acgctgtcag ctctgtgcgc     840
gtgaaaaaat tctgcgcaac aacacagttt gacgcaacga agtgcattc ttcaggtttt     900 gtggcaccgt atacgctgtc gcaaggtctg gatcgaactc tgcagtatga attcgtccat     960
gccaaaaaag acgacataac gtttgtttct gag                                 993
```

```
<210> SEQ ID NO 4
<211> LENGTH: 331
<212> TYPE: PRT
<213> ORGANISM: Escherichia coli

<400> SEQUENCE: 4

Met Asn Asp Asn Val Leu Leu Ile Gly Ala Ser Gly Phe Val Gly Thr
1               5                   10                  15

Arg Leu Leu Glu Thr Ala Ile Ala Asp Phe Asn Ile Lys Asn Leu Asp
            20                  25                  30

Lys Gln Gln Ser His Phe Tyr Pro Glu Ile Thr Gln Ile Gly Asp Val
        35                  40                  45

Arg Asp Gln Gln Ala Leu Asp Gln Ala Leu Ala Gly Phe Asp Thr Val
    50                  55                  60

Val Leu Ala Ala Glu His Arg Asp Asp Val Ser Pro Thr Ser Leu
65                  70                  75                  80

Tyr Tyr Asp Val Asn Val Gln Gly Thr Arg Asn Val Leu Ala Ala Met
                85                  90                  95

Glu Lys Asn Gly Val Lys Asn Ile Ile Phe Thr Ser Ser Val Ala Val
            100                 105                 110

Tyr Gly Leu Asn Lys His Asn Pro Asp Glu Asn His Pro His Asp Pro
        115                 120                 125

Phe Asn His Tyr Gly Lys Ser Lys Trp Gln Ala Glu Glu Val Leu Arg
    130                 135                 140

Glu Trp Tyr Asn Lys Ala Pro Thr Glu Arg Ser Leu Thr Ile Ile Arg
145                 150                 155                 160

Pro Thr Val Ile Phe Gly Glu Arg Asn Arg Gly Asn Val Tyr Asn Leu
                165                 170                 175

Leu Lys Gln Ile Ala Gly Gly Lys Phe Met Met Val Gly Ala Gly Thr
            180                 185                 190

Asn Tyr Lys Ser Met Ala Tyr Val Gly Asn Ile Val Glu Phe Ile Lys
        195                 200                 205

Tyr Lys Leu Lys Asn Val Ala Ala Gly Tyr Glu Val Tyr Asn Tyr Val
    210                 215                 220

Asp Lys Pro Asp Leu Asn Met Asn Gln Leu Val Ala Glu Val Glu Gln
225                 230                 235                 240

Ser Leu Asn Lys Lys Ile Pro Ser Met His Leu Pro Tyr Pro Leu Gly
                245                 250                 255

Met Leu Gly Gly Tyr Cys Phe Asp Ile Leu Ser Lys Ile Thr Gly Lys
            260                 265                 270

Lys Tyr Ala Val Ser Ser Val Arg Val Lys Lys Phe Cys Ala Thr Thr
        275                 280                 285

Gln Phe Asp Ala Thr Lys Val His Ser Ser Gly Phe Val Ala Pro Tyr
    290                 295                 300

Thr Leu Ser Gln Gly Leu Asp Arg Thr Leu Gln Tyr Glu Phe Val His
305                 310                 315                 320

Ala Lys Lys Asp Asp Ile Thr Phe Val Ser Glu
                325                 330

<210> SEQ ID NO 5
<211> LENGTH: 993
<212> TYPE: DNA
<213> ORGANISM: Escherichia coli

<400> SEQUENCE: 5
atgaacgata acgttttgct cataggagct tccggattcg taggaacccg actacttgaa    60
```

```
acggcaattg ctgactttaa tatcaagaac ctggacaaac agcagagcca ctttatcca      120 gaaatcacac agattggtga tgttcgtgat caacaggcac tcgaccaggc gttagccggt      180
tttgacactg ttgtactact ggcagcggaa caccgcgatg acgtcagccc tacttctctc      240
tattatgatg tcaacgttca gggtacccgc aatgtgctgg cggccatgga aaaaaatggc      300
gttaaaaata tcatctttac cagttccgtt gctgtttatg gtttgaacaa cacaaccct      360 gacgaaaacc atccacacga ccctttcaac cactacggca aaagcaagtg gcaggcggag      420
gaagtgctgc gtgaatggta taacaaagca ccaacagaac gttcattaac tatcatccgt      480
cctaccgtta tcttcggtga acgcaaccgc ggtaacgtct ataacttgct gaaacagatc      540
gctggcggca gtttatgat ggtgggcgca gggactaact ataagtccat ggcttatgtt      600
ggaaacattg tgagttat caagtacaaa ctgaagaatg ttgccgcagg ttacgaggtt      660
tataactacg ttgataagcc agacctgaac atgaaccagt tggttgctga agttgaacaa      720
agcctgaaca aaaagatccc ttctatgcac ttgccttacc cactaggaat gctgggtgga      780
tattgctttg atatcctgag caaaattacg ggcaaaaaat acgctgtcag ctctgtgcgc      840
gtgaaaaaat tctgcgcaac aacacagttt gacgcaacga aagtgcattc ttcaggtttt      900
gtggcaccgt atacgctgtc gcaaggtctg gatcgaactc tgcagtatga attcgtccat      960
gccaaaaaag acgacataac gtttgtttct gag                                   993
```

```
<210> SEQ ID NO 6
<211> LENGTH: 331
<212> TYPE: PRT
<213> ORGANISM: Escherichia coli

<400> SEQUENCE: 6

Met Asn Asp Asn Val Leu Leu Ile Gly Ala Ser Gly Phe Val Gly Thr
 1               5                   10                  15

Arg Leu Leu Glu Thr Ala Ile Ala Asp Phe Asn Ile Lys Asn Leu Asp
                20                  25                  30

Lys Gln Gln Ser His Phe Tyr Pro Glu Ile Thr Gln Ile Gly Asp Val
            35                  40                  45

Arg Asp Gln Gln Ala Leu Asp Gln Ala Leu Ala Gly Phe Asp Thr Val
        50                  55                  60

Val Leu Ala Ala Glu His Arg Asp Asp Val Ser Pro Thr Ser Leu
 65                  70                  75                  80

Tyr Tyr Asp Val Asn Val Gln Gly Thr Arg Asn Val Leu Ala Ala Met
                85                  90                  95

Glu Lys Asn Gly Val Lys Asn Ile Ile Phe Thr Ser Ser Val Ala Val
                100                 105                 110

Tyr Gly Leu Asn Lys His Asn Pro Asp Glu Asn His Pro His Asp Pro
            115                 120                 125

Phe Asn His Tyr Gly Lys Ser Lys Trp Gln Ala Glu Glu Val Leu Arg
        130                 135                 140

Glu Trp Tyr Asn Lys Ala Pro Thr Glu Arg Ser Leu Thr Ile Ile Arg
145                 150                 155                 160

Pro Thr Val Ile Phe Gly Glu Arg Asn Arg Gly Asn Val Tyr Asn Leu
                165                 170                 175

Leu Lys Gln Ile Ala Gly Gly Lys Phe Met Met Val Gly Ala Gly Thr
            180                 185                 190

Asn Tyr Lys Ser Met Ala Tyr Val Gly Asn Ile Val Glu Phe Ile Lys
        195                 200                 205
```

Tyr Lys Leu Lys Asn Val Ala Ala Gly Tyr Glu Val Tyr Asn Tyr Val
            210                 215                 220

Asp Lys Pro Asp Leu Asn Met Asn Gln Leu Val Ala Glu Val Glu Gln
225                 230                 235                 240

Ser Leu Asn Lys Lys Ile Pro Ser Met His Leu Pro Tyr Pro Leu Gly
                245                 250                 255

Met Leu Gly Gly Tyr Cys Phe Asp Ile Leu Ser Lys Ile Thr Gly Lys
            260                 265                 270

Lys Tyr Ala Val Ser Ser Val Arg Val Lys Lys Phe Cys Ala Thr Thr
        275                 280                 285

Gln Phe Asp Ala Thr Lys Val His Ser Ser Gly Phe Val Ala Pro Tyr
    290                 295                 300

Thr Leu Ser Gln Gly Leu Asp Arg Thr Leu Gln Tyr Glu Phe Val His
305                 310                 315                 320

Ala Lys Lys Asp Asp Ile Thr Phe Val Ser Glu
                325                 330

<210> SEQ ID NO 7
<211> LENGTH: 993
<212> TYPE: DNA
<213> ORGANISM: Shigella boydii

<400> SEQUENCE: 7
atgaacgata acgttttgct cataggagct tccggattcg taggaacccg actacttgaa     60
acggcaattg ctgactttaa tatcaagaac ctggacaaac agcagagcca tttttatcca    120
gcaatcacac agattggcga tgttcgtgat caacaggcac tcgaccaggc gttagccggt    180
tttgacactg ttgtactact ggcagcggaa caccgcgatg acgtcagccc tacttctctc    240
tattatgatg tcaacgttca gggtacccgc aatgtgctgg cggccatgga aaaaaatggc    300
gttaaaaata tcatctttac cagttccgtt gctgtttatg gtttgaacaa acacaaccct    360
gacgaaaacc atccacacga ccctttcaac cactacggca aaagtaagtg gcaggcagag    420
gaagtgctgc gtgaatggta taacaaagca ccaacagaac gttcattaac catcatccgt    480
cctaccgtta tcttcggtga acgcaaccgc ggtaacgtct ataacttgct gaaacagatc    540
gctggcggca gtttatgat ggtgggcgca gggactaact ataagtccat ggcttatgtt    600
ggaaacattg ttgagtttat caagtacaaa ctgaagaatg ttgccgcagg ttatgaggtt    660
tataactatg ttgataagcc agacctgaac atgaaccagt tggttgctga agttgaacaa    720
agcctgaaca aaaagatccc ttctatgcac ttgccttacc cactaggaat gctgggtgga    780
tattgctttg atatcctgag caaaattacg ggcaaaaaat acgctgtcag ctctgtgcgc    840
gtgaaaaaat tctgcgcaac aacacagttt gacgcaacga agtgcattc ttcaggtttt    900 gtggcaccgt atacgctgtc gcaaggtctg gatcgaactc tgcagtatga attcgtccat    960
gccaaaaaag acgacataac gtttgtttct gag                                 993

<210> SEQ ID NO 8
<211> LENGTH: 331
<212> TYPE: PRT
<213> ORGANISM: Shigella boydii

<400> SEQUENCE: 8

Met Asn Asp Asn Val Leu Leu Ile Gly Ala Ser Gly Phe Val Gly Thr
1               5                   10                  15

Arg Leu Leu Glu Thr Ala Ile Ala Asp Phe Asn Ile Lys Asn Leu Asp

```
            20                  25                  30
Lys Gln Gln Ser His Phe Tyr Pro Ala Ile Thr Gln Ile Gly Asp Val
         35                  40                  45
Arg Asp Gln Gln Ala Leu Asp Gln Ala Leu Ala Gly Phe Asp Thr Val
     50                  55                  60
Val Leu Leu Ala Ala Glu His Arg Asp Asp Val Ser Pro Thr Ser Leu
 65                  70                  75                  80
Tyr Tyr Asp Val Asn Val Gln Gly Thr Arg Asn Val Leu Ala Ala Met
                 85                  90                  95
Glu Lys Asn Gly Val Lys Asn Ile Ile Phe Thr Ser Val Ala Val
            100                 105                 110
Tyr Gly Leu Asn Lys His Asn Pro Asp Glu Asn His Pro His Asp Pro
         115                 120                 125
Phe Asn His Tyr Gly Lys Ser Lys Trp Gln Ala Glu Glu Val Leu Arg
     130                 135                 140
Glu Trp Tyr Asn Lys Ala Pro Thr Glu Arg Ser Leu Thr Ile Ile Arg
145                 150                 155                 160
Pro Thr Val Ile Phe Gly Glu Arg Asn Arg Gly Asn Val Tyr Asn Leu
                165                 170                 175
Leu Lys Gln Ile Ala Gly Gly Lys Phe Met Met Val Gly Ala Gly Thr
            180                 185                 190
Asn Tyr Lys Ser Met Ala Tyr Val Gly Asn Ile Val Glu Phe Ile Lys
         195                 200                 205
Tyr Lys Leu Lys Asn Val Ala Ala Gly Tyr Glu Val Tyr Asn Tyr Val
     210                 215                 220
Asp Lys Pro Asp Leu Asn Met Asn Gln Leu Val Ala Glu Val Glu Gln
225                 230                 235                 240
Ser Leu Asn Lys Lys Ile Pro Ser Met His Leu Pro Tyr Pro Leu Gly
                245                 250                 255
Met Leu Gly Gly Tyr Cys Phe Asp Ile Leu Ser Lys Ile Thr Gly Lys
            260                 265                 270
Lys Tyr Ala Val Ser Ser Val Arg Val Lys Lys Phe Cys Ala Thr Thr
         275                 280                 285
Gln Phe Asp Ala Thr Lys Val His Ser Ser Gly Phe Val Ala Pro Tyr
     290                 295                 300
Thr Leu Ser Gln Gly Leu Asp Arg Thr Leu Gln Tyr Glu Phe Val His
305                 310                 315                 320
Ala Lys Lys Asp Asp Ile Thr Phe Val Ser Glu
                325                 330
```

<210> SEQ ID NO 9
<211> LENGTH: 993
<212> TYPE: DNA
<213> ORGANISM: Salmonella enterica

<400> SEQUENCE: 9

```
atgaacgata acgttttgct cattggtgct tccggattcg taggaacccg actccttgaa      60
acggcagtgg atgattttaa tatcaagaac ctggataaac agcaaagcca tttctaccca     120
gagattacac acattggcga tgttcgtgac caacaaatcc ttgaccagac gttggtgggt     180
tttgacaccg tagtactatt ggctgcggag catcgtgatg atgttagtcc tacctcgctt     240
tattatgatg tcaacgtcca gggaacgcgt aatgtactgg cggcgatgga aaaaaatggt     300
gtaaaaaata tcattttttac cagttccgtt gcagtttatg gactcaacaa gaaaaatcct     360
```

```
gacgaaacgc accctcacga tcccttaat cattacggaa aaagtaaatg gcaagcagaa    420
gaagttctgc gtgagtggca tgctaaagcg ccgaatgagc gttctttgac cataattcgt    480
cctaccgtta ttttcgggga gcgtaaccgc ggtaatgtat acaatctctt gaaacagatc    540
gctggtggta aatttgcgat ggttggtccg gaactaact ataaatcaat ggcttatgtt      600
ggtaatatcg ttgagtttat caaattcaaa ctcaagaatg ttacggcggg ctatgaagtt     660
tataattatg ttgataaacc tgatctgaat atgaatcaat tggttgctga agtagagcag     720
agcctgggca aaaaatacc atcgatgcac cttccatatc cattaggtat gctgggggt      780 tactgtttcg atatcctgag caaagtaacg ggcaagaagt acgctgtaag ttcggttcgt    840
gttaaaaaat tctgtgcgac aacgcagttt gatgcaacaa aagtgcattc ttctggtttt     900
gttgcgccat acaccttatc tcaggggttg gatcgtacac tgcaatatga atttgttcat     960
gcaaagaaag atgacattac attcgtttca gag                                  993
```

<210> SEQ ID NO 10
<211> LENGTH: 331
<212> TYPE: PRT
<213> ORGANISM: Salmonella enterica

<400> SEQUENCE: 10

```
Met Asn Asp Asn Val Leu Leu Ile Gly Ala Ser Gly Phe Val Gly Thr
1               5                   10                  15

Arg Leu Leu Glu Thr Ala Val Asp Asp Phe Asn Ile Lys Asn Leu Asp
            20                  25                  30

Lys Gln Gln Ser His Phe Tyr Pro Glu Ile Thr His Ile Gly Asp Val
        35                  40                  45

Arg Asp Gln Gln Ile Leu Asp Gln Thr Leu Val Gly Phe Asp Thr Val
    50                  55                  60

Val Leu Leu Ala Ala Glu His Arg Asp Asp Val Ser Pro Thr Ser Leu
65                  70                  75                  80

Tyr Tyr Asp Val Asn Val Gln Gly Thr Arg Asn Val Leu Ala Ala Met
                85                  90                  95

Glu Lys Asn Gly Val Lys Asn Ile Ile Phe Thr Ser Ser Val Ala Val
            100                 105                 110

Tyr Gly Leu Asn Lys Lys Asn Pro Asp Glu Thr His Pro His Asp Pro
        115                 120                 125

Phe Asn His Tyr Gly Lys Ser Lys Trp Gln Ala Glu Glu Val Leu Arg
    130                 135                 140

Glu Trp His Ala Lys Ala Pro Asn Glu Arg Ser Leu Thr Ile Ile Arg
145                 150                 155                 160

Pro Thr Val Ile Phe Gly Glu Arg Asn Arg Gly Asn Val Tyr Asn Leu
                165                 170                 175

Leu Lys Gln Ile Ala Gly Gly Lys Phe Ala Met Val Gly Pro Gly Thr
            180                 185                 190

Asn Tyr Lys Ser Met Ala Tyr Val Gly Asn Ile Val Glu Phe Ile Lys
        195                 200                 205

Phe Lys Leu Lys Asn Val Thr Ala Gly Tyr Glu Val Tyr Asn Tyr Val
    210                 215                 220

Asp Lys Pro Asp Leu Asn Met Asn Gln Leu Ala Glu Val Glu Gln
225                 230                 235                 240

Ser Leu Gly Lys Lys Ile Pro Ser Met His Leu Pro Tyr Pro Leu Gly
                245                 250                 255

Met Leu Gly Gly Tyr Cys Phe Asp Ile Leu Ser Lys Val Thr Gly Lys
```

```
                260             265             270
Lys Tyr Ala Val Ser Ser Val Arg Val Lys Lys Phe Cys Ala Thr Thr
                275             280             285

Gln Phe Asp Ala Thr Lys Val His Ser Ser Gly Phe Val Ala Pro Tyr
        290             295             300

Thr Leu Ser Gln Gly Leu Asp Arg Thr Leu Gln Tyr Glu Phe Val His
305             310             315             320

Ala Lys Lys Asp Asp Ile Thr Phe Val Ser Glu
                325             330
```

<210> SEQ ID NO 11
<211> LENGTH: 987
<212> TYPE: DNA
<213> ORGANISM: Campylobacter jejuni

<400> SEQUENCE: 11

```
atgaaaattc ttattagcgg tggtgcaggt tatataggtt ctcatacttt aagacaattt      60
ttaaaaacag atcatgaaat ttgtgtttta gataatcttt ctaagggttc taaaatcgca     120
atagaagatt tgcaaaaaac aagagctttt aaattttcg aacaagattt aagtgatttt      180
caaggcgtaa aagcattgtt tgagagagaa aaatttgacg ctattgtgca ttttgcagca     240
agcattgaag ttttgaaag tatgcaaaat cctttaaaat attatatgaa caacactgtt      300
aatacgacaa atctcatcga aacttgtttg caaactggag tgaataaatt tatatttct     360
tcaacggcgg ccacttatgg cgaaccacaa actcccgttg tgagcgaaac aagtccttta     420
gcacctatta tcctatgg gcgtagtaag cttatgagtg aagaagtttt gcgtgatgca      480
agtatggcaa atcctgaatt taagcattgt attttaagat attttaatgt gcaggtgct     540
tgtatggatt atactttagg acaacgctat ccaaaagcga ctttgcttat aaaagttgca     600
gctgaatgtg ccgcaggaaa acgtgataaa cttttcatat ttggcgatga ttatgataca     660
aaagatggta cttgcataag agattttatc catgtagatg atatttcaag tgcacattta     720
gcggctttgg attatttaaa agagaatgaa agcaatgttt ttaatgtagg ttatggacat     780
ggttttagcg taaaagaagt gattgaagcg atgaaaaaag ttagcggagt ggattttaaa     840
gtagaacttg ccccacgccg tgcgggtgat cctagtgtat tgatttctga tgcaagtaaa     900
atcagaaatc ttacttcttg gcagcctaaa tatgatgatt tagagcttat ttgtaaatct     960
gcttttgatt gggaaaaaca gtgttaa                                         987
```

<210> SEQ ID NO 12
<211> LENGTH: 328
<212> TYPE: PRT
<213> ORGANISM: Campylobacter jejuni

<400> SEQUENCE: 12

```
Met Lys Ile Leu Ile Ser Gly Gly Ala Gly Tyr Ile Gly Ser His Thr
1               5                   10                  15

Leu Arg Gln Phe Leu Lys Thr Asp His Glu Ile Cys Val Leu Asp Asn
            20                  25                  30

Leu Ser Lys Gly Ser Lys Ile Ala Ile Glu Asp Leu Gln Lys Thr Arg
        35                  40                  45

Ala Phe Lys Phe Phe Glu Gln Asp Leu Ser Asp Phe Gln Gly Val Lys
    50                  55                  60

Ala Leu Phe Glu Arg Glu Lys Phe Asp Ala Ile Val His Phe Ala Ala
65                  70                  75                  80
```

```
Ser Ile Glu Val Phe Glu Ser Met Gln Asn Pro Leu Lys Tyr Tyr Met
                85                  90                  95

Asn Asn Thr Val Asn Thr Thr Asn Leu Ile Glu Thr Cys Leu Gln Thr
            100                 105                 110

Gly Val Asn Lys Phe Ile Phe Ser Ser Thr Ala Ala Thr Tyr Gly Glu
        115                 120                 125

Pro Gln Thr Pro Val Val Ser Glu Thr Ser Pro Leu Ala Pro Ile Asn
    130                 135                 140

Pro Tyr Gly Arg Ser Lys Leu Met Ser Glu Glu Val Leu Arg Asp Ala
145                 150                 155                 160

Ser Met Ala Asn Pro Glu Phe Lys His Cys Ile Leu Arg Tyr Phe Asn
                165                 170                 175

Val Ala Gly Ala Cys Met Asp Tyr Thr Leu Gly Gln Arg Tyr Pro Lys
            180                 185                 190

Ala Thr Leu Leu Ile Lys Val Ala Ala Glu Cys Ala Ala Gly Lys Arg
        195                 200                 205

Asp Lys Leu Phe Ile Phe Gly Asp Asp Tyr Asp Thr Lys Asp Gly Thr
    210                 215                 220

Cys Ile Arg Asp Phe Ile His Val Asp Ile Ser Ser Ala His Leu
225                 230                 235                 240

Ala Ala Leu Asp Tyr Leu Lys Glu Asn Glu Ser Asn Val Phe Asn Val
                245                 250                 255

Gly Tyr Gly His Gly Phe Ser Val Lys Glu Val Ile Glu Ala Met Lys
            260                 265                 270

Lys Val Ser Gly Val Asp Phe Lys Val Glu Leu Ala Pro Arg Arg Ala
        275                 280                 285

Gly Asp Pro Ser Val Leu Ile Ser Asp Ala Ser Lys Ile Arg Asn Leu
    290                 295                 300

Thr Ser Trp Gln Pro Lys Tyr Asp Asp Leu Glu Leu Ile Cys Lys Ser
305                 310                 315                 320

Ala Phe Asp Trp Glu Lys Gln Cys
                325

<210> SEQ ID NO 13
<211> LENGTH: 1017
<212> TYPE: DNA
<213> ORGANISM: Escherichia coli

<400> SEQUENCE: 13
atgagagttc tggttaccgg tggtagcggt tacattggaa gtcataccctg tgtgcaatta      60 ctgcaaaacg gtcatgatgt catcattctt gataacctct gtaacagtaa gcgcagcgta     120
ctgcctgtta tcgagcgttt aggcggcaaa catccaacgt tgttgaaggc gatattcgt      180 aacgaagcgt tgatgaccga tcctgcac gatcacgcta tcgacaccgt gatccacttc      240
gccgggctga agccgtggg cgaatcggta caaaaaccgc tggaatatta cgacaacaat      300
gtcaacggca ctctgcgcct gattagcgcc atgcgcgccg ctaacgtcaa aaacttttat     360
tttagctcct ccgccaccgt ttatggcgat cagcccaaaa ttccatacgt tgaaagcttc     420
ccgaccggca caccgcaaag cccttacggc aaaagcaagc tgatggtgga acagatcctc     480
accgatctgc aaaagcccca gccggactgg agcattgccc tgctgcgcta cttcaacccg     540
gttggcgcgc atccgtcggg cgatatgggc gaagatccgc aaggcattcc gaataacctg      600
atgccataca tcgcccaggt tgctgtaggc cgtcgcgact cgctggcgat ttttggtaac      660
gattatccga ccgaagatgg tactggcgta cgcgattaca tccacgtaat ggatctggcg      720
```

```
gacggtcacg tcgtggcgat ggaaaaactg gcgaacaagc caggcgtaca catctacaac    780
ctcggcgctg gcgtaggcaa cagcgtgctg gacgtggtta atgccttcag caaagcctgc    840
ggcaaaccgg ttaattatca ttttgcaccg cgtcgcgagg gcgaccttcc ggcctactgg    900
gcggacgcca gcaaagccga ccgtgaactg aactggcgcg taacgcgcac actcgatgaa    960
atggcgcagg acacctggca ctggcagtca cgccatccac agggatatcc cgattaa     1017
```

<210> SEQ ID NO 14
<211> LENGTH: 338
<212> TYPE: PRT
<213> ORGANISM: Escherichia coli

<400> SEQUENCE: 14

```
Met Arg Val Leu Val Thr Gly Gly Ser Gly Tyr Ile Gly Ser His Thr
1               5                   10                  15

Cys Val Gln Leu Leu Gln Asn Gly His Asp Val Ile Ile Leu Asp Asn
            20                  25                  30

Leu Cys Asn Ser Lys Arg Ser Val Leu Pro Val Ile Glu Arg Leu Gly
        35                  40                  45

Gly Lys His Pro Thr Phe Val Glu Gly Asp Ile Arg Asn Glu Ala Leu
    50                  55                  60

Met Thr Glu Ile Leu His Asp His Ala Ile Asp Thr Val Ile His Phe
65                  70                  75                  80

Ala Gly Leu Lys Ala Val Gly Glu Ser Val Gln Lys Pro Leu Glu Tyr
                85                  90                  95

Tyr Asp Asn Asn Val Asn Gly Thr Leu Arg Leu Ile Ser Ala Met Arg
            100                 105                 110

Ala Ala Asn Val Lys Asn Phe Ile Phe Ser Ser Ser Ala Thr Val Tyr
        115                 120                 125

Gly Asp Gln Pro Lys Ile Pro Tyr Val Glu Ser Phe Pro Thr Gly Thr
    130                 135                 140

Pro Gln Ser Pro Tyr Gly Lys Ser Lys Leu Met Val Glu Gln Ile Leu
145                 150                 155                 160

Thr Asp Leu Gln Lys Ala Gln Pro Asp Trp Ser Ile Ala Leu Leu Arg
                165                 170                 175

Tyr Phe Asn Pro Val Gly Ala His Pro Ser Gly Asp Met Gly Glu Asp
            180                 185                 190

Pro Gln Gly Ile Pro Asn Asn Leu Met Pro Tyr Ile Ala Gln Val Ala
        195                 200                 205

Val Gly Arg Arg Asp Ser Leu Ala Ile Phe Gly Asn Asp Tyr Pro Thr
    210                 215                 220

Glu Asp Gly Thr Gly Val Arg Asp Tyr Ile His Val Met Asp Leu Ala
225                 230                 235                 240

Asp Gly His Val Val Ala Met Glu Lys Leu Ala Asn Lys Pro Gly Val
                245                 250                 255

His Ile Tyr Asn Leu Gly Ala Gly Val Gly Asn Ser Val Leu Asp Val
            260                 265                 270

Val Asn Ala Phe Ser Lys Ala Cys Gly Lys Pro Val Asn Tyr His Phe
        275                 280                 285

Ala Pro Arg Arg Glu Gly Asp Leu Pro Ala Tyr Trp Ala Asp Ala Ser
    290                 295                 300

Lys Ala Asp Arg Glu Leu Asn Trp Arg Val Thr Arg Thr Leu Asp Glu
305                 310                 315                 320
```

Met Ala Gln Asp Thr Trp His Trp Gln Ser Arg His Pro Gln Gly Tyr
                325                 330                 335

Pro Asp

<210> SEQ ID NO 15
<211> LENGTH: 1020
<212> TYPE: DNA
<213> ORGANISM: Escherichia coli

<400> SEQUENCE: 15

| | | |
|---|---|---|
| atggtgattt tcgtaacagg cggtgcagga tatattggat cccataccat acttgagtta | 60 |
| cttaataatg gtcatgatgt cgtttcgata gataattttg tcaattcctc tatagaatca | 120 |
| ttaaaaagag tagagcaaat aactaataag aaaattattt cttatcaagg tgatatccgt | 180 |
| gataaaaatc tacttgatga gatttttttca agacaccata tcgatgctgt aattcacttt | 240 |
| gcatcgttaa aatctgtagg tgagtctaag ttaaagccct tagagtatta ttctaataat | 300 |
| gttggtggaa ctttagtatt acttgaatgc atgaagagat ataacattaa taaaatgata | 360 |
| tttagctctt ctgctactgt ttatgggagt aacagtatcc ctccccatac ggaagataga | 420 |
| cgaattggtg aaactacaaa cccatatggg acatcgaaat ttataataga ataattttg | 480 |
| agtgattatt gtgatagtga taataataaa tcagtaattg cactgcgtta ctttaatcca | 540 |
| atcggagcac ataagtccgg gatgattggt gaaaatccta acgggatccc taataatctg | 600 |
| gttccttata tatctaaagt tgcacaaaat caacttcctg tattaaatat ttatggcaac | 660 |
| gattatccaa ctaaagatgg tacaggagta agagactata tacatgtctg tgatttggct | 720 |
| aaagggcatg ttaaagcatt agaatatatg ttttttaaatg atgtcaatta tgaagctttt | 780 |
| aatttaggta ctggtcaagg ttattctgtt ttagagatta taaaaatgtt tgagatagtc | 840 |
| actaaaaaga gtatacctgt tgctatttgt aatagacgtg agggggatgt tgcggagtca | 900 |
| tgggcgtctg ctgatttggc acataaaaag cttttcctgga aagcggaaaa aaatttgaaa | 960 |
| gaaatgatcg aagatgtatg gcgttggcaa acaaacaatc caaatggata taaaaaataa | 1020 |

<210> SEQ ID NO 16
<211> LENGTH: 339
<212> TYPE: PRT
<213> ORGANISM: Escherichia coli

<400> SEQUENCE: 16

Met Val Ile Phe Val Thr Gly Gly Ala Gly Tyr Ile Gly Ser His Thr
1               5                   10                  15

Ile Leu Glu Leu Leu Asn Asn Gly His Asp Val Val Ser Ile Asp Asn
                20                  25                  30

Phe Val Asn Ser Ser Ile Glu Ser Leu Lys Arg Val Glu Gln Ile Thr
            35                  40                  45

Asn Lys Lys Ile Ile Ser Tyr Gln Gly Asp Ile Arg Asp Lys Asn Leu
        50                  55                  60

Leu Asp Glu Ile Phe Ser Arg His His Ile Asp Ala Val Ile His Phe
65                  70                  75                  80

Ala Ser Leu Lys Ser Val Gly Glu Ser Lys Leu Lys Pro Leu Glu Tyr
                85                  90                  95

Tyr Ser Asn Asn Val Gly Gly Thr Leu Val Leu Leu Glu Cys Met Lys
                100                 105                 110

Arg Tyr Asn Ile Asn Lys Met Ile Phe Ser Ser Ser Ala Thr Val Tyr
            115                 120                 125

-continued

```
Gly Ser Asn Ser Ile Pro Pro His Thr Glu Asp Arg Arg Ile Gly Glu
            130                 135                 140

Thr Thr Asn Pro Tyr Gly Thr Ser Lys Phe Ile Ile Glu Ile Ile Leu
145                 150                 155                 160

Ser Asp Tyr Cys Asp Ser Asp Asn Asn Lys Ser Val Ile Ala Leu Arg
                165                 170                 175

Tyr Phe Asn Pro Ile Gly Ala His Lys Ser Gly Met Ile Gly Glu Asn
            180                 185                 190

Pro Asn Gly Ile Pro Asn Asn Leu Val Pro Tyr Ile Ser Lys Val Ala
        195                 200                 205

Gln Asn Gln Leu Pro Val Leu Asn Ile Tyr Gly Asn Asp Tyr Pro Thr
    210                 215                 220

Lys Asp Gly Thr Gly Val Arg Asp Tyr Ile His Val Cys Asp Leu Ala
225                 230                 235                 240

Lys Gly His Val Lys Ala Leu Glu Tyr Met Phe Leu Asn Asp Val Asn
                245                 250                 255

Tyr Glu Ala Phe Asn Leu Gly Thr Gly Gln Gly Tyr Ser Val Leu Glu
            260                 265                 270

Ile Val Lys Met Phe Glu Ile Val Thr Lys Lys Ser Ile Pro Val Ala
        275                 280                 285

Ile Cys Asn Arg Arg Glu Gly Asp Val Ala Glu Ser Trp Ala Ser Ala
    290                 295                 300

Asp Leu Ala His Lys Lys Leu Ser Trp Lys Ala Glu Lys Asn Leu Lys
305                 310                 315                 320

Glu Met Ile Glu Asp Val Trp Arg Trp Gln Thr Asn Asn Pro Asn Gly
                325                 330                 335

Tyr Lys Lys

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aaacccggga tgaacgataa cgttttgctc                                      30

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aaatctagat taagcgtaat ctggaacatc gtatgggtac tcagaaacaa acgttatgtc     60

<210> SEQ ID NO 19
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
aaaccatgga tgaaaattct tattagcgg                                       29
```

<210> SEQ ID NO 20
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaatctagat taagcgtaat ctggaacatc gtatgggtag cactgttttt cccaatc      57

<210> SEQ ID NO 21
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
aaaaagctag c                                                        11

<210> SEQ ID NO 22
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22 ccgcgcgg                                                             8

<210> SEQ ID NO 23
<211> LENGTH: 7794
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
tctacggggt ctgacgctca gtggaacgaa atcgatgagc tcgcacgaac ccagttgaca    60
taagcctgtt cggttcgtaa actgtaatgc aagtagcgta tgcgctcacg caactggtcc   120
agaaccttga ccgaacgcag cggtggtaac ggcgcagtgg cggttttcat ggcttgttat   180
gactgttttt ttgtacagtc tagcctcggg catccaagct agctaagcgc gttacgccgt   240
gggtcgatgt ttgatgttat ggaacagcaa cgatgttacg cagcagggta gtcgccctaa   300
aacaaagtta ggcagccgtt gtgctggtgc tttctagtag ttgttgtggg gtaggcagtc   360
agagctcgat ttgcttgtcg ccataataga ttcacaagaa ggattcgaca tgggtcaaag   420
tagcgatgaa gccaacgctc ccgttgcagg gcagtttgcg cttcccctga gtgccacctt   480
tggcttaggg gatcgcgtac gcaagaaatc tggtgccgct tggcagggtc aagtcgtcgg   540
ttggtattgc acaaaactca ctcctgaagg ctatgcggtc gagtccgaat cccacccagg   600
ctcagtgcaa atttatcctg tggctgcact tgaacgtgtg gcctaagcga tatcttagga   660
tctcccatcg gtgatgtcgg cgatataggc gccagcaacc gcacctgtgg cgccggtgat   720
gccggccacg atgcgtccgg cgtagaggat ctgctcatgt ttgacagctt atcatcgatg   780
cataatgtgc ctgtcaaatg gacgaagcag ggattctgca aacccatgc tactccgtca    840

```
agccgtcaat tgtctgattc gttaccaatt atgacaactt gacggctaca tcattcactt     900
tttcttcaca accggcacgg aactcgctcg gctggcccc ggtgcatttt ttaaataccc      960
gcgagaaata gagttgatcg tcaaaaccaa cattgcgacc gacggtggcg ataggcatcc    1020
gggtggtgct caaaagcagc ttcgcctggc tgatacgttg gtcctcgcgc cagcttaaga    1080
cgctaatccc taactgctgg cggaaaagat gtgacagacg cgacggcgac aagcaaacat    1140
gctgtgcgac gctggcgata tcaaaattgc tgtctgccag gtgatcgctg atgtactgac    1200
aagcctcgcg tacccgatta tccatcggtg gatggagcga ctcgttaatc gcttccatgc    1260
gccgcagtaa caattgctca agcagattta tcgccagcag ctccgaatag cgcccttccc    1320
cttgcccggc gttaatgatt tgcccaaaca ggtcgctgaa atgcggctgg tgcgcttcat    1380
ccgggcgaaa gaaccccgta ttggcaaata ttgacggcca gttaagccat tcatgccagt    1440
aggcgcgcgg acgaaagtaa acccactggt gataccattc gcgagcctcc ggatgacgac    1500
cgtagtgatg aatctctcct ggcgggaaca gcaaaatatc acccggtcgg caaacaaatt    1560
ctcgtccctg atttttcacc accccctgac cgcgaatggt gagattgaga atataaccTt    1620
tcattcccag cggtcggtcg ataaaaaaat cgagataacc gttggcctca atcggcgtta    1680
aacccgccac cagatgggca ttaaacgagt atcccggcag caggggatca ttttgcgctt    1740
cagccatact tttcatactc ccgccattca gagaagaaac caattgtcca tattgcatca    1800
gacattgccg tcactgcgtc ttttactggc tcttctcgct aaccaaaccg gtaacccgc     1860 ttattaaaag cattctgtaa caaagcggga ccaaagccat gacaaaaacg cgtaacaaaa    1920
gtgtctataa tcacggcaga aaagtccaca ttgattattt gcacggcgtc acactttgct    1980
atgccatagc attttatcc ataagattag cggatcctac ctgacgcttt ttatcgcaac     2040
tctctactgt ttctccatac ccgttttttt gggctagcag gaggaattca ccatggtacc    2100
cgggatgaac gataacgttt tgctcatagg agcttccgga ttcgtaggaa cccgactact    2160
tgaaacggca attgctgact ttaatatcaa gaacctggac aaacagcaga gccacttta    2220 tccagaaatc acacagattg gcgatgttcg cgatcaacag gcactcgacc aggcgttagt    2280
cggttttgac actgttgtac tactggcagc ggaacaccgc gatgacgtca gccctacttc    2340
tctctattat gatgtcaacg ttcagggtac ccgcaatgtg ctggcggcca tggaaaaaaa    2400
tggcgttaaa aatatcatct ttaccagttc cgttgctgtt tatggtttga acaaacacaa    2460
ccctgacgaa aaccatccac acgacccttt caaccactac ggcaaaagta agtggcaggc    2520
agaggaagtg ctgcgtgaat ggtataacaa agcaccaaca gaacgttcat taaccatcat    2580
ccgtcctacc gttatcttcg gtgaacgcaa ccgcggtaac gtctataact tgctgaaaca    2640
gatcgctggc ggcaagttta tgatggtggg cgcagggact aactataagt ccatggctta    2700
tgttggaaac attgttgagt ttatcaagta caaactgaag aatgttgccg caggttatga    2760
ggtttataac tacgttgata agccagacct gaacatgaac cagttggttg ctgaagttga    2820
acaaagcctg aacaaaaaga tcccttctat gcacttgcct tacccactag gaatgctggg    2880
tggatattgc tttgatatcc tgagcaaaat tacgggcaaa aaatacgctg tcagctcagt    2940
gcgcgtgaaa aaattctgcg caacaacaca gtttgacgca acgaaagtgc attcttcagg    3000
ttttgtggca ccgtatacgc tgtcgcaagg tctggatcga acactgcagt atgaattcgt    3060
tcatgccaaa aaagacgaca taacgtttgt ttctgagtac ccatacgatg ttccagatta    3120
cgcttaatct agagtcgacc tgcaggcatg caagcttggc tgttttggcg gatgagaaa    3180 gattttcagc ctgatacaga ttaaatcaga acgcagaagc ggtctgataa aacagaattt    3240
```

```
gcctggcggc agtagcgcgg tggtcccacc tgaccccatg ccgaactcag aagtgaaacg    3300
ccgtagcgcc gatggtagtg tggggtctcc ccatgcgaga gtagggaact gccaggcatc    3360
aaataaaacg aaaggctcag tcgaaagact gggcctttcg ttttatctgt tgtttgtcgg    3420
tgaacgctct cctgagtagg acaaatccgc cgggagcgga tttgaacgtt gcgaagcaac    3480
ggcccggagg gtggcgggca ggacgcccgc cataaactgc caggcatcaa attaagcaga    3540
aggccatcct gacggatggc cttttttgcgt ttctacaaac tcttccactc actacagcag    3600
agccatttaa acaacatccc ctcccccttt ccaccgcgtc agacgcccgt agcagcccgc    3660
tacgggcttt tcatgccct gccctagcgt ccaagcctca cggccgcgct cggcctctct    3720
ggcggccttc tggcgctgag gtctgcctcg tgaagaaggt gttgctgact cataccaggc    3780
ctgaatcgcc ccatcatcca gccagaaagt gaggagcca cggttgatga gctttgtt    3840 gtaggtggac cagttggtga ttttgaactt ttgctttgcc acggaacggt ctgcgttgtc    3900
gggaagatgc gtgatctgat ccttcaactc agcaaaagtt cgatttattc aacaaagccg    3960
ccgtcccgtc aagtcagcgt aatgctctgc cagtgttaca accaattaac caattctgat    4020
tagaaaaact catcgagcat caaatgaaac tgcaatttat tcatatcagg attatcaata    4080
ccatattttt gaaaaagccg tttctgtaat gaaggagaaa actcaccgag gcagttccat    4140
aggatggcaa gatcctggta tcggtctgcg attccgactc gtccaacatc aatacaacct    4200
attaatttcc cctcgtcaaa aataaggtta tcaagcgaga aatcaccatg agtgacgact    4260
gaatccggtg agaatggcaa aagctaaaaa ggccgtaata tccagctgaa cggtctggtt    4320
ataggtacat tgagcaactg actgaaatgc ctcaaaatgt tctttacgat gccattggga    4380
tatatcaacg gtggtatatc cagtgatttt tttctccatt ttagcttcct tagctcctga    4440
aaatctcgat aactcaaaaa atacgcccgg tagtgatctt atttcattat ggtgaaagtt    4500
ggaacctctt acgtgccgat caacgtctca ttttcgccaa aagttggccc agggcttccc    4560
ggtatcaaca gggacaccag gatttattta ttctgcgaag tgatcttccg tcacaggtat    4620
ttattcgaag acgaaagggc ctcgtgatac gcctattttt ataggttaat gtcatgataa    4680
taatggtttc ttagacgtca ggtggcactt ttcggggaaa tgtgcgcgcc cgcgttcctg    4740
ctggcgctgg gcctgtttct ggcgctggac ttcccgctgt ccgtcagca gcttttcgcc    4800 cacggccttg atgatcgcgg cggccttggc ctgcatatcc cgattcaacg gccccagggc    4860
gtccagaacg ggcttcaggc gctcccgaag gtctcgggcc gtctcttggg cttgatcggc    4920
cttcttgcgc atctcacgcg ctcctgcggc ggcctgtagg gcaggctcat accctgccg    4980 aaccgctttt gtcagccggt cggccacggc ttccggcgtc tcaacgcgct ttgagattcc    5040
cagcttttcg gccaatccct gcggtgcata ggcgcgtggc tcgaccgctt gcgggctgat    5100
ggtgacgtgg cccactggtg gccgctccag ggcctcgtag aacgcctgaa tgcgcgtgtg    5160
acgtgccttg ctgccctcga tgccccgttg cagcccctaga tcgccacag cggccgcaaa    5220 cgtggtctgg tcgcgggtca tctgcgcttt gttgccgatg aactccttgg ccgacagcct    5280
gccgtcctgc gtcagcggca ccacgaacgg ggtcatgtgc gggctggttt cgtcacggtg    5340
gatgctggcc gtcacgatgc gatccgcccc gtacttgtcc gccagccact tgtgcgcctt    5400
ctcgaagaac gccgcctgct gttcttggct ggccgactc caccattccg ggctggccgt    5460
catgacgtac tcgaccgcca acacagcgtc cttgcgccgc ttctctggca gcaactcgcg    5520
cagtcggccc atcgcttcat cggtgctgct ggccgcccag tgctcgttct ctggcgtcct    5580
```

```
gctggcgtca gcgttgggcg tctcgcgctc gcggtaggcg tgcttgagac tggccgccac   5640
gttgcccatt ttcgccagct tcttgcatcg catgatcgcg tatgccgcca tgcctgcccc   5700 tccctttttgg tgtccaaccg gctcgacggg ggcagcgcaa ggcggtgcct ccggcgggcc   5760
actcaatgct tgagtatact cactagactt tgcttcgcaa agtcgtgacc gcctacggcg   5820
gctgcggcgc cctacgggct tgctctccgg gcttcgccct gcgcggtcgc tgcgctccct   5880
tgccagcccg tggatatgtg gacgatggcc gcgagcggcc accggctggc tcgcttcgct   5940
cggcccgtgg acaaccctgc tggacaagct gatggacagg ctgcgcctgc ccacgagctt   6000
gaccacaggg attgcccacc ggctacccag ccttcgacca catacccacc ggctccaact   6060
gcgcggcctg cggccttgcc ccatcaattt ttttaatttt ctctggggaa aagcctccgg   6120
cctgcggcct gcgcgcttcg cttgccggtt ggacaccaag tggaaggcgg gtcaaggctc   6180
gcgcagcgac cgcgcagcgg cttggccttg acgcgcctgg aacgacccaa gcctatgcga   6240 gtggggggcag tcgaaggcga agcccgcccg cctgcccccc gagcctcacg gcggcgagtg   6300 cggggggttcc aaggggcag cgccaccttg gcaaggccaa aggccgcgc agtcgatcaa   6360 caagccccgg aggggccact ttttgccgga gggggagccg cgccgaaggc gtgggggaac   6420
cccgcagggg tgcccttctt tgggcaccaa agaactagat atagggcgaa atgcgaaaga   6480
cttaaaaatc aacaacttaa aaagggggg tacgcaacag ctcattgcgg cacccccgc   6540 aatagctcat tgcgtaggtt aaagaaaatc tgtaattgac tgccactttt acgcaacgca   6600
taattgttgt cgcgctgccg aaaagttgca gctgattgcg catggtgccg caaccgtgcg   6660
gcaccctacc gcatggagat aagcatggcc acgcagtcca gagaaatcgg cattcaagcc   6720
aagaacaagc ccggtcactg ggtgcaaacg gaacgcaaag cgcatgaggc gtgggccggg   6780
cttattgcga ggaaacccac ggcggcaatg ctgctgcatc acctcgtggc gcagatgggc   6840
caccagaacg ccgtggtggt cagccagaag acactttcca agctcatcgg acgttctttg   6900
cggacggtcc aatacgcagt caaggacttg gtggccgagc gctggatctc cgtcgtgaag   6960
ctcaacggcc ccggcaccgt gtcggcctac gtggtcaatg accgcgtggc gtggggccag   7020
ccccgcgacc agttgcgcct gtcggtgttc agtgccgccg tggtggttga tcacgacgac   7080
caggacgaat cgctgttggg gcatggcgac ctgcgccgca tcccgaccct gtatccgggc   7140
gagcagcaac taccgaccgg ccccggcgag gagccgccca gccagcccgg cattccgggc   7200
atggaaccag acctgccagc cttgaccgaa acggaggaat gggaacggcg cgggcagcag   7260
cgcctgccga tgcccgatga gccgtgtttt ctggacgatg cgcgagccgtt ggagccgccg   7320 acacgggtca cgctgccgcg ccggtagcac ttgggttgcg cagcaacccg taagtgcgct   7380
gttccagact atcggctgta gccgcctcgc cgccctatac cttgtctgcc tccccgcgtt   7440
gcgtcgcggt gcatggagcc gggccacctc gacctgaatg gaagccggcg gcacctcgct   7500
aacggattca ccgttttttat caggctctgg gaggcagaat aaatgatcat atcgtcaatt   7560
attacctcca cggggagagc ctgagcaaac tggcctcagg catttgagaa gcacacggtc   7620
acactgcttc cggtagtcaa taaaccggta aaccagcaat agacataagc ggctatttaa   7680
cgaccctgcc ctgaaccgac gacgggtcg aatttgcttt cgaatttctg ccattcatcc   7740
gcttattatc acttattcag gcgtagcacc aggcgtttaa gtcgaccaat aacc        7794
```

<210> SEQ ID NO 24
<211> LENGTH: 7776
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

```
tctacggggt ctgacgctca gtggaacgaa atcgatgagc tcgcacgaac ccagttgaca      60
taagcctgtt cggttcgtaa actgtaatgc aagtagcgta tgcgctcacg caactggtcc     120
agaaccttga ccgaacgcag cggtggtaac ggcgcagtgg cggttttcat ggcttgttat     180
gactgttttt ttgtacagtc tagcctcggg catccaagct agctaagcgc gttacgccgt     240
gggtcgatgt ttgatgttat ggaacagcaa cgatgttacg cagcagggta gtcgccctaa     300
aacaaagtta ggcagccgtt gtgctggtgc tttctagtag ttgttgtggg gtaggcagtc     360
agagctcgat ttgcttgtcg ccataataga ttcacaagaa ggattcgaca tgggtcaaag     420
tagcgatgaa gccaacgctc ccgttgcagg gcagtttgcg cttcccctga gtgccacctt     480
tggcttaggg gatcgcgtac gcaagaaatc tggtgccgct tggcagggtc aagtcgtcgg     540
ttggtattgc acaaaactca ctcctgaagg ctatgcggtc gagtccgaat cccacccagg     600
ctcagtgcaa atttatcctg tggctgcact tgaacgtgtg gcctaagcga tatcttagga     660
tctcccatcg gtgatgtcgg cgatataggc gccagcaacc gcacctgtgg cgccggtgat     720
gccggccacg atgcgtccgg cgtagaggat ctgctcatgt ttgacagctt atcatcgatg     780
cataatgtgc ctgtcaaatg gacgaagcag ggattctgca aaccctatgc tactccgtca     840
agccgtcaat tgtctgattc gttaccaatt atgacaactt gacggctaca tcattcactt     900
tttcttcaca accggcacgg aactcgctcg ggctggcccc ggtgcatttt ttaaataccc     960
gcgagaaata gagttgatcg tcaaaaccaa cattgcgacc gacggtggcg ataggcatcc    1020
gggtggtgct caaaagcagc ttcgcctggc tgatacgttg gtcctcgcgc agcttaaga    1080
cgctaatccc taactgctgg cggaaaagat gtgacagacg cgacggcgac aagcaaacat    1140
gctgtgcgac gctggcgata tcaaaattgc tgtctgccag gtgatcgctg atgtactgac    1200
aagcctcgcg tacccgatta tccatcggtg gatggagcga ctcgttaatc gcttccatgc    1260
gccgcagtaa caattgctca agcagattta tcgccagcag ctccgaatag cgcccttccc    1320
cttgcccggc gttaatgatt tgcccaaaca ggtcgctgaa atgcggctgg tgcgcttcat    1380
ccgggcgaaa gaaccccgta ttggcaaata ttgacggcca gttaagccat tcatgccagt    1440
aggcgcgcgg acgaaagtaa acccactggt gataccattc gcgagcctcc ggatgacgac    1500
cgtagtgatg aatctctcct ggcgggaaca gcaaaatatc acccggtcgg caaacaaatt    1560
ctcgtccctg atttttcacc acccccctgac cgcgaatggt gagattgaga atataacctt    1620
tcattcccag cggtcggtcg ataaaaaat cgagataacc gttggcctca atcggcgtta    1680
aacccgccac cagatgggca ttaaacgagt atcccggcag caggggatca ttttgcgctt    1740
cagccatact tttcatactc ccgccattca gagaagaaac caattgtcca tattgcatca    1800
gacattgccg tcactgcgtc ttttactggc tcttctcgct aaccaaaccg gtaacccgc    1860
ttattaaaag cattctgtaa caaagcggga ccaaagccat gacaaaaacg cgtaacaaaa    1920
gtgtctataa tcacggcaga aaagtccaca ttgattattt gcacggcgtc acactttgct    1980
atgccatagc atttttatcc ataagattag cggatcctac ctgacgcttt ttatcgcaac    2040
tctctactgt ttctccatac ccgtttttt gggctagcag gaggaattca ccatggatga    2100
aaattcttat tagcggtggt gcaggttata taggttctca tactttaaga caattttaa    2160
aaacagatca tgaaatttgt gttttagata atctttctaa gggttctaaa atcgcaatag    2220
```

```
aagatttgca aaaaataaga acttttaaat tttttgaaca agatttaagt gattttcaag    2280
gcgtaaaagc attgtttgag agagaaaaat ttgacgctat tgtgcatttt gcagcgagca    2340
ttgaagtttt tgaaagtatg caaaaccctt taaagtatta tatgaataac actgttaata    2400
cgacaaatct catcgaaact tgtttgcaaa ctggagtgaa taaatttata ttttcttcaa    2460
cggcagccac ttatggcgaa ccacaaactc ccgttgtgag cgaaacaagt cctttagcac    2520
ctattaatcc ttatgggcgt agtaagctta tgagcgaaga ggttttgcgt gatgcaagta    2580
tggcaaatcc tgaatttaag cattgtattt taagatattt taatgttgca ggtgcttgca    2640
tggattatac tttaggacaa cgctatccaa aagcgacttt gcttataaaa gttgcagctg    2700
aatgtgccgc agaaaaacgt aataaacttt tcatatttgg cgatgattat gatacaaaag    2760
atggcacttg cataagagat tttatccatg tggatgatat ttcaagtgcg catttatcgg    2820
ctttggatta tttaaaagag aatgaaagca atgttttttaa tgtaggttat ggacatggtt    2880
ttagcgtaaa agaagtgatt gaagcgatga aaaaagttag cggagtggat tttaaagtag    2940
aacttgcccc acgccgtgcg ggtgatccta gtgtattgat ttctgatgca agtaaaatca    3000
gaaatcttac ttcttggcag cctaaatatg atgatttagg gcttatttgt aaatctgctt    3060
ttgattggga aaaacagtgc tacccatacg atgttccaga ttacgcttaa tctagagtcg    3120
acctgcaggc atgcaagctt ggctgttttg gcggatgaga agattttc agcctgatac    3180 agattaaatc agaacgcaga agcggtctga taaaacagaa tttgcctggc ggcagtagcg    3240
cggtggtccc acctgacccc atgccgaact cagaagtgaa acgccgtagc gccgatggta    3300
gtgtggggtc tccccatgcg agagtaggga actgccaggc atcaaataaa acgaaaggct    3360
cagtcgaaag actgggcctt tcgttttatc tgttgtttgt cggtgaacgc tctcctgagt    3420
aggacaaatc cgccgggagc ggatttgaac gttgcgaagc aacggcccgg agggtggcgg    3480
gcaggacgcc cgccataaac tgccaggcat caaattaagc agaaggccat cctgacggat    3540
ggcctttttg cgtttctaca actcttcca ctcactacag cagagccatt taaacaacat    3600
cccctccccc tttccaccgc gtcagacgcc cgtagcagcc cgctacgggc ttttcatgc    3660 cctgccctag cgtccaagcc tcacggccgc gctcggcctc tctggcggcc ttctggcgct    3720
gaggtctgcc tcgtgaagaa ggtgttgctg actcatacca ggcctgaatc gccccatcat    3780
ccagccagaa agtgagggag ccacggttga tgagagcttt gttgtaggtg gaccagttgg    3840
tgattttgaa cttttgcttt gccacggaac ggtctgcgtt gtcgggaaga tgcgtgatct    3900
gatccttcaa ctcagcaaaa gttcgattta ttcaacaaag ccgccgtccc gtcaagtcag    3960
cgtaatgctc tgccagtgtt acaaccaatt aaccaattct gattagaaaa actcatcgag    4020
catcaaatga aactgcaatt tattcatatc aggattatca ataccatatt tttgaaaaag    4080
ccgtttctgt aatgaaggag aaaactcacc gaggcagttc cataggatgg caagatcctg    4140
gtatcggtct gcgattccga ctcgtccaac atcaatacaa cctattaatt tcccctcgtc    4200
aaaaataagg ttatcaagcg agaaatcacc atgagtgacg actgaatccg gtgagaatgg    4260
caaaagctaa aaaggccgta atatccagct gaacggtctg gttataggta cattgagcaa    4320
ctgactgaaa tgcctcaaaa tgttctttac gatgccattg gatatatca acggtggtat    4380 atccagtgat ttttttctcc attttagctt ccttagctcc tgaaaatctc gataactcaa    4440
aaaatacgcc cggtagtgat cttatttcat tatggtgaaa gttggaacct cttacgtgcc    4500
gatcaacgtc tcattttcgc caaaagttgg cccagggctt cccggtatca acagggacac    4560
```

```
caggatttat ttattctgcg aagtgatctt ccgtcacagg tatttattcg aagacgaaag    4620
ggcctcgtga tacgcctatt tttataggtt aatgtcatga taataatggt ttcttagacg    4680
tcaggtggca cttttcgggg aaatgtgcgc gcccgcgttc ctgctggcgc tgggcctgtt    4740
tctggcgctg gacttccgc tgttccgtca gcagcttttc gcccacggcc ttgatgatcg    4800
cggcggcctt ggcctgcata tcccgattca acggcccag ggcgtccaga acgggcttca    4860
ggcgctcccg aaggtctcgg gccgtctctt gggcttgatc ggccttcttg cgcatctcac    4920
gcgctcctgc ggcggcctgt agggcaggct catacccctg ccgaaccgct tttgtcagcc    4980
ggtcggccac ggcttccggc gtctcaacgc gctttgagat cccagctttt cggccaatc    5040
cctgcggtgc ataggcgcgt ggctcgaccg cttgcgggct gatggtgacg tggcccactg    5100
gtggccgctc cagggcctcg tagaacgcct gaatgcgcgt gtgacgtgcc ttgctgccct    5160
cgatgccccg ttgcagccct agatcggcca cagcggccgc aaacgtggtc tggtcgcggg    5220
tcatctgcgc tttgttgccg atgaactcct tggccgacag cctgccgtcc tgcgtcagcg    5280
gcaccacgaa cgcggtcatg tgcgggctgg tttcgtcacg gtggatgctg gccgtcacga    5340
tgcgatccgc cccgtacttg tccgccagcc acttgtgcgc cttctcgaag aacgccgcct    5400
gctgttcttg gctggccgac ttccaccatt ccgggctggc cgtcatgacg tactcgaccg    5460
ccaacacagc gtccttgcgc cgcttctctg gcagcaactc gcgcagtcgg cccatcgctt    5520
catcggtgct gctggccgcc cagtgctcgt tctctggcgt cctgctggcg tcagcgttgg    5580
gcgtctcgcg ctcgcggtag gcgtgcttga gactggccgc cacgttgccc attttcgcca    5640
gcttcttgca tcgcatgatc gcgtatgccg ccatgcctgc ccctcccttt tggtgtccaa    5700
ccggctcgac gggggcagcg caaggcggtg cctccggcgg gccactcaat gcttgagtat    5760
actcactaga ctttgcttcg caaagtcgtg accgcctacg gcggctgcgg cgccctacgg    5820
gcttgctctc cgggcttcgc cctgcgcggt cgctgcgctc ccttgccagc ccgtggatat    5880
gtggacgatg gccgcgagcg gccaccggct ggctcgcttc gctcggcccg tggacaaccc    5940
tgctggacaa gctgatggac aggctgcgcc tgcccacgag cttgaccaca gggattgccc    6000
accggctacc cagccttcga ccacataccc accggctcca actgcgcggc ctgcggcctt    6060
gccccatcaa ttttttttaat tttctctggg gaaaagcctc cggcctgcgg cctgcgcgct    6120
tcgcttgccg gttggacacc aagtggaagg cgggtcaagg ctcgcgcagc gaccgcgcag    6180
cggcttggcc ttgacgcgcc tggaacgacc caagcctatg cgagtggggg cagtcgaagg    6240
cgaagcccgc ccgcctgccc cccgagcctc acggcggcga gtgcgggggt tccaaggggg    6300
cagcgccacc ttgggcaagg ccgaaggccg cgcagtcgat caacaagccc cggaggggcc    6360
acttttttgcc ggaggggggag ccgcgccgaa ggcgtggggg aaccccgcag gggtgccctt    6420
ctttgggcac caaagaacta gatataggggc gaaatgcgaa agacttaaaa atcaacaact    6480
taaaaagggg gggtacgcaa cagctcattg cggcaccccc cgcaatagct cattgcgtag    6540
gttaaagaaa atctgtaatt gactgccact tttacgcaac gcataattgt tgtcgcgctg    6600
ccgaaaagtt gcagctgatt gcgcatggtg ccgcaaccgt gcggcaccct accgcatgga    6660
gataagcatg ccacgcagt ccagagaaat cggcattcaa gccaagaaca agcccggtca    6720
ctgggtgcaa acggaacgca aagcgcatga ggcgtgggcc gggcttattg cgaggaaacc    6780
cacggcggca atgctgctgc atcacctcgt ggcgcagatg ggccaccaga acgccgtggt    6840
ggtcagccag aagacacttt ccaagctcat cggacgttct ttgcggacgg tccaatacgc    6900
agtcaaggac ttggtggccg agcgctggat ctccgtcgtg aagctcaacg gccccggcac    6960
```

-continued

```
cgtgtcggcc tacgtggtca atgaccgcgt ggcgtggggc cagccccgcg accagttgcg   7020
cctgtcggtg ttcagtgccg ccgtggtggt tgatcacgac gaccaggacg aatcgctgtt   7080
ggggcatggc gacctgcgcc gcatcccgac cctgtatccg ggcgagcagc aactaccgac   7140
cggcccggc gaggagccgc ccagccagcc cggcattccg ggcatggaac cagacctgcc   7200
agccttgacc gaaacggagg aatgggaacg gcgcgggcag cagcgcctgc cgatgcccga   7260
tgagccgtgt tttctggacg atggcgagcc gttggagccg ccgacacggg tcacgctgcc   7320
gcgccggtag cacttgggtt gcgcagcaac ccgtaagtgc gctgttccag actatcggct   7380
gtagccgcct cgccgcccta taccttgtct gcctccccgc gttgcgtcgc ggtgcatgga   7440
gccgggccac ctcgacctga atggaagccg gcggcacctc gctaacggat tcaccgtttt   7500
tatcaggctc tgggaggcag aataaatgat catatcgtca attattacct ccacggggag   7560
agcctgagca aactggcctc aggcatttga gaagcacacg gtcacactgc ttccggtagt   7620
caataaaccg gtaaaccagc aatagacata agcggctatt taacgaccct gccctgaacc   7680
gacgaccggg tcgaatttgc tttcgaattt ctgccattca tccgcttatt atcacttatt   7740
caggcgtagc accaggcgtt taagtcgacc aataac                             7776
```

<210> SEQ ID NO 25
<211> LENGTH: 643
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Met Lys Lys Ile Trp Leu Ala Leu Ala Gly Leu Val Leu Ala Phe Ser
1               5                   10                  15

Ala Ser Ala Ala Glu Glu Ala Phe Asp Leu Trp Asn Glu Cys Ala Lys
            20                  25                  30

Ala Cys Val Leu Asp Leu Lys Asp Gly Val Arg Ser Ser Arg Met Ser
        35                  40                  45

Val Asp Pro Ala Ile Ala Asp Thr Asn Gly Gln Gly Val Leu His Tyr
    50                  55                  60

Ser Met Val Leu Glu Gly Gly Asn Asp Ala Leu Lys Leu Ala Ile Asp
65                  70                  75                  80

Asn Ala Leu Ser Ile Thr Ser Asp Gly Leu Thr Ile Arg Leu Glu Gly
                85                  90                  95

Gly Val Glu Pro Asn Lys Pro Val Arg Tyr Ser Tyr Thr Arg Gln Ala
            100                 105                 110

Arg Gly Ser Trp Ser Leu Asn Trp Leu Val Pro Ile Gly His Glu Lys
        115                 120                 125

Pro Ser Asn Ile Lys Val Phe Ile His Glu Leu Asn Ala Gly Asn Gln
    130                 135                 140

Leu Ser His Met Ser Pro Ile Tyr Thr Ile Glu Met Gly Asp Glu Leu
145                 150                 155                 160

Leu Ala Lys Leu Ala Arg Asp Ala Thr Phe Phe Val Arg Ala His Glu
                165                 170                 175

Ser Asn Glu Met Gln Pro Thr Leu Ala Ile Ser His Ala Gly Val Ser
            180                 185                 190

Val Val Met Ala Gln Ala Gln Pro Arg Arg Glu Lys Arg Trp Ser Glu
        195                 200                 205
```

-continued

Trp Ala Ser Gly Lys Val Leu Cys Leu Leu Asp Pro Leu Asp Gly Val
210                 215                 220

Tyr Asn Tyr Leu Ala Gln Gln Arg Cys Asn Leu Asp Asp Thr Trp Glu
225                 230                 235                 240

Gly Lys Ile Tyr Arg Val Leu Ala Gly Asn Pro Ala Lys His Asp Leu
            245                 250                 255

Asp Ile Lys Asp Asn Asn Asn Ser Thr Pro Thr Val Ile Ser His Arg
        260                 265                 270

Leu His Phe Pro Glu Gly Gly Ser Leu Ala Ala Leu Thr Ala His Gln
            275                 280                 285

Ala Cys His Leu Pro Leu Glu Ala Phe Thr Arg His Arg Gln Pro Arg
290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Gly Asp Leu Gly Glu
        340                 345                 350

Ala Ile Arg Glu Gln Pro Glu Gln Ala Arg Leu Ala Leu Thr Leu Ala
            355                 360                 365

Ala Ala Glu Ser Glu Arg Phe Val Arg Gln Gly Thr Gly Asn Asp Glu
370                 375                 380

Ala Gly Ala Ala Ser Ala Asp Val Val Ser Leu Thr Cys Pro Val Ala
385                 390                 395                 400

Lys Asp Gln Asn Arg Thr Lys Gly Glu Cys Ala Gly Pro Ala Asp Ser
                405                 410                 415

Gly Asp Ala Leu Leu Glu Arg Asn Tyr Pro Thr Gly Ala Glu Phe Leu
            420                 425                 430

Gly Asp Gly Gly Asp Val Ser Phe Ser Thr Arg Gly Thr Gln Asn Trp
        435                 440                 445

Thr Val Glu Arg Leu Leu Gln Ala His Arg Gln Leu Glu Glu Arg Gly
450                 455                 460

Tyr Val Phe Val Gly Tyr His Gly Thr Phe Leu Glu Ala Ala Gln Ser
465                 470                 475                 480

Ile Val Phe Gly Gly Val Arg Ala Arg Ser Gln Asp Leu Asp Ala Ile
                485                 490                 495

Trp Arg Gly Phe Tyr Ile Ala Gly Asp Pro Ala Leu Ala Tyr Gly Tyr
            500                 505                 510

Ala Gln Asp Gln Glu Pro Asp Ala Arg Gly Arg Ile Arg Asn Gly Ala
        515                 520                 525

Leu Leu Arg Val Tyr Val Pro Arg Trp Ser Leu Pro Gly Phe Tyr Arg
530                 535                 540

Thr Gly Leu Thr Leu Ala Ala Pro Glu Ala Ala Gly Glu Val Glu Arg
545                 550                 555                 560

Leu Ile Gly His Pro Leu Pro Leu Arg Leu Asp Ala Ile Thr Gly Pro
                565                 570                 575

Glu Glu Glu Gly Gly Arg Val Thr Ile Leu Gly Trp Pro Leu Ala Glu
            580                 585                 590

Arg Thr Val Val Ile Pro Ser Ala Ile Pro Thr Asp Pro Arg Asn Val
        595                 600                 605

Gly Gly Asp Leu Asp Pro Ser Ser Ile Pro Asp Lys Glu Gln Ala Ile
610                 615                 620

Ser Ala Leu Pro Asp Tyr Ala Ser Gln Pro Gly Lys Pro Pro Arg Glu

```
                625                 630                 635                 640

Asp Leu Lys

<210> SEQ ID NO 26
<211> LENGTH: 722
<212> TYPE: PRT
<213> ORGANISM: Campylobacter jejuni

<400> SEQUENCE: 26

Met Leu Lys Lys Glu Tyr Leu Lys Asn Pro Tyr Leu Val Leu Phe Ala
1               5                   10                  15

Met Ile Ile Leu Ala Tyr Val Phe Ser Val Phe Cys Arg Phe Tyr Trp
            20                  25                  30

Val Trp Trp Ala Ser Glu Phe Asn Glu Tyr Phe Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Ala Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Thr Ile Leu Leu Ala Asn Glu Tyr Lys Arg Pro Leu Met
        115                 120                 125

Gly Phe Val Ala Ala Leu Leu Ala Ser Ile Ala Asn Ser Tyr Tyr Asn
130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
        195                 200                 205

Leu Ile Tyr Thr Leu Ile Phe His Arg Lys Glu Lys Ile Phe Tyr Ile
210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
        275                 280                 285

Lys Phe Tyr Ile Phe Arg Ser Asp Glu Ser Ala Asn Leu Thr Gln Gly
290                 295                 300

Phe Met Tyr Phe Asn Val Asn Gln Thr Ile Gln Glu Val Glu Asn Val
305                 310                 315                 320

Asp Leu Ser Glu Phe Met Arg Arg Ile Ser Gly Ser Glu Ile Val Phe
                325                 330                 335

Leu Phe Ser Leu Phe Gly Phe Val Trp Leu Leu Arg Lys His Lys Ser
            340                 345                 350

Met Ile Met Ala Leu Pro Ile Leu Val Leu Gly Phe Leu Ala Leu Lys
```

```
                355                 360                 365
Gly Gly Leu Arg Phe Thr Ile Tyr Ser Val Pro Val Met Ala Leu Gly
        370                 375                 380
Phe Gly Phe Leu Leu Ser Glu Phe Lys Ala Ile Met Val Lys Lys Tyr
385                 390                 395                 400
Ser Gln Leu Thr Ser Asn Val Cys Ile Val Phe Ala Thr Ile Leu Thr
                405                 410                 415
Leu Ala Pro Val Phe Ile His Ile Tyr Asn Tyr Lys Ala Pro Thr Val
            420                 425                 430
Phe Ser Gln Asn Glu Ala Ser Leu Leu Asn Gln Leu Lys Asn Ile Ala
        435                 440                 445
Asn Arg Glu Asp Tyr Val Val Thr Trp Ala Ala Tyr Gly Tyr Pro Val
    450                 455                 460
Arg Tyr Tyr Ser Asp Val Lys Thr Leu Val Asp Gly Gly Lys His Leu
465                 470                 475                 480
Gly Lys Asp Asn Phe Phe Pro Ser Phe Ala Leu Ser Lys Asp Glu Gln
                485                 490                 495
Ala Ala Ala Asn Met Ala Arg Leu Ser Val Glu Tyr Thr Glu Lys Ser
            500                 505                 510
Phe Tyr Ala Pro Gln Asn Asp Ile Leu Lys Thr Asp Ile Leu Gln Ala
        515                 520                 525
Met Met Lys Asp Tyr Asn Gln Ser Asn Val Asp Leu Phe Leu Ala Ser
    530                 535                 540
Leu Ser Lys Pro Asp Phe Lys Ile Asp Thr Pro Lys Thr Arg Asp Ile
545                 550                 555                 560
Tyr Leu Tyr Met Pro Ala Arg Met Ser Leu Ile Phe Ser Thr Val Ala
                565                 570                 575
Ser Phe Ser Phe Ile Asn Leu Asp Thr Gly Val Leu Asp Lys Pro Phe
            580                 585                 590
Thr Phe Ser Thr Ala Tyr Pro Leu Asp Val Lys Asn Gly Glu Ile Tyr
        595                 600                 605
Leu Ser Asn Gly Val Val Leu Ser Asp Asp Phe Arg Ser Phe Lys Ile
    610                 615                 620
Gly Asp Asn Val Val Ser Val Asn Ser Ile Val Glu Ile Asn Ser Ile
625                 630                 635                 640
Lys Gln Gly Glu Tyr Lys Ile Thr Pro Ile Asp Asp Lys Ala Gln Phe
                645                 650                 655
Tyr Ile Phe Tyr Leu Lys Asp Ser Ala Ile Pro Tyr Ala Gln Phe Ile
            660                 665                 670
Leu Met Asp Lys Thr Met Phe Asn Ser Ala Tyr Val Gln Met Phe Phe
        675                 680                 685
Leu Gly Asn Tyr Asp Lys Leu Phe Asp Leu Val Ile Asn Ser Arg
    690                 695                 700
Asp Ala Lys Val Phe Lys Leu Lys Ile Tyr Pro Tyr Asp Val Pro Asp
705                 710                 715                 720
Tyr Ala

<210> SEQ ID NO 27
<211> LENGTH: 8171
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 27

```
gcggccgcaa ggggttcgcg tcagcgggtg ttggcgggtg tcggggctgg cttaactatg      60
cggcatcaga gcagattgta ctgagagtgc accatatgcg gtgtgaaata ccgcacagat     120
gcgtaaggag aaaataccgc atcaggcgcc attcgccatt cagctgcgca actgttggga     180
agggcgatcg gtgcgggcct cttcgctatt acgccagctg gcgaaagggg gatgtgctgc     240
aaggcgatta agttgggtaa cgccagggtt ttcccagtca cgacgttgta aaacgacggc     300
cagtgaattg taatacgact cactataggg cgaattcgag ctcggtaccc ggggatccca     360
cgtggcgcgc cactagtgct agcgacgtcg tgggatcctc tagagtcgac ctgcaggcat     420
gcaagcttga gtattctata gtctcaccta aatagcttgg cgtaatcatg gtcatagctg     480
tttcctgtgt gaaattgtta tccgctcaca attccacaca acatacgagc cggaagcata     540
aagtgtaaag cctggggtgc ctaatgagtg agctaactca cattaattgc gttgcgctca     600
ctgcccgctt tccagtcggg aaacctgtcg tgccagctgc attaatgaat cggccaacgc     660
gaacccttg cggccgcccg ggcgtcgac caattctcat gtttgacagc ttatcatcga     720
atttctgcca ttcatccgct tattatcact tattcaggcg tagcaaccag gcgtttaagg     780
gcaccaataa ctgccttaaa aaaattacgc cccgccctgc cactcatcgc agtactgttg     840
taattcatta agcattctgc cgacatggaa gccatcacaa acggcatgat gaacctgaat     900
cgccagcggc atcagcacct gtcgccttg cgtataatt tgcccatgg tgaaaacggg     960
ggcgaagaag ttgtccatat tggccacgtt taaatcaaaa ctggtgaaac tcacccaggg    1020
attggctgag acgaaaaaca tattctcaat aaacccttta gggaaatagg ccaggttttc    1080
accgtaacac gccacatctt gcgaatatat gtgtagaaac tgccggaaat cgtcgtggta    1140
ttcactccag agcgatgaaa acgtttcagt ttgctcatgg aaaacggtgt aacaagggtg    1200
aacactatcc catatcacca gctcaccgtc tttcattgcc atacgaaatt ccggatgagc    1260
attcatcagg cgggcaagaa tgtgaataaa ggccggataa aacttgtgct tattttttctt    1320
tacggtcttt aaaaaggccg taatatccag ctgaacggtc tggttatagg tacattgagc    1380
aactgactga aatgcctcaa aatgttcttt acgatgccat gggatatat caacggtggt    1440
atatccagtg atttttttct ccatttagc ttccttagct cctgaaaatc tcgataactc    1500
aaaaaatacg cccggtagtg atcttatttc attatggtga agttggaac ctcttacgtg    1560
ccgatcaacg tctcatttc gccaaaagtt ggcccagggc ttcccggtat caacagggac    1620
accaggattt atttattctg cgaagtgatc ttccgtcaca ggtatttatt cgcgataagc    1680
tcatggagcg gcgtaaccgt cgcacaggaa ggacagagaa agcgcggatc tgggaagtga    1740
cggacagaac ggtcaggacc tggattgggg aggcggttgc cgccgctgct gctgacggtg    1800
tgacgttctc tgttccggtc acaccacata cgttccgcca ttcctatgcg atgcacatgc    1860
tgtatgccgg tataccgctg aaagttctgc aaagcctgat gggacataag tccatcagtt    1920
caacggaagt ctacacgaag gttttgcgc tggatgtggc tgcccggcac cggggtgcagt    1980
ttgcgatgcc ggagtctgat gcggttgcga tgctgaaaca attatcctga gaataaatgc    2040
cttggccttt atatggaaat gtggaactga gtggatatgc tgttttttgtc tgttaaacag    2100
agaagctggc tgttatccac tgagaagcga acgaaacagt cgggaaaatc tcccattatc    2160
gtagagatcc gcattattaa tctcaggagc ctgtgtagcg tttataggaa gtagtgttct    2220
gtcatgatgc ctgcaagcgg taacgaaaac gatttgaata tgccttcagg aacaatagaa    2280
atcttcgtgc ggtgttacgt tgaagtggag cggattatgt cagcaatgga cagaacaacc    2340
```

```
taatgaacac agaaccatga tgtggtctgt ccttttacag ccagtagtgc tcgccgcagt    2400
cgagcgacag ggcgaagccc tcggctggtt gccctcgccg ctgggctggc ggccgtctat    2460
ggccctgcaa acgcgccaga aacgccgtcg aagccgtgtg cgagacaccg cggccggccg    2520
ccggcgttgt ggatacctcg cggaaaactt ggccctcact gacagatgag gggcggacgt    2580
tgacacttga ggggccgact cacccggcgc ggcgttgaca gatgaggggc aggctcgatt    2640
tcggccggcg acgtggagct ggccagcctc gcaaatcggc gaaaacgcct gattttacgc    2700
gagtttccca cagatgatgt ggacaagcct ggggataagt gccctgcggt attgacactt    2760
gaggggcgcg actactgaca gatgaggggc gcgatccttg acacttgagg gcagagtgc    2820
tgacagatga ggggcgcacc tattgacatt tgaggggctg tccacaggca gaaaatccag    2880
catttgcaag ggtttccgcc cgttttcgg ccaccgctaa cctgtctttt aacctgcttt    2940
taaaccaata tttataaacc ttgttttaa ccagggctgc gccctgtgcg cgtgaccgcg    3000
cacgccgaag gggggtgccc cccttctcg aaccctcccg gtcgagtgag cgaggaagca    3060
ccagggaaca gcacttatat attctgctta cacacgatgc ctgaaaaaac ttcccttggg    3120
gttatccact tatccacggg gatatttta taattatttt ttttatagtt tttagatctt    3180
cttttttaga gcgccttgta ggcctttatc catgctggtt ctagagaagg tgttgtgaca    3240
aattgcccct tcagtgtgac aaatcaccct caaatgacag tcctgtctgt gacaaattgc    3300
ccttaaccct gtgacaaatt gccctcagaa gaagctgttt tttcacaaag ttatccctgc    3360
ttattgactc tttttatt agtgtgacaa tctaaaaact tgtcacactt cacatggatc    3420
tgtcatggcg gaaacagcgg ttatcaatca caagaaacgt aaaaatagcc cgcgaatcgt    3480
ccagtcaaac gacctcactg aggcggcata tagtctctcc cgggatcaaa aacgtatgct    3540
gtatctgttc gttgaccaga tcagaaaatc tgatggcacc ctacaggaac atgacggtat    3600
ctgcagatc catgttgcta aatatgctga aatattcgga ttgacctctg cggaagccag    3660
taaggatata cggcaggcat tgaagagttt cgcggggaag gaagtggttt tttatcgccc    3720
tgaagaggat gccggcgatg aaaaaggcta tgaatctttt ccttggttta tcaaacgtgc    3780
gcacagtcca tccagagggc tttacagtgt acatatcaac ccatatctca ttcccttctt    3840
tatcgggtta cagaaccggt ttacgcagtt tcggcttagt gaaacaaaag aaatcaccaa    3900
tccgtatgcc atgcgtttat acgaatccct gtgtcagtat cgtaagccgg atggctcagg    3960
catcgtctct ctgaaaatcg actggatcat agagcgttac cagctgcctc aaagttacca    4020
gcgtatgcct gacttccgcc gccgcttcct gcaggtctgt gttaatgaga tcaacagcag    4080
aactccaatg cgcctctcat acattgagaa aaagaaaggc cgccagacga ctcatatcgt    4140
attttccttc cgcgatatca cttccatgac gacaggatag tctgagggtt atctgtcaca    4200
gatttgaggg tggttcgtca catttgttct gacctactga gggtaatttg tcacagtttt    4260
gctgtttcct tcagcctgca tggattttct catactttt gaactgtaat ttttaaggaa    4320
gccaaatttg agggcagttt gtcacagttg atttccttct ctttcccttc gtcatgtgac    4380
ctgatatcgg gggttagttc gtcatcattg atgagggttg attatcacag tttattactc    4440
tgaattggct atccgcgtgt gtacctctac ctggagtttt tcccacggtg atatttctt    4500
cttgcgctga gcgtaagagc tatctgacag aacagttctt ctttgcttcc tcgccagttc    4560
gctcgctatg ctcggttaca cggctgcggc gagcgctagt gataataagt gactgaggta    4620
tgtgctcttc ttatctcctt ttgtagtgtt gctcttattt taaacaactt tgcggttttt    4680
```

```
tgatgacttt gcgattttgt tgttgctttg cagtaaattg caagatttaa taaaaaaacg    4740
caaagcaatg attaaaggat gttcagaatg aaactcatgg aaacacttaa ccagtgcata    4800
aacgctggtc atgaaatgac gaaggctatc gccattgcac agtttaatga tgacagcccg    4860
gaagcgagga aaataacccg gcgctggaga ataggtgaag cagcggattt agttggggtt    4920
tcttctcagg ctatcagaga tgccgagaaa gcagggcgac taccgcaccc ggatatggaa    4980
attcgaggac gggttgagca acgtgttggt tatacaattg aacaaattaa tcatatgcgt    5040
gatgtgtttg gtacgcgatt gcgacgtgct gaagacgtat ttccaccggt gatcggggtt    5100
gctgcccata aaggtggcgt ttacaaaacc tcagtttctg ttcatcttgc tcaggatctg    5160
gctctgaagg ggctacgtgt tttgctcgtg gaaggtaacg accccagggg aacagcctca    5220
atgtatcacg gatgggtacc agatcttcat attcatgcag aagacactct cctgcctttc    5280
tatcttgggg aaaaggacga tgtcacttat gcaataaagc ccacttgctg gccggggctt    5340
gacattattc cttcctgtct ggctctgcac cgtattgaaa ctgagttaat gggcaaattt    5400
gatgaaggta aactgcccac cgatccacac ctgatgctcc gactggccat tgaaactgtt    5460
gctcatgact atgatgtcat agttattgac agcgcgccta acctgggtat cggcacgatt    5520
aatgtcgtat gtgctgctga tgtgctgatt gttcccacgc ctgctgagtt gtttgactac    5580
acctccgcac tgcagttttt cgatatgctt cgtgatctgc tcaagaacgt tgatcttaaa    5640
gggttcgagc ctgatgtacg tattttgctt accaaataca gcaatagtaa tggctctcag    5700
tccccgtgga tggaggagca aattcgggat gcctggggaa gcatggttct aaaaaatgtt    5760
gtacgtgaaa cggatgaagt tggtaaaggt cagatccgga tgagaactgt ttttgaacag    5820
gccattgatc aacgctcttc aactggtgcc tggagaaatg ctctttctat ttgggaacct    5880
gtctgcaatg aaattttcga tcgtctgatt aaaccacgct gggagattag ataatgaagc    5940
gtgcgcctgt tattccaaaa catacgctca atactcaacc ggttgaagat acttcgttat    6000
cgacaccagc tgccccgatg gtggattcgt taattgcgcg cgtaggagta atggctcgcg    6060
gtaatgccat tactttgcct gtatgtggtc gggatgtgaa gtttactctt gaagtgctcc    6120
ggggtgatag tgttgagaag acctctcggg tatggtcagg taatgaacgt gaccaggagc    6180
tgcttactga ggacgcactg gatgatctca tcccttcttt tctactgact ggtcaacaga    6240
caccggcgtt cggtcgaaga gtatctgtgt catagaaaat tgccgatggg agtcgccgtc    6300
gtaaagctgc tgcacttacc gaaagtgatt atcgtgttct ggttggcgag ctggatgatg    6360
agcagatggc tgcattatcc agattgggta acgattatcg cccaacaagt gcttatgaac    6420
gtggtcagcg ttatgcaagc cgattgcaga atgaatttgc tggaaatatt tctgcgctgg    6480
ctgatgcgga aaatatttca cgtaagatta ttacccgctg tatcaacacc gccaaattgc    6540
ctaaatcagt tgttgctctt ttttctcacc ccggtgaact atctgcccgg tcaggtgatg    6600
cacttcaaaa agcctttaca gataaagagg aattacttaa gcagcaggca tctaaccttc    6660
atgagcagaa aaaagctggg gtgatatttg aagctgaaga agttatcact cttttaactt    6720
ctgtgcttaa aacgtcatct gcatcaagaa ctagtttaag ctcacgacat cagtttgctc    6780
ctggagcgac agtattgtat aagggcgata aaatggtgct taacctggac aggtctcgtg    6840
ttccaactga gtgtatagag aaaattgagg ccattcttaa ggaacttgaa aagccagcac    6900
cctgatgcga ccacgtttta gtctacgttt atctgtcttt acttaatgtc ctttgttaca    6960
ggccagaaag cataactggc ctgaatattc tctctgggcc cactgttcca cttgtatcgt    7020
cggtctgata atcagactgg gaccacggtc ccactcgtat cgtcggtctg attattagtc    7080
```

```
tgggaccacg gtcccactcg tatcgtcggt ctgattatta gtctgggacc acggtcccac    7140
tcgtatcgtc ggtctgataa tcagactggg accacggtcc cactcgtatc gtcggtctga    7200
ttattagtct gggaccatgg tcccactcgt atcgtcggtc tgattattag tctgggacca    7260
cggtcccact cgtatcgtcg gtctgattat tagtctggaa ccacggtccc actcgtatcg    7320
tcggtctgat tattagtctg gaccacggt cccactcgta tcgtcggtct gattattagt    7380
ctgggaccac gatcccactc gtgttgtcgg tctgattatc ggtctgggac cacggtccca    7440
cttgtattgt cgatcagact atcagcgtga gactacgatt ccatcaatgc ctgtcaaggg    7500
caagtattga catgtcgtcg taacctgtag aacggagtaa cctcggtgtg cggttgtatg    7560
cctgctgtgg attgctgctg tgtcctgctt atccacaaca ttttgcgcac ggttatgtgg    7620
acaaaatacc tggttaccca ggccgtgccg gcacgttaac cgggctgcat ccgatgcaag    7680
tgtgtcgctg tcgacgagct cgcgagctcg acatgaggt tgccccgtat tcagtgtcgc    7740
tgatttgtat tgtctgaagt tgttttacg ttaagttgat gcagatcaat taatacgata    7800
cctgcgtcat aattgattat ttgacgtggt ttgatggcct ccacgcacgt tgtgatatgt    7860
agatgataat cattatcact ttacgggtcc tttccggtga tccgacaggt tacggggcgg    7920
cgacctcgcg ggttttcgct atttatgaaa attttccggt ttaaggcgtt ccgttcttc    7980 ttcgtcataa cttaatgttt ttatttaaaa taccctctga aaagaaagga aacgacaggt    8040
gctgaaagcg agcttttgg cctctgtcgt ttcctttctc tgttttgtc cgtggaatga    8100 acaatggaag tccgagctca tcgctaataa cttcgtatag catacattat acgaagttat    8160
attcgatcca c                                                          8171

<210> SEQ ID NO 28
<211> LENGTH: 20982
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
ctagcggcaa aacgtatgcc gggtgacctc tctgaatact ccgtcatcca gaccaaagaa      60
ccgctggatc gcgaaggtaa agtcagccgc attgttgaat ttatcgaaaa accggatcag     120
ccgcagacgc tggactcaga catcatggcc gttggtcgct atgtgctttc tgccgatatt     180
tggccggaac ttgaacgtac tcagcctggt gcatggggac gtattcagct gactgatgcc     240
attgccgagc tggcgaaaaa acagtccgtt gatgcaatgc tgatgaccgg cgacagctac     300
gactgcggta aaaaaatggg ctatatgcag gcgtttgtga agtatgggct gcgcaacctg     360
aaagaagggg cgaagttccg taaaggtatt gagaagctgt taagcgaata atgaaaatct     420
gaccggatgt aacggttgat aagaaaatta taacggcagt gaagattcgt ggtgaaagta     480
atttgttgcg aatattcctg ccgttgtttt atataaacaa tcagaataac aacgagttag     540
caataggatt ttagtcaaag ttttccagga ttttccttgt ttccagagcg gattggtaag     600
acaattagct tttgaattt tcgggtttag cgcgagtggg taacgctcgt cacatcgtag     660
gcatgcatgc agtgctctgg tagctgtaaa gccaggggcg gtagcgtgca ttaatacttc     720
tattaatcaa actgagagcc gcttatttca cagcatgctc tgaagcaata tggaataaat     780
taggtgaaaa tacttgttac tggtggcgca ggatttattg gttttgctgt agttcgtcac     840
attataaata atacgcagga tagtgttgtt aatgtcgata aattaacgta cgccggaaac     900
```

```
ctggaatcac ttgctgatgt ttctgattct gaacgctatg tttttgaaca tgcggatatt      960
tgcgatgcag ctgcaatggc acggattttt gctcagcatc agccagatgc agtgatgcac     1020
ctggctgctg aaagccatgt tgaccgttca attacaggtc ctgcggcatt tattgaaacc     1080
aatattgttg gtacatatgt cctttggaa gccgctcgca attattggtc tgctcttgat      1140
agcgacaaga aaactagatt ccgttttcat catatttcta ctgacgaagt ctatggtgat     1200
ttgcctcatc ctgacgaggt aaataataca gaagaattac ccttatttac agagacaaca     1260
gcttacgcgc caagcagccc ttattccgct tcaaaagcat ccagcgatca tttagtccgc     1320
gcgtggaaac gtacctatgg tttaccaacc attgtgacta attgctctaa taattatggt     1380
ccttatcatt tcccggaaaa attgattcca ttggttattc tgaatgctct ggaaggtaag     1440
gcattaccta tttatggcaa aggggatcaa attcgtgact ggctgtatgt tgaagatcat     1500
gcgcgtgcgt tatataccgt cgtaaccgaa ggtaaagcgg gtgaaactta acattggt      1560 ggacacaacg aaaagaaaaa catcgatgta gtgctcacta tttgtgattt gctggatgag     1620
attgtaccga agagaaatc ttaccgcgag caaattactt atgttgccga tcgcccggga      1680
cacgatcgcc gttatgcgat tgatgcagag aagattagcc gcgaattggg ctggaaaccg     1740
caggaaacgt ttgagagcgg gattcggaag acattggaat ggtacctgtc caatacaaaa     1800
tgggttgata atgtgaaaag tggtgcttat caatcgtgga ttgaacagaa ctatgagggc     1860
cgccagtaat gaatatcctc cttttcggca aaacagggca ggtaggttgg gaactacagc     1920
gtgctctggc acctttgggt aatttgattg ctcttgatgt tcactccact gattattgtg     1980
gtgattttag taatcctgaa ggtgtagctg aaacagtcaa aagaattcga cctgatgtta     2040
ttgttaatgc tgcggctcac accgcagtag ataaggctga gtcagaaccc gaatttgcac     2100
aattactcaa tgcgactagt gttgaatcaa ttgcaaaaga ggctaatgaa gttggggctt     2160
gggtaattca ttactcaact gactacgtat tccctggaaa tggcgacacg ccatggctgg     2220
agacggatgc aaccgcaccg ctaaatgttt acggtgaaac caagttagcc ggagaaaaag     2280
cgttacagga acattgcgcg aagcatctta ttttccgtac cagctgggta tacgcagcta     2340
aaggaaataa cttcgccaaa acgatgttgc gtctggcaaa agagcgcgaa gaactggctg     2400
tgataaatga tcaatttggt gcgccaacag gtgctgagct gctggctgat tgtacggcac     2460
atgctattcg tgtggcactg aataaaccgg aagtcgcagg tttgtaccat ctggtagcca     2520
gtggtaccac aacctggcac gattatgctg cgctggtttt tgaagaggcg cgcaaagcag     2580
gtattcccct tgcactcaac aagctcaacg cagtaccaac aacagcctat cctacaccag     2640
ctcgtcgtcc acataactct cgccttaata cagaaaaatt tcagcagaac tttgcgcttg     2700
tcttgcctga ctgcaggtt ggtgtgaaac gaatgctcaa cgaattaatt acgactacag      2760
caatttaata gttttttgcat cttgttcgtg atggtggagc aagatgaatt aaaaggaatg     2820
atgaaatgaa aacgcgtaaa ggtattattt tagcgggtgg ttctggtaca cgtctttatc     2880
ctgtgactat ggctgtcagt aaacagctat tacctattta tgataagccg atgatctatt     2940
acccgctctc tacactgatg ttggcgggta ttcgcgatat tctgattatt agtacgccac     3000
aggatactcc tcgttttcaa caactgctag gtgacgtag ccagtggggg ctaaatcttc      3060
agtacaaagt gcaaccgact ccagatgggc ttgcgcaggc gtttattatc ggtgaagagt     3120
ttatcggtgg tgatgattgt gctttggttc ttggtgataa tatcttctac ggtcatgatc     3180
tgccgaagtt aatggatgtc gctgttaaca agaaagtgg tgcaacggta tttgcctatc      3240
```

-continued

```
acgttaatga tcctgaacgc tacggcgtcg ttgagtttga taaaaacggt acggcaataa    3300
gcctggaaga aaaaccgcta caaccaaaaa gtaattatgc ggtaaccggg ctttatttct    3360
atgataacga cgttgtcgaa atggcgaaaa accttaagcc ttctgcccgt ggtgaactgg    3420
aaattaccga tattaaccgt atttatatgg aacaggggcg tttatccgtt gccatgatgg    3480
ggcgtggtta tgcatggctg atacgggga cacatcagag tcttattgaa gcaagcaact    3540
tcattgccac cattgaagag cgccaggac taaaggtttc ctgcccagaa gaaattgctt    3600
accgtaaagg gtttattgat gctgaacagg tgaaagcatt agcggagccg ctgaaaaaaa    3660
atgcttatgg acagtatctg ctgaaaatga ttaaaggtta ttaataaaat gaacgtaatt    3720
aaaacagaaa ttcctgatgt gttaattttc gagccgaaag tttttggtga tgagcgtggt    3780
ttctttatgg aaagctttaa tcagaaagtt ttcgaagaag ctgtaggacg taaggttgaa    3840
tttgttcagg ataaccattc gaagtctagt aaaggtgttt tacgcgggct gcattatcag    3900
ttagaacctt atgcgcaagg gaaactggta cgttgcgttg ttggtgaggt ttttgatgta    3960
gctgttgata ttcgtaaatc gtcgcctacc tttggtaaat gggttggggt gaatttatct    4020
gctgagaata gcggcaatt gtggatccct gagggatttg cacatggttt tttggtgctg    4080
agcgagactg cggaattttt atataaaacg acgaactatt atcatcctga tagtgatagaa   4140 gggattgtat ggaatgatcc tattctgagc ataaaatggc cgacgataga acataataat    4200
tatattttat cgattaaaga tgcaaggggct aaagaattgc ataacatgaa ggaattattt    4260
ttgtgagtat tgtaaagaat actttatgga atataagtgg gtatattata ccatcattaa    4320
tagcaattcc tgcgttaggt atactgtcta gaattctagg gaccgagcaa tttggccttt    4380
ttacgttagc tattgcctta gttggatatg caagtatttt tgatgctgga ttgaccagag    4440
ctgttataag agaagtatca atatataaaa atgttcataa gaattaaga gcgatcattt    4500 caacttcaac ggtaattcta actatattgg gcttgattgg cggtagtgta ctattttga    4560 gtagcaatgt aattgttaaa ttattaaaca ttaacgcgaa tcatgttgta gaatctgtca    4620
aagcaatata tattatttca gctaccatac ccttatactt gttaaaccaa gtctggttgg    4680 ggattttga ggggatggaa aagttcagaa aagtaaattt aataaaatca attaacaact    4740
cttttgtggc tggattacca gtgatttct gtttttttca tggaggatta ctaagtgcta    4800
tatatggttt agttatggca agagtcttat cacttatagt gacctttata tttagtcgaa    4860
aactaataat atcatctggg ctgtctgtaa aaattgtaac agttaaaaga ttaatcggct    4920
ttggaagctg gataacagtt agcaatatta ttagccctat tatgacatat atggatcgtt    4980
ttattctttc acacattgtg ggggctgata agtttctttt ttatactgct ccgtctgaag    5040
gtatacaacg cttaacgata ttaccaagtg cgttgtccag agctattttt ccaagattaa    5100
gttcagaatt gcaatcggta aagcaaacta aaatattatc atattttata atggttattg    5160
gtatacttcc aattgtaatg ttgataatta tttatcaga ttttataatg tccgcttgga    5220
tgggacctac atatcatggg acgccaggta tagtattaaa aattcttgca ataggtttct    5280
tttttaattg cattgcacaa atcccatttg tttcagttca ggctagtgga agatcaaaaa    5340
ttacagctat tattcatttg ctcgaagtta tcccatattt atgcatatta tatatttta    5400 tttatcattg gggaattgtt ggagccgcaa tagcatggtc tgtaagaaca tcgttagatt    5460
ttttgatatt attattaatt gatacgaaat attaatagcg aattgatttt agggattact    5520
tcctcaagcc catctaatta gagtgcaaac atgacttctg attttataa ctcaaaagac    5580 aaaagtttaa gtgttctttt gtttttttggg tttatatttt tccttacacg tagcttttcca    5640
```

```
tttattcaat atagttggat tatggagggg tttttatgtc tttgtatcat gtcatttaca    5700
aagaaaattg caaacggaat atatcactat cctgttattt taatatttct attagctctt    5760
tttataaatt ttatttattc ctatatcaag ggtaacgata tagcgataat aattaggttt    5820
tatattatca tattatttat attatgtgct tatttctgct cttatggaac catctcgatt    5880
gttaaaatat ttttatattt aatggtatta caggcggtta ttatatccat cattagtatt    5940
tatatgacaa aaacatatgg tattggtgat tattcagcac taagacatta tttttttggag   6000 aatgattatg gtgatgttta tacatatgga agtggtttct atagagttca aattaaagga    6060
aatgctctca ttccatttgc ctttatgttg catatagtca taaaagatta tttctattat    6120
cgattcaaaa atacaataac cgttattctg gctataggta ctatagtggc tggtaatttt    6180
gcatattttg tttcgatatg cttgtttttt atgtatatta tactatgttc taaatctaac    6240
tcacgatacg ctaaattaag gaaaattatt tttggggttt ttcttactgt gattctccct    6300 tttttttatta catattcaat tgagttgata atcatgaaat caaatggagc tgattcttct    6360
ttaggagtta gatgggatca gtttactgta ttaattaatg atcttacaga gtctgtatca    6420
aattttgtta taggttctgg tttgggtaat gtcatcaaaa ttcaaactcc tatccgtgat    6480
tatagtgcat atatatatta tgaattgcag tcagtttatt ttttaaatca acttggcgtt    6540
attttattta ctttgttttt attaattaat ctccttctca cgattaaaat cataaaatac    6600
agtgagttgt gtgtgctata ttttctatat gtttcttatg caattactaa tccttatatt    6660
ttagactcta accatgttgc tgtaataatt gtattagtga cattaagtaa tgttctaaaa    6720
aagatgaaag ctaaatgaag gttttaaggt gaagatggac actgtatatg ccgttttggt    6780
tgcttacaac ccagaacata atgatttaaa aaatgcggtt gaattattgt tgagacaagt    6840
tactaaagtt gtcgtttgca ataactctac aaatggttat aaatatgctg aaaattcttc    6900
aggcgatgta aaaatattca atttcaatga taatttaggc atagcagaag cccaaagtat    6960
aggaatgaaa tgggcttttg aaaatggcgc tgattttata ttgcaaatgg atcaggatag    7020
tattcctgat cctaagatgg tagagcagtt acttacttgt tacaaaaaat tgcttaaaca    7080
aaatgtcaat gttggtttag ttggttcaca agattttgat aaagtaactg gtgaattaaa    7140
taaagcaagg gtaaaaaaag ggaaaccact tacagaagtt tattatgagg tagatagtac    7200
attaagttct ggcagtctaa taccaaaaaa tagttggttg attgttggag gaatgaaaga    7260
tgagcttttt atcgatgcgg tagaccatga atattgttgg agattaagag ctgctgggtt    7320
taaagtaatt aggaataaaa atgcgttact tgcacataga cttggagatg ggcgatttaa    7380
gatcttaaat attctttctg tcggtttgcc aagcccattt cgtcattatt atgctactcg    7440
aaatatcttt ctttattaa ataaaaatta tgtacccatc tactgaaaaa tttctagtct     7500
ggttaaatta attggaaagg ttttttttata tcctatttc cttccaaatg gtaataaaag    7560
gttatatttt tttttaaaag gcattaatga cggtttaatg ggtcgaagtg gtaaaatgaa    7620
atgaatcata gattagaaaa attctcagtt ttaattagca tttataaaaa tgatctaccg    7680
caattttttg aggtggctct acgctctatt tttcacgatc aaacacttaa gccagatcaa    7740
atagtaattg ttgcagatgg agaactccat caaacacaca tcgatattat aaattcattc    7800
attgatgatg ttggcaataa aatagtaaca tttgtacctt tacctagaaa tgttggattg    7860
gctaatgcct taaatgaagg attaaaggct tgtaggaatg agttagtggc aagaatggat    7920
gctgatgata tttctttgcc tcatcggttt gagaaacaaa tttcttttat gattaataat    7980
```

```
tcagaaatag atgtatgtgg cagttttatt gatgaaattg aaactgttac tgaggagttt    8040
atttcaacac gcaaagtgcc tctcgaacat agagaaatag ttaaattcgc gaggaaacga    8100
agcgcagtta gccatccttc tgtaatttt  agaaagaata cagtattagc tgttggtggt    8160
tatcctccat tcagaaaatc tcaagatttt gcattgtgga gcctattaat tgtacataat    8220
gcaagatttg caaatcttcc agatatttta ttaaaaatgc gaactggtcg taatcttatg    8280
gctcgacgtg gattgtcata tttattgtac gagtataaag tattgtatta tcaatataaa    8340
attggtttta ttcgaaaaaa tgaattaata agtaatgcta tgttgagaac attttttcgt    8400
ataatgccat ctaaattaaa ggagctgatg tattcaatcg ttaggaatcg ataataataa    8460
ttttctgatt aagtgttatg gatttatttt tattaggcat attctataat taagcataac    8520
ccgcatacca cccagcggta tcctgacagg agtaaacaat gtcaaagcaa cagatcggcg    8580
tcgtcggtat ggcagtgatg gggcgcaacc ttgcgctcaa tatcgaaagc cgtggttata    8640
ccgtctctat tttcaaccgt tcccgtgaaa agaccgaaga agtgattacc gaaaatccag    8700
gcaagaaact ggttccttac tatacggtga agaatttgt  tgaatctctg gaaacgcctc    8760
gtcgcatcct gttaatggtg aaagcaggtg ctggcacgga tgctgctatt gattccctca    8820 agccataccct cgataaaggt gacatcatca ttgatggtgg taacaccttc ttccatgaca    8880
ccattcgtcg taaccgtgag ctttctgcag aaggctttaa ctttatcggt accggtgttt    8940
ccggtggtga agaaggtgcg ctgaaaggtc cttccattat gctggtggg  cagaaagaag    9000 cttatgaact gattgcgccg atcctgacca aaatcgccgc tgtggctgaa gacggcgaac    9060
cgtgcgttac ctatattggt gccgatggtg caggtcatta tgtgaagatg gttcacaacg    9120
gtattgaata cggtgatatg cagctgattg ctgaagccta ttctctgctt aaaggtggct    9180
tgaacctcac caacgaagaa ctggcgcaga ccttttaccga gtggaataac ggtgaactga    9240
gcagctacct gatcgacatc accaaagata tcttcaccaa aaaagatgaa gagggtaact    9300
acctggttga tgtgattctg gatgaagcag caaacaaagg tacgggcaaa tggaccagcc    9360
agagcgcgct ggatctcggc gaaccgctgt cgctgattac cgagtctgtg tttgcacgtt    9420
atatctcttc tctgaaagag cagcgtgttg ccgcatctaa agttctctct ggcccgcaag    9480
cgcagccagc tggcgacaat gctgagttca tcgaaaaagt tcgccgtgcg ctgtatctgg    9540
gcaaaatcgt ttcttacgct cagggcttct ctcagctacg cgctgcgtct gaagagtaca    9600
actgggatct gaactacggt gaaatcgcga agattttccg tgctggctgc atcatccgtg    9660
cgcagttcct gcagaaaatc accgatgctt atgccgaaaa tccgcagatc gctaacctgt    9720
tgctggctcc ttacttcaag caaattgccg atgactacca gcaggcgctg cgcgatgtcg    9780
tcgcttacgc agtacagaac ggtatcccgg tgccgacctt cgccgctgcg gttgcctatt    9840
acgacagcta ccgcgccgct gttctgcctg cgaacctgat ccaggcacag cgtgactatt    9900
tcggtgcgca tacttataag cgcattgata agaaggtgt  gttccatacc gaatggctgg    9960
attaatctga tttaaatcaa ttaatcaaag caaggcccgg agaaaccctc cgggcttttt    10020
tattatacaa agcggcaggt tagggccttt ttttataatt tatagttaaa aacgcgatat    10080
aatacagcgc cgcacagcag gatcgctgcc ttgacagttc atctacatca gcgttaaaaa    10140
tcccgcagta gatgaagctg tggtggtgga ttaatgacca ctctaaatgt ttaaccggaa    10200
gaagtcagag ctaatgaaaa taacaatttc aggaacaggt tatgttggtc tttcaaatgg    10260
tattctgatt gcgcaaaacc acgaagtggt tgcactggat atcgttcagg ccaaagtgga    10320
catgcttaac aagaggcagt caccgcttgt tgataaggag attgaagagt atctggcgac    10380
```

```
taaagatctc aatttccgcg ctacgacaga taagtatgac gcgtataaaa atgccgatta  10440
cgttattatt gccacaccta ccgattatga tccgaaaaca aattatttta ataccctcaag 10500 cgtggaagcg gtcattcgtg atgtgacaga aattaatccc aacgcggtaa tgattataaa  10560
atcaactatc cctgttggtt ttacagagtc cattaaagaa cgttttggta ttgaaaatgt  10620
gatcttttcg cctgagtttt tgcgtgaagg taaagcactt tatgataact acacccatc   10680 acgcattgtg attggcgagc agtctgaacg cgctaaacgt tttgctgcgt tattacagga  10740
aggcgccatt aagcaagaca taccaacatt gtttactgac tcaaccgagg ctgaggcgat  10800
taaacttttt gcgaacactt atctggcgat gcgtgtagcg tatttcaatg aacttgatag  10860
ttatgctgaa agcctgggac ttaattcacg ccagattatt gagggcgtat gccttgaccc  10920
gcgtatcggt aatcactaca acaacccgtc attcggttat ggtggttatt gtctgccgaa  10980
agatactaag cagttactgg caaattacca gtctgtgccg aataacctga tctcggcaat  11040
tgttgacgcc aaccgcacgc gcaaagattt tattgccgat tctatccttg cacgtaaacc  11100
gaaagttgtt ggcgtctatc gtttgattat gaagaatggt tcagacaatt ttcgtgcttc  11160
ctcgattcag ggtattatga agcgaatcaa ggcgaaaggt gtgcctgtaa tcgtttatga  11220
gccagctatg aaagaggacg attttttccg gtcgcgcgtg gtacgtgatc tggatgcgtt  11280
caaacaagaa gctgatgtta ttatttctaa ccgtatgtct gccgatctgg ctgatgtagc  11340
agataaagtt tatacgcgcg acttgtttgg caatgattaa ttattttgtt tcattctaag  11400
aaaaggccct aataaattag ggccttttct tatggttttg taaaatcaaa ctttatagaa  11460
gttacgatac cattctacaa agttctttac cccttcttta actgacgttt caggtttgaa  11520
tcctattacg tcatacagtg cttttgtatc agcactggtt tccagtacat caccgggttg  11580
gagaggcatc atatttttgt tggcttcaat acccagagcc tcttctaacg cattgatata  11640
gtccatcaac tccacaggcg aactattacc aatgttatag acacgatatg gtgctgaact  11700
tgttgcaggc gagcctgttt ctacagccca ctgtgggttt ttttctggaa taacatcctg  11760
taagcgaata atagcttcgg caatatcatc aatgtaagta aagtcacgct tcattttgcc  11820
gaagttgtaa acatcaatgc ttttaccttc cagcatggct ttagtgaatt taaataatgc  11880
catatccgga cgtccccatg gaccataaac cgtaaagaaa cgcagccctg tggtcggtaa  11940
gccatacaaa tgagaatatg tatgggccat gagttcattc gcttttttag ttgctgcata  12000
aagcgaaaca ggatgatcta cagagtcatc tgtagagaaa ggcatcttgc ggttcatgcc  12060
ataaacagaa ctggaggaag cgtaaagtag atgctgaaca ttattatggc gacatccttc  12120
tagtatgttc aggaatccaa tcaggtttgc atctgcatat gcattgggat tttcaagaga  12180
gtaacgtaca ccggcttgcg cagcgaggtt tattacgcgt tcgaaccgct cgtctgcaaa  12240
cagtgccgcc attttctcac gatcggccag gtcaatttta taaaaactga agttgtcgtg  12300
cttgagtaaa tcaagtcgtg cttgtttgag gttgacatcg taataatcat ttaagttgtc  12360
aatgcctaca acctgatgac cagctgcaag aagccgttta cttagataga aaccgataaa  12420
gccagcagct cccgtaacca gaaatttcat ttataatcct cgctcaggct agaatatagc  12480
caatcttcat ctggcataac tgaaagttaa attataccgt tagacaagaa aaaaagataa  12540
tcggtatcag ttctaaactt ggctgttttt tctggtaacg tgctcatttt acaatcaaag  12600
ctgttctaag ctgactatac aagccgacgt cattatctcc aaccgtatgg cagaagagct  12660
taaggatgtg gcagacaaag tctacacccg cgatctcttt ggcagtgact aacatcctgt  12720
```

```
tatcatggcg attttcgccc tgattctctt atgttccctt tgtaataatt cattattttt    12780
atcatttatc ctatagcatt catggcgatt atcgctaaac tatggcggcg cgccacgtgg    12840
gatccccggg taccgagctc gaattcgccc tatagtgagt cgtattacaa ttcactggcc    12900
gtcgttttac aacgtcgtga ctgggaaaac cctggcgtta cccaacttaa tcgccttgca    12960
gcacatcccc ctttcgccag ctggcgtaat agcgaagagg cccgcaccga tcgcccttcc    13020
caacagttgc gcagctgaat ggcgaatggc gcctgatgcg gtattttctc cttacgcatc    13080
tgtgcggtat ttcacaccgc atatggtgca ctctcagtac aatctgctct gatgccgcat    13140
agttaagcca gccccgacac ccgccaacac ccgctgacgc gaacccccttg cggccgcatc    13200 gaatataact tcgtataatg tatgctatac gaagttatta gcgatgagct cggacttcca    13260
ttgttcattc cacggacaaa aacagagaaa ggaaacgaca gaggccaaaa agctcgcttt    13320
cagcacctgt cgtttccttt cttttcagag ggtattttaa ataaaaacat taagttatga    13380
cgaagaagaa cggaaacgcc ttaaaccgga aaattttcat aaatagcgaa acccgcgag    13440 gtcgccgccc cgtaacctgt cggatcaccg gaaaggaccc gtaaagtgat aatgattatc    13500
atctacatat cacaacgtgc gtggaggcca tcaaaccacg tcaaataatc aattatgacg    13560
caggtatcgt attaattgat ctgcatcaac ttaacgtaaa aacaacttca gacaatacaa    13620
atcagcgaca ctgaatacgg ggcaacctca tgtccgagct cgcgagctcg tcgacagcga    13680
cacacttgca tcggatgcag cccggttaac gtgccggcac ggcctgggta accaggtatt    13740
ttgtccacat aaccgtgcgc aaaatgttgt ggataagcag gacacagcag caatccacag    13800
caggcataca accgcacacc gaggttactc cgttctacag gttacgacga catgtcaata    13860
cttgcccttg acaggcattg atggaatcgt agtctcacgc tgatagtctg atcgacaata    13920
caagtgggac cgtggtccca gaccgataat cagaccgaca acacgagtgg gatcgtggtc    13980
ccagactaat aatcagaccg acgatacgag tgggaccgtg gtcccagact aataatcaga    14040
ccgacgatac gagtgggacc gtggttccag actaataatc agaccgacga tacgagtggg    14100
accgtggtcc cagactaata atcagaccga cgatacgagt gggaccatgg tcccagacta    14160
ataatcagac cgacgatacg agtgggaccg tggtcccagt ctgattatca gaccgacgat    14220
acgagtggga ccgtggtccc agactaataa tcagaccgac gatacgagtg gaccgtggt    14280 cccagactaa taatcagacc gacgatacga gtgggaccgt ggtcccagtc tgattatcag    14340
accgacgata caagtggaac agtgggccca gagagaatat tcaggccagt tatgctttct    14400
ggcctgtaac aaaggacatt aagtaaagac agataaacgt agactaaaac gtggtcgcat    14460
cagggtgctg gcttttcaag ttccttaaga atggcctcaa ttttctctat acactcagtt    14520
ggaacacgag acctgtccag gttaagcacc attttatcgc ccttatacaa tactgtcgct    14580
ccaggagcaa actgatgtcg tgagcttaaa ctagttcttg atgcagatga cgttttaagc    14640
acagaagtta aaagagtgat aacttcttca gcttcaaata tcaccccagc ttttttctgc    14700
tcatgaaggt tagatgcctg ctgcttaagt aattcctctt tatctgtaaa ggcttttga    14760 agtgcatcac ctgaccgggc agatagttca ccggggtgag aaaaaagagc aacaactgat    14820
ttaggcaatt tggcggtgtt gatacagcgg gtaataatct tacgtgaaat attttccgca    14880
tcagccagcg cagaaatatt tccagcaaat tcattctgca atcggcttgc ataacgctga    14940
ccacgttcat aagcacttgt tgggcgataa tcgttaccca atctggataa tgcagccatc    15000
tgctcatcat ccagctcgcc aaccagaaca cgataatcac tttcggtaag tgcagcagct    15060
ttacgacggc gactcccatc ggcaatttct atgacaccag atactcttcg accgaacgcc    15120
```

```
ggtgtctgtt gaccagtcag tagaaaagaa gggatgagat catccagtgc gtcctcagta    15180
agcagctcct ggtcacgttc attacctgac catacccgag aggtcttctc aacactatca    15240
ccccggagca cttcaagagt aaacttcaca tcccgaccac atacaggcaa agtaatggca    15300
ttaccgcgag ccattactcc tacgcgcgca attaacgaat ccaccatcgg ggcagctggt    15360
gtcgataacg aagtatcttc aaccggttga gtattgagcg tatgttttgg aataacaggc    15420
gcacgcttca ttatctaatc tcccagcgtg gtttaatcag acgatcgaaa atttcattgc    15480
agacaggttc ccaaatagaa agagcatttc tccaggcacc agttgaagag cgttgatcaa    15540
tggcctgttc aaaaacagtt ctcatccgga tctgaccttt accaacttca tccgtttcac    15600
gtacaacatt ttttagaacc atgcttcccc aggcatcccg aatttgctcc tccatccacg    15660
gggactgaga gccattacta ttgctgtatt tggtaagcaa aatacgtaca tcaggctcga    15720
acccttcaag atcaacgttc ttgagcagat cacgaagcat atcgaaaaac tgcagtgcgg    15780
aggtgtagtc aaacaactca gcaggcgtgg gaacaatcag cacatcagca gcacatacga    15840
cattaatcgt gccgataccc aggttaggcg cgctgtcaat aactatgaca tcatagtcat    15900
gagcaacagt ttcaatggcc agtcggagca tcaggtgtgg atcggtgggc agtttacctt    15960
catcaaattt gcccattaac tcagtttcaa tacggtgcag agccagacag gaaggaataa    16020
tgtcaagccc cggccagcaa gtgggcttta ttgcataagt gacatcgtcc ttttecccaa    16080 gatagaaagg caggagagtg tcttctgcat gaatatgaag atctggtacc catccgtgat    16140
acattgaggc tgttccctgg gggtcgttac cttccacgag caaaacacgt agccccttca    16200
gagccagatc ctgagcaaga tgaacagaaa ctgaggtttt gtaaacgcca cctttatggg    16260
cagcaacccc gatcaccggt ggaaatacgt cttcagcacg tcgcaatcgc gtaccaaaca    16320
catcacgcat atgattaatt tgttcaattg tataaccaac acgttgctca acccgtcctc    16380
gaatttccat atccgggtgc ggtagtcgcc ctgctttctc ggcatctctg atagcctgag    16440
aagaaacccc aactaaatcc gctgcttcac ctattctcca gcgccgggtt attttcctcg    16500
cttccgggct gtcatcatta aactgtgcaa tggcgatagc cttcgtcatt tcatgaccag    16560
cgtttatgca ctggttaagt gttttccatga gtttcattct gaacatcctt taatcattgc    16620
tttgcgtttt tttattaaat cttgcaattt actgcaaagc aacaacaaaa tcgcaaagtc    16680
atcaaaaaac cgcaaagttg tttaaaataa gagcaacact acaaaggag ataagaagag    16740 cacatacctc agtcacttat tatcactagc gctcgccgca gccgtgtaac cgagcatagc    16800
gagcgaactg gcgaggaagc aaagaagaac tgttctgtca gatagctctt acgctcagcg    16860
caagaagaaa tatccaccgt gggaaaaact ccaggtagag gtacacacgc ggatagccaa    16920
ttcagagtaa taaactgtga taatcaaccc tcatcaatga tgacgaacta accccgata    16980 tcaggtcaca tgacgaaggg aaagagaagg aaatcaactg tgacaaactg ccctcaaatt    17040
tggcttcctt aaaaattaca gttcaaaaag tatgagaaaa tccatgcagg ctgaaggaaa    17100
cagcaaaact gtgacaaatt accctcagta ggtcagaaca aatgtgacga accaccctca    17160
aatctgtgac agataaccct cagactatcc tgtcgtcatg gaagtgatat cgcggaagga    17220
aaatacgata tgagtcgtct ggcggccttt ctttttctca atgtatgaga ggcgcattgg    17280
agttctgctg ttgatctcat taacacagac ctgcaggaag cggcggcgga agtcaggcat    17340
acgctggtaa ctttgaggca gctggtaacg ctctatgatc cagtcgattt tcagagagac    17400
gatgcctgag ccatccggct tacgatactg acacagggat tcgtataaac gcatggcata    17460
```

```
cggattggtg atttctttg tttcactaag ccgaaactgc gtaaaccggt tctgtaaccc   17520
gataaagaag ggaatgagat atgggttgat atgtacactg taaagccctc tggatggact   17580
gtgcgcacgt ttgataaacc aaggaaaaga ttcatagcct ttttcatcgc cggcatcctc   17640
ttcagggcga taaaaaacca cttccttccc cgcgaaactc ttcaatgcct gccgtatatc   17700
cttactggct tccgcagagg tcaatccgaa tatttcagca tatttagcaa catggatctc   17760
gcagataccg tcatgttcct gtagggtgcc atcagatttt ctgatctggt caacgaacag   17820
atacagcata cgttttgat cccgggagag actatatgcc gcctcagtga ggtcgtttga   17880
ctggacgatt cgcgggctat ttttacgttt cttgtgattg ataaccgctg tttccgccat   17940
gacagatcca tgtgaagtgt gacaagtttt tagattgtca cactaaataa aaagagtca    18000
ataagcaggg ataactttgt gaaaaacag cttcttctga gggcaatttg tcacagggtt     18060
aagggcaatt tgtcacagac aggactgtca tttgagggtg atttgtcaca ctgaaagggc    18120
aatttgtcac aacaccttct ctagaaccag catggataaa ggcctacaag gcgctctaaa    18180
aaagaagatc taaaaactat aaaaaaaata attataaaaa tatccccgtg gataagtgga    18240
taacccaag  ggaagttttt tcaggcatcg tgtgtaagca gaatatataa gtgctgttcc    18300
ctggtgcttc ctcgctcact cgaccgggag ggttcgagaa ggggggggcac ccccttcgg    18360
cgtgcgcggt cacgcgcaca gggcgcagcc ctggttaaaa acaaggttta taaatattgg    18420
tttaaaagca ggttaaaaga caggttagcg gtggccgaaa acgggcgga aacccttgca    18480
aatgctggat tttctgcctg tggacagccc ctcaaatgtc aataggtgcg cccctcatct    18540
gtcagcactc tgcccctcaa gtgtcaagga tcgcgcccct catctgtcag tagtcgcgcc    18600
cctcaagtgt caataccgca gggcacttat ccccaggctt gtccacatca tctgtgggaa    18660
actcgcgtaa aatcaggcgt tttcgccgat ttgcgaggct ggccagctcc acgtcgccgg    18720
ccgaaatcga gcctgcccct catctgtcaa cgccgcgccg ggtgagtcgg cccctcaagt    18780
gtcaacgtcc gccctcatc tgtcagtgag gccaagtttt ccgcgaggt atccacaacg    18840
ccggcggccg gccgcggtgt ctcgcacacg gcttcgacgg cgtttctggc gcgtttgcag    18900
ggccatagac ggccgccagc ccagcggcga gggcaaccag ccgagggctt cgccctgtcg    18960
ctcgactgcg gcgagcacta ctggctgtaa aaggacagac cacatcatgg ttctgtgttc    19020
attaggttgt tctgtccatt gctgacataa tccgctccac ttcaacgtaa caccgcacga    19080
agatttctat tgttcctgaa ggcatattca atcgttttc gttaccgctt gcaggcatca    19140
tgacagaaca ctacttccta taaacgctac acaggctcct gagattaata atgcggatct    19200
ctacgataat gggagatttt cccgactgtt tcgttcgctt ctcagtggat aacagccagc    19260
ttctctgttt aacagacaaa aacagcatat ccactcagtt ccacatttcc atataaaggc    19320
caaggcattt attctcagga taattgtttc agcatcgcaa ccgcatcaga ctccggcatc    19380
gcaaactgca cccggtgccg ggcagccaca tccagcgcaa aaaccttcgt gtagacttcc    19440
gttgaactga tggacttatg tcccatcagg ctttgcagaa ctttcagcgg tataccggca    19500
tacagcatgt gcatcgcata ggaatggcgg aacgtatgtg gtgtgaccgg aacagagaac    19560
gtcacaccgt cagcagcagc ggcggcaacc gcctccccaa tccaggtcct gaccgttctg    19620
tccgtcactt cccagatccg cgctttctct gtccttcctg tgcgacggtt acgccgctcc    19680
atgagcttat cgcgaataaa tacctgtgac ggaagatcac ttcgcagaat aaataaatcc    19740
tggtgtccct gttgataccg ggaagccctg ggccaacttt tggcgaaaat gagacgttga    19800
tcggcacgta agaggttcca actttcacca taatgaaata agatcactac cgggcgtatt    19860
```

```
ttttgagtta tcgagatttt caggagctaa ggaagctaaa atggagaaaa aaatcactgg    19920
atataccacc gttgatatat cccaatggca tcgtaaagaa cattttgagg catttcagtc    19980
agttgctcaa tgtacctata accagaccgt tcagctggat attacggcct ttttaaagac    20040
cgtaaagaaa aataagcaca agttttatcc ggcctttatt cacattcttg cccgcctgat    20100
gaatgctcat ccggaatttc gtatggcaat gaaagacggt gagctggtga tatgggatag    20160
tgttcaccct tgttacaccg ttttccatga gcaaactgaa acgttttcat cgctctggag    20220
tgaataccac gacgatttcc ggcagtttct acacatatat tcgcaagatg tggcgtgtta    20280
cggtgaaaac ctggcctatt tccctaaagg gtttattgag aatatgtttt tcgtctcagc    20340
caatccctgg gtgagtttca ccagttttga tttaaacgtg gccaatatgg acaacttctt    20400
cgcccccgtt ttcaccatgg gcaaatatta tacgcaaggc gacaaggtgc tgatgccgct    20460
ggcgattcag gttcatcatg ccgtttgtga tggcttccat gtcggcagaa tgcttaatga    20520
attacaacag tactgcgatg agtggcaggg cggggcgtaa ttttttttaag gcagttattg    20580
gtgcccttaa acgcctggtt gctacgcctg aataagtgat aataagcgga tgaatggcag    20640
aaattcgatg ataagctgtc aaacatgaga attggtcgac ggcccgggcg ccgcaaggg    20700
gttcgcgttg gccgattcat taatgcagct ggcacgacag gtttcccgac tggaaagcgg    20760
gcagtgagcg caacgcaatt aatgtgagtt agctcactca ttaggcaccc caggctttac    20820
actttatgct tccggctcgt atgttgtgtg gaattgtgag cggataacaa tttcacacag    20880
gaaacagcta tgaccatgat tacgccaagc tatttaggtg agactataga atactcaagc    20940
ttgcatgcct gcaggtcgac tctagaggat cccacgacgt cg                       20982
```

<210> SEQ ID NO 29
<211> LENGTH: 22887
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29

```
gcggccgcaa ggggttcgcg tcagcgggtg ttggcgggtg tcggggctgg cttaactatg     60
cggcatcaga gcagattgta ctgagagtgc accatatgcg gtgtgaaata ccgcacagat    120
gcgtaaggag aaaataccgc atcaggcgcc attcgccatt cagctgcgca actgttggga    180
agggcgatcg gtgcgggcct cttcgctatt acgccagctg gcgaaagggg gatgtgctgc    240
aaggcgatta agttgggtaa cgccagggtt ttcccagtca cgacgttgta aaacgacggc    300
cagtgaattg taatacgact cactataggg cgaattcgag ctcggtaccc ggggatccca    360
cgtggcgcgc cgccatagtt tagcgataat cgccatgaat gctataggat aaatgataaa    420
ataatgaat tattacaaag ggaacataag agaatcaggg cgaaaatcgc catgataaca    480
ggatgttagt cactgccaaa gagatcgcgg gtgtagactt tgtctgccac atccttaagc    540
tcttctgcca tacggttgga gataatgacg tcggcttgta tagtcagctt agaacagctt    600
tgattgtaaa atgagcacgt taccagaaaa acagccaag tttagaactg ataccgatta    660
tctttttttc ttgtctaacg gtataattta actttcagtt atgccagatg aagattggct    720
atattctagc ctgagcgagg attataaatg aaatttctgg ttacgggagc tgctggcttt    780
atcggtttct atctaagtaa acggcttctt gcagctggtc atcaggttgt aggcattgac    840
aacttaaatg attattacga tgtcaacctc aaacaagcac gacttgattt actcaagcac    900
```

```
gacaacttca gtttttataa aattgacctg gccgatcgtg agaaaatggc ggcactgttt      960
gcagacgagc ggttcgaacg cgtaataaac ctcgctgcgc aagccggtgt acgttactct     1020
cttgaaaatc ccaatgcata tgcagatgca aacctgattg gattcctgaa catactagaa     1080
ggatgtcgcc ataataatgt tcagcatcta ctttacgctt cctccagttc tgtttatggc     1140
atgaaccgca agatgccttt ctctacagat gactctgtag atcatcctgt ttcgctttat     1200
gcagcaacta aaaagcgaa tgaactcatg gcccatacat attctcattt gtatggctta      1260
ccgaccacag ggctgcgttt ctttacggtt tatggtccat ggggacgtcc ggatatggca     1320
ttatttaaat tcactaaagc catgctggaa ggtaaaagca ttgatgttta caacttcggc     1380
aaaatgaagc gtgactttac ttacattgat gatattgccg aagctattat tcgcttacag     1440
gatgttattc cagaaaaaaa cccacagtgg gctgtagaaa caggctcgcc tgcaacaagt     1500
tcagcaccat atcgtgtcta taacattggt aatagttcgc ctgtggagtt gatggactat     1560
atcaatgcgt tagaagaggc tctgggtatt gaagccaaca aaaatatgat gcctctccaa     1620
cccggtgatg tactggaaac cagtgctgat acaaaagcac tgtatgacgt aataggattc     1680
aaacctgaaa cgtcagttaa agaagggggta agaactttg tagaatggta tcgtaacttc     1740
tataaagttt gattttacaa aaccataaga aaggcccta atttattagg gccttttctt      1800
agaatgaaac aaaataatta atcattgcca aacaagtcgc gcgtataaac tttatctgct     1860
acatcagcca gatcggcaga catacggtta gaaataataa catcagcttc ttgtttgaac     1920
gcatccagat cacgtaccac gcgcgaccgg aaaaaatcgt cctctttcat agctggctca     1980
taaacgatta caggcacacc tttcgccttg attcgcttca taataccctg aatcgaggaa     2040
gcacgaaaat tgtctgaacc attcttcata atcaaacgat agacgccaac aactttcggt     2100
ttacgtgcaa ggatagaatc ggcaataaaa tctttgcgcg tgcggttggc gtcaacaatt     2160
gccgagatca ggttattcgg cacagactgg taatttgcca gtaactgctt agtatctttc     2220
ggcagacaat aaccaccata accgaatgac gggttgttgt agtgattacc gatacgcggg     2280
tcaaggcata cgccctcaat aatctggcgt gaattaagtc ccaggctttc agcataacta     2340
tcaagttcat tgaaatacgc tacacgcatc gccagataag tgttcgcaaa aagtttaatc     2400
gcctcagcct cggttgagtc agtaaacaat gttggtatgt cttgcttaat ggcgccttcc     2460
tgtaataacg cagcaaaacg tttagcgcgt tcagactgct cgccaatcac aatgcgtgat     2520
gggtgtaagt tatcataaag tgctttacct tcacgcaaaa actcaggcga aaagatcaca     2580
ttttcaatac caaacgttc tttaatggac tctgtaaaac caacagggat agttgatttt      2640
ataatcatta ccgcgttggg attaatttct gtcacatcac gaatgaccgc ttccacgctt     2700
gaggtattaa ataatttgt tttcggatca taatcggtag gtgtggcaat aataacgtaa      2760
tcggcatttt tatacgcgtc atacttatct gtcgtagcgc ggaaattgag atctttagtc     2820
gccagatact cttcaatctc cttatcaaca agcggtgact gcctcttgtt aagcatgtcc     2880
actttggcct gaacgatatc cagtgcaacc acttcgtggt tttgcgcaat cagaatacca     2940
tttgaaagac caacataacc tgttcctgaa attgttattt tcattagctc tgacttcttc     3000
cggttaaaca tttagagtgg tcattaatcc accaccacag cttcatctac tgcgggattt     3060
ttaacgctga tgtagatgaa ctgtcaaggc agcgatcctg ctgtgcggcg ctgtattata     3120
tcgcgttttt aactataaat tataaaaaaa ggccctaacc tgccgctttg tataataaaa     3180
aagcccggag ggtttctccg ggccttgctt tgattaattg atttaaatca gattaatcca     3240
```

```
gccattcggt atggaacaca ccttctttat caatgcgctt ataagtatgc gcaccgaaat    3300
agtcacgctg tgcctggatc aggttcgcag gcagaacagc ggcgcggtag ctgtcgtaat    3360
aggcaaccgc agcggcgaag gtcggcaccg ggataccgtt ctgtactgcg taagcgacga    3420
catcgcgcag cgcctgctgg tagtcatcgg caatttgctt gaagtaagga gccagcaaca    3480
ggttagcgat ctgcggattt tcggcataag catcggtgat tttctgcagg aactgcgcac    3540
ggatgatgca gccagcacgg aaaatcttcg cgatttcacc gtagttcaga tcccagttgt    3600
actcttcaga cgcagcgcgt agctgagaga agccctgagc gtaagaaacg attttgccca    3660
gatacagcgc acggcgaact ttttcgatga actcagcatt gtcgccagct ggctgcgctt    3720
gcgggccaga gagaacttta gatgcggcaa cacgctgctc tttcagagaa gagatataac    3780
gtgcaaacac agactcggta atcagcgaca gcggttcgcc gagatccagc gcgctctggc    3840
tggtccattt gcccgtacct ttgtttgctg cttcatccag aatcacatca accaggtagt    3900
taccctcttc atctttttg gtgaagatat ctttggtgat gtcgatcagg tagctgctca    3960
gttcaccgtt attccactcg gtaaaggtct gcgccagttc ttcgttggtg aggttcaagc    4020
cacctttaag cagagaatag gcttcagcaa tcagctgcat atcaccgtat tcaataccgt    4080
tgtgaaccat cttcacataa tgacctgcac catcggcacc aatataggta acgcacggtt    4140
cgccgtcttc agccacagcg gcgattttgg tcaggatcgg cgcaatcagt tcataagctt    4200 cttttctgccc accaggcata atggaaggac ctttcagcgc accttcttca ccaccggaaa    4260
caccggtacc gataaagtta aagccttctg cagaaagctc acggttacga cgaatggtgt    4320
catggaagaa ggtgttacca ccatcaatga tgatgtcacc tttatcgagg tatggcttga    4380
gggaatcaat agcagcatcc gtgccagcac ctgctttcac cattaacagg atgcgacgag    4440
gcgtttccag agattcaaca aattctttca ccgtatagta aggaaccagt tcttgcctg     4500 gattttcggt aatcacttct tcggtctttt cacgggaacg gttgaaaata gagacggtat    4560
aaccacggct ttcgatattg agcgcaaggt tgcgccccat cactgccata ccgacgacgc    4620
cgatctgttg ctttgacatt gtttactcct gtcaggatac cgctgggtgg tatgcgggtt    4680
atgcttaatt atagaatatg cctaataaaa ataaatccat aacacttaat cagaaaatta    4740
ttattatcga ttcctaacga ttgaatacat cagctccttt aatttagatg gcattatacg    4800
aaaaaatgtt ctcaacatag cattacttat taattcattt tttcgaataa accaattttt    4860
atattgataa tacaatactt tatactcgta caataaatat gacaatccac gtcgagccat    4920
aagattacga ccagttcgca tttttaataa aatatctgga agatttgcaa atcttgcatt    4980
atgtacaatt aataggctcc acaatgcaaa atcttgagat tttctgaatg gaggataacc    5040
accaacagct aatactgtat tcttttctaaa aattacagaa ggatggctaa ctgcgcttcg    5100
tttcctcgcg aatttaacta tttctctatg ttcgagaggc actttgcgtg ttgaaataaa    5160
ctcctcagta acagtttcaa tttcatcaat aaaactgcca catacatcta tttctgaatt    5220
attaatcata aaagaaattt gtttctcaaa ccgatgaggc aaagaaatat catcagcatc    5280
cattcttgcc actaactcat tcctacaagc ctttaatcct tcatttaagg cattagccaa    5340
tccaacattt ctaggtaaag gtacaaatgt tactatttta ttgccaacat catcaatgaa    5400
tgaatttata atatcgatgt gtgtttgatg gagttctcca tctgcaacaa ttactatttg    5460
atctggctta agtgtttgat cgtgaaaaat agagcgtaga gccacctcaa aaaattgcgg    5520
tagatcattt ttataaatgc taattaaaac tgagaatttt tctaatctat gattcatttc    5580
attttaccac ttcgacccat taaaccgtca ttaatgcctt ttaaaaaaaa atataacctt    5640
```

```
ttattaccat ttggaaggaa aataggatat aaaaaaacct ttccaattaa tttaaccaga    5700
ctagaaattt tccagtagat gggtacataa tttttattta ataaaagaaa gatatttcga    5760
gtagcataat aatgacgaaa tgggcttggc aaaccgacag aaagaatatt taagatctta    5820
aatcgcccat ctccaagtct atgtgcaagt aacgcatttt tattcctaat tactttaaac    5880
ccagcagctc ttaatctcca acaatattca tggtctaccg catcgataaa aagctcatct    5940
ttcattcctc caacaatcaa ccaactatttt tttggtatta gactgccaga acttaatgta   6000
ctatctacct cataataaac ttctgtaagt ggtttccctt tttttaccct tgctttattt    6060
aattcaccag ttactttatc aaaatcttgt gaaccaacta aaccaacatt gacattttgt    6120
ttaagcaatt ttttgtaaca agtaagtaac tgctctacca tcttaggatc aggaatacta    6180
tcctgatcca tttgcaatat aaaatcagcg ccattttcaa aagcccatttt cattcctata   6240 ctttgggctt ctgctatgcc taaattatca ttgaaattga atattttttac atcgcctgaa   6300 gaattttcag catatttata accatttgta gagttattgc aaacgacaac tttagtaact    6360
tgtctcaaca ataattcaac cgcattttttt aaatcattat gttctgggtt gtaagcaacc   6420
aaaacggcat atacagtgtc catcttcacc ttaaaacctt catttagctt tcatcttttt    6480
tagaacatta cttaatgtca ctaatacaat tattacagca acatggttag agtctaaaat    6540
ataaggatta gtaattgcat aagaaacata tagaaaatat agcacacaca actcactgta    6600
ttttatgatt ttaatcgtga gaaggagatt aattaataaa aacaaagtaa ataaaataac    6660
gccaagttga tttaaaaaat aaactgactg caattcataa tatatatatg cactataatc    6720
acggatagga gtttgaattt tgatgacatt acccaaacca gaacctataa caaaatttga    6780
tacagactct gtaagatcat taattaatac agtaaactga tcccatctaa ctcctaaaga    6840
agaatcagct ccatttgatt tcatgattat caactcaatt gaatatgtaa taaaaaagg    6900 gagaatcaca gtaagaaaaa ccccaaaaat aattttcctt aatttagcgt atcgtgagtt    6960
agatttagaa catagtataa tatacataaa aaacaagcat atcgaaacaa aatatgcaaa    7020
attaccagcc actatagtac ctatagccag aataacggtt attgtatttt tgaatcgata    7080
atagaaataa tcttttatga ctatatgcaa cataaaggca aatggaatga gagcatttcc    7140
tttaatttga actctataga aaccacttcc atatgtataa acatcaccat aatcattctc    7200
caaaaaataa tgtcttagtg ctgaataatc accaatacca tatgttttttg tcatataaat   7260 actaatgatg gatataataa ccgcctgtaa taccattaaa tataaaaata ttttaacaat    7320
cgagatggtt ccataagagc agaaataagc acataatata aataatatga taatataaaa    7380
cctaattatt atcgctatat cgttaccctt gatataggaa taaataaaat ttataaaaag    7440
agctaataga aatattaaaa taacaggata gtgatatatt ccgtttgcaa ttttctttgt    7500
aaatgacatg atacaaagac ataaaaaccc ctccataatc caactatatt gaataaatgg    7560
aaagctacgt gtaaggaaaa atataaaccc aaaaacaaa agaacactta aacttttgtc     7620
ttttgagtta taaaaatcag aagtcatgtt tgcactctaa ttagatgggc ttgaggaagt    7680
aatccctaaa atcaattcgc tattaatatt tcgtatcaat taataataat atcaaaaaat    7740
ctaacgatgt tcttacagac catgctattg cggctccaac aattccccaa tgataaataa    7800
aaatatataa tatgcataaa tatgggataa cttcgagcaa atgaataata gctgtaattt    7860
ttgatcttcc actagcctga actgaaacaa atgggatttg tgcaatgcaa ttaaaaaaga    7920
aacctattgc aagaatttttt aatactatac ctggcgtccc atgatatgta ggtcccatcc   7980
```

```
aagcggacat tataaaatct gataaaataa ttatcaacat tacaattgga agtataccaa    8040
taaccattat aaaatatgat aatattttag tttgctttac cgattgcaat tctgaactta    8100
atcttggaaa aatagctctg gacaacgcac ttggtaatat cgttaagcgt tgtataccat    8160
cagacggagc agtataaaaa gaaactttat cagcccccac aatgtgtgaa agaataaaac    8220
gatccatata tgtcataata gggctaataa tattgctaac tgttatccag cttccaaagc    8280
cgattaatct tttaactgtt acaattttta cagacagccc agatgatatt attagttttc    8340
gactaaatat aaaggtcact ataagtgata agactcttgc cataactaaa ccatatatag    8400
cacttagtaa tcctccatga aaaaacaga aaatcactgg taatccagcc acaaaagagt    8460
tgttaattga ttttattaaa tttacttttc tgaactttc catccctca aaaatcccca     8520 accagacttg gtttaacaag tataagggta tggtagctga ataatatat attgctttga    8580 cagattctac aacatgattc gcgttaatgt ttaataattt aacaattaca ttgctactca    8640
aaaatagtac actaccgcca atcaagccca atatagttag aattaccgtt gaagttgaaa    8700
tgatcgctct taattcttta tgaacatttt tatatattga acttctctt ataacagctc     8760 tggtcaatcc agcatcaaaa atacttgcat atccaactaa ggcaatagct aacgtaaaaa    8820
ggccaaattg ctcggtccct agaattctag acagtatacc taacgcagga attgctatta    8880
atgatggtat aatataccca cttatattcc ataaagtatt ctttacaata ctcacaaaaa    8940
taattccttc atgttatgca attctttagc ccttgcatct ttaatcgata aaatataatt    9000
attatgttct atcgtcggcc attttatgct cagaatagga tcattccata caatccctct    9060
atcactatca ggatgataat agttcgtcgt tttatataaa aattccgcag tctcgctcag    9120
caccaaaaaa ccatgtgcaa atccctcagg gatccacaat tgccgcttat tctcagcaga    9180
taaattcacc ccaacccatt taccaaaggt aggcgacgat ttacgaatat caacagctac    9240
atcaaaaacc tcaccaacaa cgcaacgtac cagtttccct tgcgcataag gttctaactg    9300
ataatgcagc ccgcgtaaaa caccttact agacttcgaa tggttatcct gaacaaattc     9360
aaccttacgt cctacagctt cttcgaaaac tttctgatta agctttcca taaagaaacc    9420 acgctcatca ccaaaaactt tcggctcgaa aattaacaca tcaggaattt ctgttttaat    9480
tacgttcatt ttattaataa cctttaatca ttttcagcag atactgtcca taagcatttt    9540
ttttcagcgg ctccgctaat gctttcacct gttcagcatc aataaaccct ttacggtaag    9600
caatttcttc tgggcaggaa acctttagtc cctggcgctc ttcaatggtg gcaatgaagt    9660
tgcttgcttc aataagactc tgatgtgtcc ccgtatccag ccatgcataa ccacgcccca    9720
tcatggcaac ggataaacgc ccctgttcca tataaatacg gttaatatcg gtaatttcca    9780
gttcaccacg ggcagaaggc ttaaggtttt tcgccatttc gacaacgtcg ttatcataga    9840
aataaagccc ggttaccgca taattacttt ttggttgtag cggtttttct tccaggctta    9900
ttgccgtacc gttttatca aactcaacga cgccgtagcg ttcaggatca ttaacgtgat      9960
aggcaaatac cgttgcacca cttctttgt taacagcgac atccattaac ttcggcagat    10020
catgaccgta gaagatatta tcaccaagaa ccaaagcaca atcatcacca ccgataaact    10080
cttcaccgat aataaacgcc tgcgcaagcc catctggagt cggttgcact tgtactgaa     10140 gatttagccc ccactggcta ccgtcaccta gcagttgttg aaaacgagga gtatcctgtg    10200
gcgtactaat aatcagaata tcgcgaatac ccgccaacat cagtgtagag agcgggtaat    10260
agatcatcgg cttatcataa ataggtaata gctgttact gacagccata gtcacaggat     10320
aaagacgtgt accagaacca cccgctaaaa taataccttt acgcgttttc atttcatcat    10380
```

```
tcctttaat  tcatcttgct  ccaccatcac  gaacaagatg  caaaaactat  taaattgctg    10440
tagtcgtaat  taattcgttg  agcattcgtt  tcacaccaac  ctgccagtca  ggcaagacaa    10500
gcgcaaagtt  ctgctgaaat  ttttctgtat  taaggcgaga  gttatgtgga  cgacgagctg    10560
gtgtaggata  ggctgttgtt  ggtactgcgt  tgagcttgtt  gagtgcaagg  ggaatacctg    10620
ctttgcgcgc  ctcttcaaaa  accagcgcag  cataatcgtg  ccaggttgtg  gtaccactgg    10680
ctaccagatg  gtacaaacct  gcgacttccg  gtttattcag  tgccacacga  atagcatgtg    10740
ccgtacaatc  agccagcagc  tcagcacctg  ttggcgcacc  aaattgatca  tttatcacag    10800
ccagttcttc  gcgctctttt  gccagacgca  acatcgtttt  ggcgaagtta  tttcctttag    10860
ctgcgtatac  ccagctggta  cggaaaataa  gatgcttcgc  gcaatgttcc  tgtaacgctt    10920
tttctccggc  taacttggtt  tcaccgtaaa  catttagcgg  tgcggttgca  tccgtctcca    10980
gccatggcgt  gtcgccattt  ccagggaata  cgtagtcagt  tgagtaatga  attacccaag    11040
ccccaacttc  attagcctct  tttgcaattg  attcaacact  agtcgcattg  agtaattgtg    11100
caaattcggg  ttctgactca  gccttatcta  ctgcggtgtg  agccgcagca  ttaacaataa    11160
catcaggtcg  aattcttttg  actgtttcag  ctacaccttc  aggattacta  aaatcaccac    11220
aataatcagt  ggagtgaaca  tcaagagcaa  tcaaattacc  caaaggtgcc  agagcacgct    11280
gtagttccca  acctacctgc  cctgttttgc  cgaaaaggag  gatattcatt  actggcggcc    11340
ctcatagttc  tgttcaatcc  acgattgata  agcaccactt  ttcacattat  caacccattt    11400
tgtattggac  aggtaccatt  ccaatgtctt  ccgaatcccg  ctctcaaacg  tttcctgcgg    11460
tttccagccc  aattcgcggc  taatcttctc  tgcatcaatc  gcataacggc  gatcgtgtcc    11520
cgggcgatcg  gcaacataag  taatttgctc  gcggtaagat  ttctcttcg   gtacaatctc    11580 atccagcaaa  tcacaaatag  tgagcactac  atcgatgttt  ttcttttcgt  tgtgtccacc    11640
aatgttataa  gtttcacccg  ctttaccttc  ggttacgacg  gtatataacg  cacgcgcatg    11700
atcttcaaca  tacagccagt  cacgaatttg  atccccttg   ccataaatag  gtaatgcctt    11760
accttccaga  gcattcagaa  taaccaatgg  aatcaatttt  tccgggaaat  gataaggacc    11820
ataattatta  gagcaattag  tcacaatggt  tggtaaacca  taggtacgtt  tccacgcgcg    11880
gactaaatga  tcgctggatg  cttttgaagc  ggaataaggg  ctgcttggcg  cgtaagctgt    11940
tgtctctgta  aataagggta  attcttctgt  attatttacc  tcgtcaggat  gaggcaaatc    12000
accatagact  tcgtcagtag  aaatatgatg  aaaacggaat  ctagttttct  tgtcgctatc    12060
aagagcagac  caataattgc  gagcggcttc  caaaaggaca  tatgtaccaa  caatattggt    12120
ttcaataaat  gccgcaggac  ctgtaattga  acggtcaaca  tggctttcag  cagccaggtg    12180
catcactgca  tctggctgat  gctgagcaaa  aatccgtgcc  attgcagctg  catcgcaaat    12240
atccgcatgt  tcaaaaacat  agcgttcaga  atcagaaaca  tcagcaagtg  attccaggtt    12300
tccggcgtac  gttaatttat  cgacattaac  aacactatcc  tgcgtattat  ttataatgtg    12360
acgaactaca  gcaaaaccaa  taaatcctgc  gccaccagta  acaagtattt  tcacctaatt    12420
tattccatat  tgcttcagag  catgctgtga  aataagcggc  tctcagtttg  attaatagaa    12480
gtattaatgc  acgctaccgc  ccctggcttt  acagctacca  gagcactgca  tgcatgccta    12540
cgatgtgacg  agcgttaccc  actcgcgcta  aacccgaaaa  attcaaaagc  taattgtctt    12600
accaatccgc  tctggaaaca  aggaaaaatcc  tggaaaactt  tgactaaaat  cctattgcta    12660
actcgttgtt  attctgattg  tttatataaa  acaacggcag  gaatattcgc  aacaaattac    12720
```

```
tttcaccacg aatcttcact gccgttataa ttttcttatc aaccgttaca tccggtcaga    12780
ttttcattat tcgcttaaca gcttctcaat acctttacgg aacttcgccc cttctttcag    12840
gttgcgcagc ccatacttca caaacgcctg catatagccc attttttac cgcagtcgta     12900 gctgtcgccg gtcatcagca ttgcatcaac ggactgtttt ttcgccagct cggcaatggc    12960
atcagtcagc tgaatacgtc cccatgcacc aggctgagta cgttcaagtt ccggccaaat    13020
atcggcagaa agcacatagc gaccaacggc catgatgtct gagtccagcg tctgcggctg    13080
atccggtttt tcgataaatt caacaatgcg gctgactta ccttcgcgat ccagcggttc      13140
tttggtctgg atgacggagt attcagagag gtcacccggc atacgttttg ccagcacctg    13200
gctacggccc gtttcattga agcgcgcaat catggcagca aggttgtagc gtagcgggtc    13260
ggcgctggcg tcgtcgatca caacgtctgg cagcaccacg acaaatggat tgtcaccaat    13320
ggcgggtcgt gcacacaaaa tggagtgacc taaacctaaa ggttcgccct gacgcacgtt    13380
cataatagtc acgcccggcg ggcagataga ttgcacttcc gccagtagtt gacgcttcac    13440
gcgctgctca aggagagatt ctaattcata agaggtgtcg aagtggtttt cgaccgcgtt    13500
cttggacgca tgagttacca ggaggatttc tttgatccct gcagccacaa tctcgtcaac    13560
aatgtactga atcattggct tgtcgacgat cggtagcatc tctttgggta tcgccttagt    13620
ggcaggcaac atatgcatcc caagacccgc taccggtata actgctttta aattcgtcat    13680
tattttccta cctctaaggg gctgatagtg cgtaaattat tgtcataggt tagccaaacg    13740
gtatggctat ataccaagca taactttgat taaaccttac gataacacta cacaccatca    13800
gcatctgggt tactcggatt actcggaaat ccacatactg ataatttaat cagtacctct    13860
ttccgaataa tcgtagtcca acctggtcct tttttctctg actcgtctgc attactcaga    13920
aacaaacgtt atgtcgtctt ttttggcatg gacgaattca tactgcagag ttcgatccag    13980
accttgcgac agcgtatacg gtgcaacaaa acctgaagaa tgcactttcg ttgcgtcaaa    14040
ctgtgttgtt gcgcagaatt ttttcacgcg cacagagctg acagcgtatt ttttgcccgt    14100
aattttgctc aggatatcaa agcaatatcc acccagcatt cctagtgggt aaggcaagtg    14160
catagaaggg atcttttgt tcaggctttg ttcaacttca gcaaccaact ggttcatgtt      14220
caggtctggc ttatcaacat agttataaac ctcataacct gcggcaacat tcttcagttt    14280
gtacttgata aactcaacaa tgttccaac ataagccatg gacttatagt tagtccctgc      14340
gcccaccatc ataaacttgc cgccagcgat ctgtttcagc aagttataga cgttaccgcg    14400
gttgcgttca ccgaagataa cggtaggacg gatgatggtt aatgaacgtt ctgttggtgc    14460
tttgttatac cattcacgca gcacttcctc tgcctgccac ttacttttgc cgtagtggtt    14520
gaaagggtcg tgtggatggt tttcgtcagg gttgtgtttg ttcaaaccat aaacagcaac    14580
ggaactggta aagatgatat ttttaacgcc attttttcc atggccgcca gcacattgcg      14640
ggtaccctga acgttgacat cataatagag agaagtaggg ctgacgtcat cgcggtgttc    14700
cgctgccagt agtacaacag tgtcaaaacc ggctaacgcc tggtcgagtg cctgttgatc    14760
acgaacatca ccaatctgtg tgatttctgg ataaaagtgg ctctgccgtt tgtccaggtt    14820
cttgatatta aagtcagcaa ttgccgtttc aagtagtcgg gttcctacga atccggaagc    14880
tcctatgagc aaaacgttat tgttcataaa tcactttagt ctggttgtta cgtaagaaac    14940
acaagataaa gatgagtacc ttccctgagt agtcaatgct gcccagcccc agctttaaca    15000
gttagtgtga ggattataat cttttagaac attatatcca gtaagtttat gaatggtcgc    15060
aaatctactc tctccgttcc ggcaatctaa agttaatgct agcgacgtcg tgggatcctc    15120
```

```
tagagtcgac ctgcaggcat gcaagcttga gtattctata gtctcaccta aatagcttgg   15180
cgtaatcatg gtcatagctg tttcctgtgt gaaattgtta ccgctcaca attccacaca   15240 acatacgagc cggaagcata aagtgtaaag cctggggtgc ctaatgagtg agctaactca   15300
cattaattgc gttgcgctca ctgcccgctt tccagtcggg aaacctgtcg tgccagctgc   15360
attaatgaat cggccaacgc gaaccccttg cggccgcccg ggccgtcgac caattctcat   15420
gtttgacagc ttatcatcga atttctgcca ttcatccgct tattatcact tattcaggcg   15480
tagcaaccag gcgtttaagg gcaccaataa ctgccttaaa aaattacgc cccgccctgc   15540 cactcatcgc agtactgttg taattcatta agcattctgc cgacatggaa gccatcacaa   15600
acggcatgat gaacctgaat cgccagcggc atcagcacct tgtcgccttg cgtataatat   15660
ttgcccatgg tgaaaacggg ggcgaagaag ttgtccatat tggccacgtt taaatcaaaa   15720
ctggtgaaac tcacccaggg attggctgag acgaaaaaca tattctcaat aaacccttta   15780
gggaaatagg ccaggttttc accgtaacac gccacatctt gcgaatatat gtgtagaaac   15840
tgccggaaat cgtcgtggta ttcactccag agcgatgaaa acgtttcagt ttgctcatgg   15900
aaaacggtgt aacaagggtg aacactatcc catatcacca gctcaccgtc tttcattgcc   15960
atacgaaatt ccggatgagc attcatcagg cgggcaagaa tgtgaataaa ggccggataa   16020
aacttgtgct tatttttctt tacggtcttt aaaaaggccg taatatccag ctgaacggtc   16080
tggttatagg tacattgagc aactgactga atgcctcaa aatgttcttt acgatgccat   16140
tgggatatat caacggtggt atatccagtg atttttttct ccattttagc ttccttagct   16200
cctgaaaatc tcgataactc aaaaaatacg cccggtagtg atcttatttc attatggtga   16260 aagtggaac ctcttacgtg ccgatcaacg tctcattttc gccaaaagtt ggcccagggc   16320
ttcccggtat caacagggac accaggattt atttattctg cgaagtgatc ttccgtcaca   16380
ggtatttatt cgcgataagc tcatggagcg cgtaaccgt cgcacaggaa ggacagagaa   16440
agcgcggatc tgggaagtga cggacagaac ggtcaggacc tggattgggg aggcggttgc   16500
cgccgctgct gctgacggtg tgacgttctc tgttccggtc acaccacata cgttccgcca   16560
ttcctatgcg atgcacatgc tgtatgccgg tataccgctg aaagttctgc aaagcctgat   16620
gggacataag tccatcagtt caacggaagt ctacacgaag ttttttgcgc tggatgtggc   16680
tgcccggcac cgggtgcagt ttgcgatgcc ggagtctgat gcggttgcga tgctgaaaca   16740
attatcctga gaataaatgc cttggccttt atatggaaat gtggaactga gtggatatgc   16800 tgttttgtc tgttaaacag agaagctggc tgttatccac tgagaagcga acgaaacagt   16860
cgggaaaatc tcccattatc gtagagatcc gcattattaa tctcaggagc ctgtgtagcg   16920
tttataggaa gtagtgttct gtcatgatgc ctgcaagcgg taacgaaaac gatttgaata   16980
tgccttcagg aacaatagaa atcttcgtgc ggtgttacgt tgaagtggag cggattatgt   17040
cagcaatgga cagaacaacc taatgaacac agaaccatga tgtggtctgt ccttttacag   17100
ccagtagtgc tcgccgcagt cgagcgacag ggcgaagccc tcggctggtt gccctcgccg   17160
ctgggctggc ggccgtctat ggccctgcaa acgcgccaga aacgccgtcg aagccgtgtg   17220
cgagacaccg cggccggccg ccggcgttgt ggatacctcg cggaaaactt ggccctcact   17280
gacagatgag gggcggacgt tgacacttga ggggccgact caccccggcgc ggcgttgaca   17340 gatgaggggc aggctcgatt tcggccgcg acgtggagct ggccagcctc gcaaatcggc   17400
gaaaacgcct gattttacgc gagtttccca cagatgatgt ggacaagcct ggggataagt   17460
```

```
gccctgcggt attgacactt gaggggcgcg actactgaca gatgaggggc gcgatccttg    17520
acacttgagg ggcagagtgc tgacagatga ggggcgcacc tattgacatt tgaggggctg    17580
tccacaggca gaaaatccag catttgcaag ggtttccgcc cgttttcgg ccaccgctaa     17640 cctgtctttt aacctgcttt taaaccaata tttataaacc ttgtttttaa ccagggctgc    17700
gccctgtgcg cgtgaccgcg cacgccgaag gggggtgccc cccttctcg aaccctcccg     17760 gtcgagtgag cgaggaagca ccagggaaca gcacttatat attctgctta cacacgatgc    17820
ctgaaaaaac ttcccttggg gttatccact tatccacggg gatatttta taattatttt     17880 ttttatagtt tttagatctt cttttttaga gcgccttgta ggcctttatc catgctggtt    17940
ctagagaagg tgttgtgaca aattgccctt tcagtgtgac aaatcaccct caaatgacag    18000
tcctgtctgt gacaaattgc ccttaaccct gtgacaaatt gccctcagaa gaagctgttt    18060
tttcacaaag ttatccctgc ttattgactc ttttttattt agtgtgacaa tctaaaaact    18120
tgtcacactt cacatggatc tgtcatggcg gaaacagcgg ttatcaatca caagaaacgt    18180
aaaaatagcc cgcgaatcgt ccagtcaaac gacctcactg aggcggcata tagtctctcc    18240
cgggatcaaa aacgtatgct gtatctgttc gttgaccaga tcagaaaatc tgatggcacc    18300
ctacaggaac atgacggtat ctgcgagatc catgttgcta aatatgctga aatattcgga    18360
ttgacctctg cggaagccag taaggatata cggcaggcat tgaagagttt cgcggggaag    18420
gaagtggttt tttatcgccc tgaagaggat gccggcgatg aaaaaggcta tgaatctttt    18480
ccttggttta tcaaacgtgc gcacagtcca tccagagggc tttacagtgt acatatcaac    18540
ccatatctca ttcccttctt tatcgggtta cagaaccggt ttacgcagtt tcggcttagt    18600
gaaacaaaag aaatcaccaa tccgtatgcc atgcgtttat acgaatccct gtgtcagtat    18660
cgtaagccgg atggctcagg catcgtctct ctgaaaatcg actggatcat agagcgttac    18720
cagctgcctc aaagttacca gcgtatgcct gacttccgcc gccgcttcct gcaggtctgt    18780
gttaatgaga tcaacagcag aactccaatg cgcctctcat acattgagaa aaagaaaggc    18840
cgccagacga ctcatatcgt attttccttc gcgatatca cttccatgac gacaggatag    18900
tctgagggtt atctgtcaca gatttgaggg tggttcgtca catttgttct gacctactga    18960
gggtaatttg tcacagtttt gctgtttcct tcagcctgca tggattttct catactttt     19020 gaactgtaat ttttaaggaa gccaaatttg agggcagttt gtcacagttg atttccttct    19080
ctttcccttc gtcatgtgac ctgatatcgg gggttagttc gtcatcattg atgagggttg    19140
attatcacag tttattactc tgaattggct atccgcgtgt gtacctctac ctggagtttt    19200
tcccacggtg gatatttctt cttgcgctga gcgtaagagc tatctgacag aacagttctt    19260
ctttgcttcc tcgccagttc gctcgctatg ctcggttaca cggctgcggc gagcgctagt    19320
gataataagt gactgaggta tgtgctcttc ttatctcctt ttgtagtgtt gctcttattt    19380
taaacaactt tgcggttttt tgatgacttt gcgattttgt tgttgctttg cagtaaattg    19440
caagatttaa taaaaaacg caaagcaatg attaaaggat gttcagaatg aaactcatgg    19500
aaacacttaa ccagtgcata aacgctggtc atgaaatgac gaaggctatc gccattgcac    19560
agtttaatga tgacagcccg gaagcgagga aaataacccg cgctggaga ataggtgaag     19620 cagcggattt agttggggtt tcttctcagg ctatcagaga tgccgagaaa gcagggcgac    19680
taccgcaccc ggatatggaa attcgaggac gggttgagca acgtgttggt tatacaattg    19740
aacaaattaa tcatatgcgt gatgtgtttg gtacgcgatt gcgacgtgct gaagacgtat    19800
ttccaccggt gatcggggtt gctgcccata aggtggcgt ttacaaaacc tcagtttctg     19860
```

```
ttcatcttgc tcaggatctg gctctgaagg ggctacgtgt tttgctcgtg gaaggtaacg   19920
acccccaggg aacagcctca atgtatcacg gatgggtacc agatcttcat attcatgcag   19980
aagacactct cctgcctttc tatcttgggg aaaaggacga tgtcacttat gcaataaagc   20040
ccacttgctg gccggggctt gacattattc cttcctgtct ggctctgcac cgtattgaaa   20100
ctgagttaat gggcaaattt gatgaaggta aactgcccac cgatccacac ctgatgctcc   20160
gactggccat tgaaactgtt gctcatgact atgatgtcat agttattgac agcgcgccta   20220
acctgggtat cggcacgatt aatgtcgtat gtgctgctga tgtgctgatt gttcccacgc   20280
ctgctgagtt gtttgactac acctccgcac tgcagttttt cgatatgctt cgtgatctgc   20340
tcaagaacgt tgatcttaaa gggttcgagc ctgatgtacg tattttgctt accaaataca   20400
gcaatagtaa tggctctcag tccccgtgga tggaggagca aattcgggat gcctggggaa   20460
gcatggttct aaaaaatgtt gtacgtgaaa cggatgaagt tggtaaaggt cagatccgga   20520
tgagaactgt ttttgaacag gccattgatc aacgctcttc aactggtgcc tggagaaatg   20580
ctctttctat ttgggaacct gtctgcaatg aaatttccga tcgtctgatt aaaccacgct   20640
gggagattag ataatgaagc gtgcgcctgt tattccaaaa catacgctca atactcaacc   20700
ggttgaagat acttcgttat cgacaccagc tgccccgatg gtggattcgt taattgcgcg   20760
cgtaggagta atggctcgcg gtaatgccat tactttgcct gtatgtggtc gggatgtgaa   20820
gtttactctt gaagtgctcc gggggtgtag tgttgagaag acctctcggg tatggtcagg   20880
taatgaacgt gaccaggagc tgcttactga ggacgcactg gatgatctca tcccttcttt   20940
tctactgact ggtcaacaga caccggcgtt cggtcgaaga gtatctggtg tcatagaaat   21000
tgccgatggg agtcgccgtc gtaaagctgc tgcacttacc gaaagtgatt atcgtgttct   21060
ggttggcgag ctggatgatg agcagatggc tgcattatcc agattgggta acgattatcg   21120
cccaacaagt gcttatgaac gtggtcagcg ttatgcaagc cgattgcaga atgaatttgc   21180
tggaaatatt tctgcgctgg ctgatgcgga aaatatttca cgtaagatta ttacccgctg   21240
tatcaacacc gccaaattgc ctaaatcagt tgttgctctt ttttctcacc ccggtgaact   21300
atctgcccgg tcaggtgatg cacttcaaaa agcctttaca gataaagagg aattacttaa   21360
gcagcaggca tctaaccttc atgagcagaa aaaagctggg gtgatatttg aagctgaaga   21420
agttatcact cttttaactt ctgtgcttaa aacgtcatct gcatcaagaa ctagtttaag   21480
ctcacgacat cagtttgctc ctggagcgac agtattgtat aagggcgata aaatggtgct   21540
taacctggac aggtctcgtg ttccaactga gtgtatagag aaaattgagg ccattcttaa   21600
ggaacttgaa aagccagcac cctgatgcga ccacgtttta gtctacgttt atctgtcttt   21660
acttaatgtc ctttgttaca ggccagaaag cataactggc ctgaatattc tctctgggcc   21720
cactgttcca cttgtatcgt cggtctgata atcagactgg gaccacggtc ccactcgtat   21780
cgtcggtctg attattagtc tgggaccacg gtcccactcg tatcgtcggt ctgattatta   21840
gtctgggacc acggtcccac tcgtatcgtc ggtctgataa tcagactggg accacggtcc   21900
cactcgtatc gtcggtctga ttattagtct gggaccatgg tcccactcgt atcgtcggtc   21960
tgattattag tctgggacca cggtcccact cgtatcgtcg gtctgattat tagtctggaa   22020
ccacggtccc actcgtatcg tcggtctgat tattagtctg gaccacggt cccactcgta   22080 tcgtcggtct gattattagt ctgggaccac gatcccactc gtgttgtcgg tctgattatc   22140
ggtctgggac cacggtccca cttgtattgt cgatcagact atcagcgtga gactacgatt   22200
ccatcaatgc ctgtcaaggg caagtattga catgtcgtcg taacctgtag aacggagtaa   22260
```

```
cctcggtgtg cggttgtatg cctgctgtgg attgctgctg tgtcctgctt atccacaaca    22320
ttttgcgcac ggttatgtgg acaaaatacc tggttaccca ggccgtgccg gcacgttaac    22380
cgggctgcat ccgatgcaag tgtgtcgctg tcgacgagct cgcgagctcg gacatgaggt    22440
tgccccgtat tcagtgtcgc tgatttgtat tgtctgaagt tgtttttacg ttaagttgat    22500
gcagatcaat taatacgata cctgcgtcat aattgattat ttgacgtggt ttgatggcct    22560
ccacgcacgt tgtgatatgt agatgataat cattatcact ttacgggtcc tttccggtga    22620
tccgacaggt tacggggcgg cgacctcgcg ggttttcgct atttatgaaa attttccggt    22680
ttaaggcgtt tccgttcttc ttcgtcataa cttaatgttt ttatttaaaa taccctctga    22740
aaagaaagga aacgacaggt gctgaaagcg agcttttttgg cctctgtcgt ttcctttctc   22800 tgttttttgtc cgtggaatga acaatggaag tccgagctca tcgctaataa cttcgtatag   22860
catacattat acgaagttat attcgat                                        22887
```

```
<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 30

His His His His His His
1               5

<210> SEQ ID NO 31
<211> LENGTH: 5
<212> TYPE: PRT
<213> ORGANISM: Artificial Sequence
<220> FEATURE:
<223> OTHER INFORMATION: N-glycosylation consensus sequence
<220> FEATURE:
<221> NAME/KEY: VARIANT
<222> LOCATION: (1)..(1)
<223> OTHER INFORMATION: Xaa = Asp or Glu
<220> FEATURE:
<221> NAME/KEY: VARIANT
<222> LOCATION: (2)..(2)
<223> OTHER INFORMATION: Xaa = Any natural accuring Amino acid except
      Proline
<220> FEATURE:
<221> NAME/KEY: VARIANT
<222> LOCATION: (4)..(4)
<223> OTHER INFORMATION: Xaa = Any natural accuring Amino acid except
      Proline
<220> FEATURE:
<221> NAME/KEY: VARIANT
<222> LOCATION: (5)..(5)
<223> OTHER INFORMATION: Xaa = Ser or Thr

<400> SEQUENCE: 31

Xaa Xaa Asn Xaa Xaa
1               5
```